United States Patent
Shai et al.

(10) Patent No.: US 9,890,202 B2
(45) Date of Patent: Feb. 13, 2018

(54) PEPTIDES BASED ON THE TRANSMEMBRANE DOMAIN OF A TOLL-LIKE RECEPTOR (TLR) FOR TREATMENT OF TLR-MEDIATED DISEASES

(75) Inventors: Yechiel Shai, Yahud (IL); Avner Fink, Rehovot (IL); Eliran-Moshe Reuven, Rehovot (IL); Liraz Shmuel-Galia, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/811,226

(22) PCT Filed: Jul. 19, 2011

(86) PCT No.: PCT/IL2011/000573
§ 371 (c)(1),
(2), (4) Date: Apr. 8, 2013

(87) PCT Pub. No.: WO2012/011100
PCT Pub. Date: Jan. 26, 2012

(65) Prior Publication Data
US 2013/0225478 A1    Aug. 29, 2013

Related U.S. Application Data

(60) Provisional application No. 61/365,559, filed on Jul. 19, 2010.

(51) Int. Cl.
*A61K 38/16* (2006.01)
*A61K 38/10* (2006.01)
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)
*C07K 14/705* (2006.01)
*C07K 7/08* (2006.01)
*C07K 4/00* (2006.01)
*C07K 14/00* (2006.01)
*A61K 38/03* (2006.01)

(52) U.S. Cl.
CPC ............ *C07K 14/705* (2013.01); *A61K 38/03* (2013.01); *A61K 38/04* (2013.01); *A61K 38/10* (2013.01); *A61K 38/16* (2013.01); *C07K 4/00* (2013.01); *C07K 7/08* (2013.01); *C07K 14/00* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,869,447 A | 2/1999 | Henke et al. | |
| 6,818,621 B2 | 11/2004 | Ashkar | |
| 7,029,861 B1 | 4/2006 | Beutler et al. | |
| 7,271,248 B2 | 9/2007 | Hardiman et al. | |
| 8,697,631 B2 | 4/2014 | Nakamura et al. | |
| 2004/0043931 A1* | 3/2004 | Hersberg et al. | 514/12 |
| 2005/0163764 A1 | 7/2005 | Medzhitov et al. | |
| 2006/0210588 A1* | 9/2006 | Bachmann et al. | 424/208.1 |
| 2006/0292119 A1 | 12/2006 | Chen et al. | |
| 2007/0020232 A1 | 1/2007 | Rossignol et al. | |
| 2007/0134762 A1 | 6/2007 | Arumugham et al. | |
| 2008/0241139 A1 | 10/2008 | Delucia | |
| 2010/0297165 A1* | 11/2010 | Berzofsky | A61K 39/39 424/193.1 |
| 2014/0220074 A1 | 8/2014 | Shai et al. | |
| 2016/0184426 A9 | 6/2016 | Shai et al. | |

FOREIGN PATENT DOCUMENTS

| | | | |
|---|---|---|---|
| EP | 1522856 | 4/2005 | |
| EP | 1522856 A1 * | 4/2005 | G01N 33/68 |
| WO | WO 98/50547 | 11/1998 | |
| WO | WO 00/24776 | 5/2000 | |
| WO | WO 01/47944 | 7/2001 | |
| WO | WO 2005/077411 | 8/2005 | |
| WO | WO 2009/079564 | 6/2009 | |
| WO | WO 2012/011100 | 1/2012 | |
| WO | WO 2013/054329 | 4/2013 | |

OTHER PUBLICATIONS

NCBI Datase, GenBank Accession No. AAH14693, "Toll-like receptor 2 [Mus musculus]", 2 pages, (2006).*
Rebl, et al., "Toll-like receptor signaling in bony fish," Vet. Immunol. Immunopathol. 134:139-150 (Apr. 2010).*
Rock et al., "A family of human receptors structurally related to *Drosophila* Toll," Proc. Natl. Acad. Sci. USA 95:588-593 (1998).*
Matsushima, et al., "Comparative sequence analysis of leucine-rich repeats (LRRs) within vertebrate toll-like receptors," BMC Genomics 8:124 (2007).*
Smirnova, et al., "Phylogenetic variation and polymorphism at the Toll-like receptor 4 locus (TLR4)," 1:1-10 (2000).*
Nicol, et al., Nature 187:483-485 (1960).*
UniProt Database, Accession No. Q15399, accessed on Jun. 29, 2015.*
Takeuchi et al., Gene 231:59-65 (1999).*
Heine et al., J. Immunol. 162:6971-6975 (1999).*

(Continued)

*Primary Examiner* — Hasan Ahmed
*Assistant Examiner* — Thea D'Ambrosio

(57) ABSTRACT

Peptides are provided that are capable of inhibiting cell activation mediated by a Toll-like receptor (TLR) selected from TLR 1, 2, 4 or 6, said peptide comprising a sequence consisting of, or found within, the sequence of the transmembrane domain of a TLR selected from TLR 1, 2, 4 or 6 and optionally cytoplasmic and extracellular regions flanking the transmembrane domain. These peptides as well as pharmaceutical composition comprising them are useful for the treatment of TLR-mediated disease.

13 Claims, 15 Drawing Sheets

(56) References Cited

OTHER PUBLICATIONS

Medzhitov et al., Nature 388:394-397 (1997).*
UniProt Database, "TLR1_HUMAN", Accession No. Q15399, 11 pages (accessed on Jun. 29, 2015).*
Database EPO Proteins [Online], Jan. 16, 2004, "Sequence 8636 from Patent WO0147944", XP002661693, retrieved from EBI accession No. EPOP: CQ009996.
Database EPO Proteins [Online], Nov. 24, 2009, "Subname: Full=Truncated vpu protein:", XP002661694, retrieved from EBI accession No. UNIPROT: DOEMZ5.
Tsung, et al., "A novel inhibitory peptide of Toll-like receptor signaling limits lipopolysaccharide-induced production of inflammatory mediators and enhances survival in mice", SHOCK (Philadelphia): Injury, Inflammation, and Sepsis: Laboratory and Clinical Approaches, Lippinocott Willims & Wilkins, US, vol. 27, No. 4, Apr. 1, 2007, pp. 364-369, XP009130298.
Brinkmann, et al., "The interaction between the ER membrane protein UNC93B and TLR3, 7, and 9 is crucial for TLR signaling", The Journal of Cell Biology, vol. 177, No. 2, Apr. 1, 2007, pp. 265-275, XP55010026.
Toschchakov, et al., "Cell-penetrating TIR BB loop decoy peptides a novel class of TLR signaling inhibitors and a tool to study topology of TIR-TIR interactions", Expert Opinion on Biological Therapy, Informa Healthcare, UK, vol. 7, No. 7, Jul. 1, 2007, pp. 1035-1050, XP008107407.
International Search Report issued in PCT/IL2011/000573 dated Oct. 31, 2011.
Fink et al.; "Assembly of the TLR2/6 Transmembrane Domains Is Essential for Activation and Is a Target for Prevention of Sepsis"; The Journal of Immunology; 190; pp. 6410-6422; (2013).
Office Action Dated May 18, 2015 From the Israel Patent Office Re. Application No. 224259 and Its Translation Into English.
Communication Pursuant to Article 94(3) EPC Dated May 30, 2014 From the European Patent Office Re. Application No. 11749552.3.
International Preliminary Report on Patentability Dated Jan. 22, 2013 From the International Bureau of WIPO Re. Application No. PCT/IL2011/000573.
NCBI "Toll-Like Receptor 2 [Mus Musculus]", NCBI Database [Online], 2006.
Rebl et al. "Toll-Like Receptor Signaling in Bony Fish", Veterinary Immunology and Immunopathology, 134: 139-150, 2010.
Rock et al. "A Family of Human Receptors Structurally Related to Drosophila Toll", Proc. Natl. Acad. Sci. USA, 95: 588-593, Jan. 1998.
Shimkets et al. "Patents Protein Sequence 8636 From Patent WO 01/47944", EMBL-EBI Database [Online], EBI Dbfetch, Database Accession No. CQ009996, Jan. 16, 2004.
UniProtKB "Toll-Like Receptor 2 Precursor—Tlr2—Mus musculus (Mouse)", UniProtKb/Swiss-Prot Database [Online], Database Accession No. Q9QUN7, Version 126, Last Modified Apr. 16, 2014.
Wu et al. "Structural Requirements of Angiotensin I-Converting Enzyme Inhibitory Peptides: Quantitative Structure-Activity Realtionship Study of Di- and Tripeptides", Journal of Agricultural and Food Chemistry, 54: 732-738, Published on Web Jan. 4, 2006.
Communication Pursuant to Article 94(3) EPC Dated Sep. 14, 2015 From the European Patent Office Re. Application No. 11749552.3.
Communication Pursuant to Article 94(3) EPC Dated Jan. 20, 2015 From the European Patent Office Re. Application No. 12784739.0.
Communication Pursuant to Article 94(3) EPC Dated May 28, 2015 From the European Patent Office Re. Application No. 12784739.0.
International Preliminary Report on Patentability Dated Apr. 15, 2014 From the International Bureau of WIPO Re. Application No. PCT/IL2012/050396.
International Search Report and the Written Opinion Dated Feb. 19, 2013 From the International Searching Authority Re. Application No. PCT/IL2012/050396.
Official Action Dated Apr. 30, 2015 From the US Patent and Trademark Office Re. U.S. Appl. No. 14/249,709.
Tsung et al. "A Novel Inhibitory Peptide of Toll-Like Receptor Signaling Limits Lipopolysaccharide-induced Production of Inflammatory Mediators and Enhances Survival in Mice", Shock, XP009130298, 27(4): 364-369, Apr. 1, 2007.
Akira et al. "Toll-Like Receptors: Critical Proteins Linking Innate and Acquired Immunity", Nature Immunology, 2(8): 675-680, Aug. 2001.
Benkirane et al. "Antigenicity and Immunogenicity of Modified Synthetic Peptides Containing D-Amino Acid Residues. Antibodies to A D-Enantiomer Do Recognize the Parent L-Hexapeptide and Reciprocally", The Journal of Biological Chemistry, 268(35): 26279-26285, Dec. 15, 1993.
Berns et at "Adenovirus and Adeno-Associated Virus as Vectors for Gene Therapy", Annals of the New York Academy of Sciences, 772: 95-104, Nov. 27, 1995.
Beutler "TLR4 as the Mammalian Endotoxin Sensor", Current Topics in Microbiology and Immunology, 270: 109-120, 2002.
Federoff et al. "Expression of Nerve Growth Factor In Vivo From a Defective Herpes Simplex Virus 1 Vector Prevents Effects of Axotomy on Sympathetic Ganglia", Proc. Natl. Acad. Sci. USA, 89(5): 1636-1640, Mar. 1992.
Fink el al. "Gene Transfer to Neurons Using Herpes Simplex Virus-Based Vectors", Annual Review of Neuroscience, 19: 265-287, 1996.
Langosch et al. "Dimerisation of the Glycophorin a Transmembrane Segment in Membranes Probed With the ToxR Transcription Activator", The Journal of Molecular Biology, 263(4): 525-530, Nov. 8, 1996.
Merrifield "Solid Phase Peptide Synthesis. I. The Synthesis of a Tetrapeptide", Journal of the American Chemical Society, JACS, 85(14): 2149-2154, Jul. 20, 1963.
Nishiya et al. "Ligand-Independent Oligomerization of TLR4 Regulated by a Short Hydrophobic Region Adjjacent to the Transmembrane Domain", Biochemical and Biophysical Research Communications, 341(4): 1128-1134, Available Online Jan. 26, 2006.
Quintana et al. "Induction of IgG3 to LPS Via Toll-Like Receptor 4 Co-Stimulation", PLoS ONE, 3(10): c3509-1-c3509-11, Oct. 23, 2008.
Qureshi et al. "Endotoxin-Tolerant Mice Have Mutations in Toll-Like Receptor 4 (Tlr4)", The Journal of Experimental Medicine, 189(4): 615-625, Feb. 15, 1999.
Riedeman et al. "Novel Strategies for the Treatment of Sepsis", Natural Medicine, 9(5): 517-524, May 2003.
Notice of Reasons for Refusal Dated Jul. 15, 2015 From the Japanese Patent Office Re. Application No. 2013-520284 and Its Translation Into English.
Official Action Dated Jul. 1, 2016 From the US Patent and Trademark Office Re. U.S. Appl. No. 14/249,709.
Mukherjee et al. "TLR2 and TLR4 Mediated Host Immune Responses in Major Infectious Diseases: A Review", The Brazilian Journal of Infectious Diseases, 20(2): 193-204, Apr. 2016.
NCBI "Sequence 2 from U.S. Pat. No. 7,029,861, LPS-Response Gene Compositions and Methods", Database NCBI [Online], GenBank: ABH65774.1, Database Accession No. ABH65774, Apr. 18, 2006.
O'Neill et al. "Therapeutic Targeting of Toll-Like Receptors for Infectious and Inflammatory Diseases and Cancer", Pharmacological Reviews, 61(2): 177-197, 2009.

* cited by examiner

SEQUENCE LISTING

```
<160> NUMBER OF SEQ ID NOS: 123

<210> SEQ ID NO 1
<211> LENGTH: 21
<212> TYPE: PRT
<213> ORGANISM: Artificial Sequence
<220> FEATURE:
<223> OTHER INFORMATION: synthetic peptide

<400> SEQUENCE: 1

Leu Leu Ile Val Thr Ile Val Ala Thr Met Leu Val Leu Ala Val Thr
1               5                   10                  15

Val Thr Ser Leu Cys
            20

<210> SEQ ID NO 2
<211> LENGTH: 40
<212> TYPE: PRT
<213> ORGANISM: Artificial Sequence
<220> FEATURE:
<223> OTHER INFORMATION: synthetic peptide

<400> SEQUENCE: 2

Asp Phe His Met Ser Glu Leu Ser Cys Asn Ile Thr Leu Leu Ile Val
1               5                   10                  15

Thr Ile Val Ala Thr Met Leu Val Leu Ala Val Thr Val Thr Ser Leu
            20                  25                  30

Cys Ile Tyr Leu Asp Leu Pro Trp
        35                  40
```

-continued

```
<210> SEQ ID NO 3
<211> LENGTH: 22
<212> TYPE: PRT
<213> ORGANISM: Artificial Sequence
<220> FEATURE:
<223> OTHER INFORMATION: synthetic peptide

<400> SEQUENCE: 3

Ala Leu Val Ser Gly Met Cys Cys Ala Leu Phe Leu Leu Ile Leu Leu
1               5                   10                  15

Thr Gly Val Leu Cys His
            20

<210> SEQ ID NO 4
<211> LENGTH: 40
<212> TYPE: PRT
<213> ORGANISM: Artificial Sequence
<220> FEATURE:
<223> OTHER INFORMATION: synthetic peptide

<400> SEQUENCE: 4

Asp Val Arg Leu Ser Val Ser Glu Cys His Arg Thr Ala Leu Val Ser
1               5                   10                  15

Gly Met Cys Cys Ala Leu Phe Leu Leu Ile Leu Leu Thr Gly Val Leu
            20                  25                  30

Cys His Arg Phe His Gly Leu Trp
        35                  40

<210> SEQ ID NO 5
<211> LENGTH: 21
<212> TYPE: PRT
<213> ORGANISM: Artificial Sequence
<220> FEATURE:
<223> OTHER INFORMATION: synthetic peptide

<400> SEQUENCE: 5

Leu Leu Ile Val Thr Ile Gly Ala Thr Met Leu Val Leu Ala Val Thr
1               5                   10                  15

Val Thr Ser Leu Cys
            20

<210> SEQ ID NO 6
<211> LENGTH: 40
<212> TYPE: PRT
<213> ORGANISM: Artificial Sequence
<220> FEATURE:
<223> OTHER INFORMATION: synthetic peptide

<400> SEQUENCE: 6

Asp Phe His Met Ser Glu Leu Ser Cys Asn Ile Thr Leu Leu Ile Val
1               5                   10                  15

Thr Ile Gly Ala Thr Met Leu Val Leu Ala Val Thr Val Thr Ser Leu
            20                  25                  30

Cys Ile Tyr Leu Asp Leu Pro Trp
        35                  40

<210> SEQ ID NO 7
<211> LENGTH: 21
<212> TYPE: PRT
<213> ORGANISM: Artificial Sequence
<220> FEATURE:
<223> OTHER INFORMATION: synthetic peptide

<400> SEQUENCE: 7
```

Val Leu Leu Thr Val Thr Ile Gly Ala Thr Met Leu Val Leu Ala Val
1               5                   10                  15

Thr Gly Ala Phe Leu
            20

<210> SEQ ID NO 8
<211> LENGTH: 43
<212> TYPE: PRT
<213> ORGANISM: Artificial Sequence
<220> FEATURE:
<223> OTHER INFORMATION: synthetic peptide

<400> SEQUENCE: 8

Asp Phe His Met Ser Pro Leu Ser Cys Asp Thr Val Leu Leu Thr Val
1               5                   10                  15

Thr Ile Gly Ala Thr Met Leu Val Leu Ala Val Thr Gly Ala Phe Leu
            20                  25                  30

Cys Leu Tyr Phe Asp Leu Pro Trp Tyr Val Arg
        35                  40

<210> SEQ ID NO 9
<211> LENGTH: 21
<212> TYPE: PRT
<213> ORGANISM: Artificial Sequence
<220> FEATURE:
<223> OTHER INFORMATION: synthetic peptide

<400> SEQUENCE: 9

Ala Ala Leu Val Ser Gly Val Cys Cys Ala Leu Leu Leu Ile Leu
1               5                   10                  15

Leu Val Gly Ala Leu
            20

<210> SEQ ID NO 10
<211> LENGTH: 46
<212> TYPE: PRT
<213> ORGANISM: Artificial Sequence
<220> FEATURE:
<223> OTHER INFORMATION: synthetic peptide

<400> SEQUENCE: 10

Arg Leu Gln Asp Ala Arg Pro Ser Val Leu Glu Cys His Gln Ala Ala
1               5                   10                  15

Leu Val Ser Gly Val Cys Cys Ala Leu Leu Leu Ile Leu Leu Val
            20                  25                  30

Gly Ala Leu Cys His His Phe His Gly Leu Trp Tyr Leu Arg
        35                  40                  45

<210> SEQ ID NO 11
<211> LENGTH: 21
<212> TYPE: PRT
<213> ORGANISM: Artificial Sequence
<220> FEATURE:
<223> OTHER INFORMATION: synthetic peptide

<400> SEQUENCE: 11

Val Leu Leu Thr Ile Thr Ile Gly Ala Thr Met Leu Val Leu Ala Val
1               5                   10                  15

Thr Gly Ala Phe Leu
            20

<210> SEQ ID NO 12
<211> LENGTH: 43

```
<212> TYPE: PRT
<213> ORGANISM: Artificial Sequence
<220> FEATURE:
<223> OTHER INFORMATION: synthetic peptide

<400> SEQUENCE: 12

Asp Phe His Met Ser Pro Leu Ser Cys Asp Thr Val Leu Leu Thr Ile
1               5                   10                  15

Thr Ile Gly Ala Thr Met Leu Val Leu Ala Val Thr Gly Ala Phe Leu
            20                  25                  30

Cys Leu Tyr Phe Asp Leu Pro Trp Tyr Val Arg
        35                  40

<210> SEQ ID NO 13
<211> LENGTH: 30
<212> TYPE: PRT
<213> ORGANISM: Artificial Sequence
<220> FEATURE:
<223> OTHER INFORMATION: synthetic peptide

<400> SEQUENCE: 13

Thr Ile Ile Ser Val Ser Val Val Ser Val Ile Val Val Ser Thr Val
1               5                   10                  15

Ala Phe Leu Ile Tyr His Phe Tyr Phe His Leu Ile Leu Ile
            20                  25                  30

<210> SEQ ID NO 14
<211> LENGTH: 43
<212> TYPE: PRT
<213> ORGANISM: Artificial Sequence
<220> FEATURE:
<223> OTHER INFORMATION: synthetic peptide

<400> SEQUENCE: 14

Thr Ile Ile Ser Val Ser Val Val Ser Val Ile Val Val Ser Thr Val
1               5                   10                  15

Ala Phe Leu Ile Tyr His Phe Tyr Phe His Leu Ile Leu Ile Ala Gly
            20                  25                  30

Cys Lys Lys Tyr Ser Arg Gly Glu Ser Ile Tyr
        35                  40

<210> SEQ ID NO 15
<211> LENGTH: 21
<212> TYPE: PRT
<213> ORGANISM: Artificial Sequence
<220> FEATURE:
<223> OTHER INFORMATION: synthetic peptide

<400> SEQUENCE: 15

Thr Ile Ile Gly Val Ser Val Leu Ser Val Leu Val Ser Val Val
1               5                   10                  15

Ala Val Leu Val Tyr
            20

<210> SEQ ID NO 16
<211> LENGTH: 40
<212> TYPE: PRT
<213> ORGANISM: Artificial Sequence
<220> FEATURE:
<223> OTHER INFORMATION: synthetic peptide

<400> SEQUENCE: 16

Ser Leu Asn Ile Thr Cys Gln Met Asn Lys Thr Ile Ile Gly Val Ser
1               5                   10                  15
```

Val Leu Ser Val Leu Val Ser Val Val Ala Val Leu Val Tyr Lys
            20                  25                  30

Phe Tyr Phe His Leu Met Leu Leu
        35                  40

<210> SEQ ID NO 17
<211> LENGTH: 17
<212> TYPE: PRT
<213> ORGANISM: Artificial Sequence
<220> FEATURE:
<223> OTHER INFORMATION: synthetic peptide

<400> SEQUENCE: 17

Leu Leu Ile Val Thr Ile Val Ala Thr Met Leu Val Leu Ala Val Thr
1               5                   10                  15

Val

<210> SEQ ID NO 18
<211> LENGTH: 18
<212> TYPE: PRT
<213> ORGANISM: Artificial Sequence
<220> FEATURE:
<223> OTHER INFORMATION: synthetic peptide

<400> SEQUENCE: 18

Ala Leu Val Ser Gly Met Cys Cys Ala Leu Phe Leu Leu Ile Leu Leu
1               5                   10                  15

Thr Gly

<210> SEQ ID NO 19
<211> LENGTH: 18
<212> TYPE: PRT
<213> ORGANISM: Artificial Sequence
<220> FEATURE:
<223> OTHER INFORMATION: synthetic peptide

<400> SEQUENCE: 19

Leu Leu Thr Val Thr Ile Gly Ala Thr Met Leu Val Leu Ala Val Thr
1               5                   10                  15

Gly Ala

<210> SEQ ID NO 20
<211> LENGTH: 18
<212> TYPE: PRT
<213> ORGANISM: Artificial Sequence
<220> FEATURE:
<223> OTHER INFORMATION: synthetic peptide

<400> SEQUENCE: 20

Ala Leu Val Ser Gly Val Cys Cys Ala Leu Leu Leu Leu Ile Leu Leu
1               5                   10                  15

Val Gly

<210> SEQ ID NO 21
<211> LENGTH: 21
<212> TYPE: PRT
<213> ORGANISM: Artificial Sequence
<220> FEATURE:
<223> OTHER INFORMATION: synthetic peptide

<400> SEQUENCE: 21

Thr Ile Ile Gly Val Ser Val Leu Ser Val Leu Val Ser Val Val
1               5                   10                  15

```
Ala Val Leu Val Tyr
            20

<210> SEQ ID NO 22
<211> LENGTH: 17
<212> TYPE: PRT
<213> ORGANISM: Artificial Sequence
<220> FEATURE:
<223> OTHER INFORMATION: synthetic peptide

<400> SEQUENCE: 22

Val Ser Val Leu Ser Val Leu Val Val Ser Val Val Ala Val Leu Val
1               5                   10                  15

Tyr

<210> SEQ ID NO 23
<211> LENGTH: 17
<212> TYPE: PRT
<213> ORGANISM: Artificial Sequence
<220> FEATURE:
<223> OTHER INFORMATION: synthetic peptide

<400> SEQUENCE: 23

Leu Ile Val Thr Ile Gly Ala Thr Met Leu Val Leu Ala Val Thr Val
1               5                   10                  15

Thr

<210> SEQ ID NO 24
<211> LENGTH: 19
<212> TYPE: PRT
<213> ORGANISM: Artificial Sequence
<220> FEATURE:
<223> OTHER INFORMATION: synthetic peptide

<400> SEQUENCE: 24

Leu Ala Val Thr Val Thr Ser Leu Cys Ile Tyr Leu Asp Leu Pro Trp
1               5                   10                  15

Tyr Leu Arg

<210> SEQ ID NO 25
<211> LENGTH: 16
<212> TYPE: PRT
<213> ORGANISM: Artificial Sequence
<220> FEATURE:
<223> OTHER INFORMATION: synthetic peptide

<400> SEQUENCE: 25

Leu Ile Leu Leu Thr Gly Val Leu Cys His Arg Phe His Gly Leu Trp
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: synthetic peptide

<400> SEQUENCE: 26

Leu Ala Val Thr Gly Ala Phe Leu Cys Leu Tyr Phe Asp Leu Pro Trp
1               5                   10                  15

<210> SEQ ID NO 27
<211> LENGTH: 16
<212> TYPE: PRT
```

```
<213> ORGANISM: Artificial Sequence
<220> FEATURE:
<223> OTHER INFORMATION: synthetic peptide

<400> SEQUENCE: 27

Leu Ile Leu Leu Val Gly Ala Leu Cys His His Phe His Gly Leu Trp
1               5                   10                  15

<210> SEQ ID NO 28
<211> LENGTH: 18
<212> TYPE: PRT
<213> ORGANISM: Artificial Sequence
<220> FEATURE:
<223> OTHER INFORMATION: synthetic peptide

<400> SEQUENCE: 28

Val Val Ser Val Val Ala Val Leu Val Tyr Lys Phe Tyr Phe His Leu
1               5                   10                  15

Met Leu

<210> SEQ ID NO 29
<211> LENGTH: 17
<212> TYPE: PRT
<213> ORGANISM: Artificial Sequence
<220> FEATURE:
<223> OTHER INFORMATION: synthetic peptide

<400> SEQUENCE: 29

Ala Phe Leu Ile Tyr His Phe Tyr Phe His Leu Ile Leu Ile Ala Gly
1               5                   10                  15

Cys

<210> SEQ ID NO 30
<211> LENGTH: 17
<212> TYPE: PRT
<213> ORGANISM: Artificial Sequence
<220> FEATURE:
<223> OTHER INFORMATION: synthetic peptide

<400> SEQUENCE: 30

Val Ala Phe Leu Ile Tyr His Phe Tyr Phe His Leu Ile Leu Ile Ala
1               5                   10                  15

Gly

<210> SEQ ID NO 31
<211> LENGTH: 15
<212> TYPE: PRT
<213> ORGANISM: Artificial Sequence
<220> FEATURE:
<223> OTHER INFORMATION: synthetic peptide

<400> SEQUENCE: 31

His Phe Tyr Phe His Leu Ile Leu Ile Ala Gly Cys Lys Lys Tyr
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: synthetic peptide

<400> SEQUENCE: 32

Ser Cys Asp Thr Val Leu Leu Thr Val Thr Ile Gly Ala Thr Met Leu
1               5                   10                  15
```

Val

<210> SEQ ID NO 33
<211> LENGTH: 17
<212> TYPE: PRT
<213> ORGANISM: Artificial Sequence
<220> FEATURE:
<223> OTHER INFORMATION: synthetic peptide

<400> SEQUENCE: 33

Ser Pro Leu Ser Cys Asp Thr Val Leu Leu Thr Val Thr Ile Gly Ala
1               5                   10                  15

Thr

<210> SEQ ID NO 34
<211> LENGTH: 17
<212> TYPE: PRT
<213> ORGANISM: Artificial Sequence
<220> FEATURE:
<223> OTHER INFORMATION: synthetic peptide

<400> SEQUENCE: 34

Thr Val Leu Leu Thr Val Thr Ile Gly Ala Thr Met Leu Val Leu Ala
1               5                   10                  15

Val

<210> SEQ ID NO 35
<211> LENGTH: 17
<212> TYPE: PRT
<213> ORGANISM: Artificial Sequence
<220> FEATURE:
<223> OTHER INFORMATION: synthetic peptide

<400> SEQUENCE: 35

Leu Val Leu Ala Val Thr Gly Ala Phe Leu Cys Leu Tyr Phe Asp Leu
1               5                   10                  15

Pro

<210> SEQ ID NO 36
<211> LENGTH: 17
<212> TYPE: PRT
<213> ORGANISM: Artificial Sequence
<220> FEATURE:
<223> OTHER INFORMATION: synthetic peptide

<400> SEQUENCE: 36

Gly Ala Phe Leu Cys Leu Tyr Phe Asp Leu Pro Trp Tyr Val Arg Met
1               5                   10                  15

Leu

<210> SEQ ID NO 37
<211> LENGTH: 17
<212> TYPE: PRT
<213> ORGANISM: Artificial Sequence
<220> FEATURE:
<223> OTHER INFORMATION: synthetic peptide

<400> SEQUENCE: 37

Thr Ile Gly Ala Thr Met Leu Val Leu Ala Val Thr Gly Ala Phe Leu
1               5                   10                  15

Cys

```
<210> SEQ ID NO 38
<211> LENGTH: 17
<212> TYPE: PRT
<213> ORGANISM: Artificial Sequence
<220> FEATURE:
<223> OTHER INFORMATION: synthetic peptide

<400> SEQUENCE: 38

Met Leu Val Leu Ala Val Thr Gly Ala Phe Leu Cys Leu Tyr Phe Asp
1               5                   10                  15

Leu

<210> SEQ ID NO 39
<211> LENGTH: 17
<212> TYPE: PRT
<213> ORGANISM: Artificial Sequence
<220> FEATURE:
<223> OTHER INFORMATION: synthetic peptide

<400> SEQUENCE: 39

Met Leu Val Leu Ala Val Thr Gly Ala Phe Leu Ala Leu Tyr Phe Asp
1               5                   10                  15

Leu

<210> SEQ ID NO 40
<211> LENGTH: 17
<212> TYPE: PRT
<213> ORGANISM: Artificial Sequence
<220> FEATURE:
<223> OTHER INFORMATION: synthetic peptide

<400> SEQUENCE: 40

Leu Val Leu Ala Val Thr Gly Ala Phe Leu Cys Leu Tyr Phe Asp Leu
1               5                   10                  15

Pro

<210> SEQ ID NO 41
<211> LENGTH: 17
<212> TYPE: PRT
<213> ORGANISM: Artificial Sequence
<220> FEATURE:
<223> OTHER INFORMATION: synthetic peptide

<400> SEQUENCE: 41

Gly Ala Phe Leu Cys Leu Tyr Phe Asp Leu Pro Trp Tyr Val Arg Met
1               5                   10                  15

Leu

<210> SEQ ID NO 42
<211> LENGTH: 16
<212> TYPE: PRT
<213> ORGANISM: Artificial Sequence
<220> FEATURE:
<223> OTHER INFORMATION: synthetic peptide

<400> SEQUENCE: 42

Ala Val Thr Val Thr Ser Leu Cys Ile Tyr Leu Asp Leu Pro Trp Tyr
1               5                   10                  15

<210> SEQ ID NO 43
<211> LENGTH: 18
<212> TYPE: PRT
<213> ORGANISM: Artificial Sequence
<220> FEATURE:
<223> OTHER INFORMATION: synthetic peptide
```

-continued

<400> SEQUENCE: 43

Ser Glu Leu Ser Cys Asn Ile Thr Leu Leu Ile Val Thr Ile Gly Ala
1               5                   10                  15

Thr Met

<210> SEQ ID NO 44
<211> LENGTH: 16
<212> TYPE: PRT
<213> ORGANISM: Artificial Sequence
<220> FEATURE:
<223> OTHER INFORMATION: synthetic peptide

<400> SEQUENCE: 44

Leu Ala Val Thr Gly Ala Phe Leu Ala Leu Tyr Phe Asp Leu Pro Trp
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: synthetic peptide

<400> SEQUENCE: 45

Leu Ala Val Thr Gly Ala Phe Leu Ala Leu Tyr Phe Ala Leu Pro Trp
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: synthetic peptide

<400> SEQUENCE: 46

Leu Ala Val Thr Gly Ala Phe Leu Ala Ser Tyr Phe Asp Leu Pro Trp
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: synthetic peptide

<400> SEQUENCE: 47

Leu Ile Leu Leu Val Gly Ala Leu Ala His His Phe His Gly Leu Trp
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: synthetic peptide

<400> SEQUENCE: 48

Leu Ile Leu Leu Val Gly Ala Leu Ala Ala Ala Phe Ala Gly Leu Trp
1               5                   10                  15

<210> SEQ ID NO 49
<211> LENGTH: 18
<212> TYPE: PRT
<213> ORGANISM: Artificial Sequence
<220> FEATURE:

<223> OTHER INFORMATION: synthetic peptide

<400> SEQUENCE: 49

Ala Leu Val Ser Gly Val Ala Ala Ala Leu Leu Leu Ile Leu Leu
1               5                   10                  15

Val Gly

<210> SEQ ID NO 50
<211> LENGTH: 35
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (34)..(34)
<223> OTHER INFORMATION: X indicates A or S

<400> SEQUENCE: 50

Ala Phe Leu Ile Tyr His Phe Tyr Phe His Leu Ile Leu Ile Ala Gly
1               5                   10                  15

Ala Ala Phe Leu Ile Tyr His Phe Tyr Phe His Leu Ile Leu Ile Ala
            20                  25                  30

Gly Xaa Ala
        35

<210> SEQ ID NO 51
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: X indicates R,K,H or A
<220> FEATURE:
<221> NAME/KEY: MISC_FEATURE
<222> LOCATION: (9)..(9)
<223> OTHER INFORMATION: X indicates R,K,H or A

<400> SEQUENCE: 51

Phe Leu Ile Tyr Xaa Phe Tyr Phe Xaa Leu Ile Leu Ile Ala Gly Cys
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: X indicates R,K,H or A
<220> FEATURE:
<221> NAME/KEY: MISC_FEATURE
<222> LOCATION: (11)..(11)
<223> OTHER INFORMATION: X indicates R,K,H or A

<400> SEQUENCE: 52

Val Ala Phe Leu Ile Tyr Xaa Phe Tyr Phe Xaa Leu Ile Leu Ile Ala
1               5                   10                  15

Gly

<210> SEQ ID NO 53
<211> LENGTH: 15

```
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X indicates R,K,H or A
<220> FEATURE:
<221> NAME/KEY: MISC_FEATURE
<222> LOCATION: (5)..(5)
<223> OTHER INFORMATION: X indicates R,K,H or A

<400> SEQUENCE: 53

Xaa Phe Tyr Phe Xaa Leu Ile Leu Ile Ala Gly Cys Lys Lys Tyr
1               5                   10                  15

<210> SEQ ID NO 54
<211> LENGTH: 27
<212> TYPE: PRT
<213> ORGANISM: Artificial Sequence
<220> FEATURE:
<223> OTHER INFORMATION: synthetic peptide

<400> SEQUENCE: 54

Ser Ala Asp Thr Val Leu Leu Thr Val Thr Ala Cys Asp Thr Val Leu
1               5                   10                  15

Leu Thr Val Thr Ile Gly Ala Thr Met Leu Val
            20                  25

<210> SEQ ID NO 55
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: X indicates A or S

<400> SEQUENCE: 55

Ser Xaa Asp Thr Val Leu Leu Thr Val Thr Ile Gly Ala Thr Met Leu
1               5                   10                  15

Val

<210> SEQ ID NO 56
<211> LENGTH: 17
<212> TYPE: PRT
<213> ORGANISM: Artificial Sequence
<220> FEATURE:
<223> OTHER INFORMATION: synthetic peptide

<400> SEQUENCE: 56

Ser Cys Asp Ala Val Leu Leu Ala Val Ala Ile Gly Ala Ala Met Leu
1               5                   10                  15

Val

<210> SEQ ID NO 57
<211> LENGTH: 17
<212> TYPE: PRT
<213> ORGANISM: Artificial Sequence
<220> FEATURE:
<223> OTHER INFORMATION: synthetic peptide

<400> SEQUENCE: 57

Ala Pro Leu Ala Cys Asp Thr Val Leu Leu Thr Val Thr Ile Gly Ala
```

```
<210> SEQ ID NO 58
<211> LENGTH: 17
<212> TYPE: PRT
<213> ORGANISM: Artificial Sequence
<220> FEATURE:
<223> OTHER INFORMATION: synthetic peptide

<400> SEQUENCE: 58

Thr Val Leu Leu Thr Val Thr Ile Gly Ala Thr Ile Leu Val Leu Ala
1               5                   10                  15
Val

<210> SEQ ID NO 59
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (11)..(11)
<223> OTHER INFORMATION: with X indicates S or A

<400> SEQUENCE: 59

Leu Val Leu Ala Val Thr Gly Ala Phe Leu Xaa Leu Tyr Phe Asp Leu
1               5                   10                  15
Pro

<210> SEQ ID NO 60
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (15)..(15)
<223> OTHER INFORMATION: X indicates E or A

<400> SEQUENCE: 60

Leu Val Leu Ala Val Thr Gly Ala Phe Leu Cys Leu Tyr Phe Xaa Leu
1               5                   10                  15
Pro

<210> SEQ ID NO 61
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: X indicates S or A

<400> SEQUENCE: 61

Gly Ala Phe Leu Xaa Leu Tyr Phe Asp Leu Pro Trp Tyr Val Arg Met
1               5                   10                  15
Leu

<210> SEQ ID NO 62
<211> LENGTH: 17
```

<212> TYPE: PRT
<213> ORGANISM: Artificial Sequence
<220> FEATURE:
<223> OTHER INFORMATION: synthetic peptide

<400> SEQUENCE: 62

Gly Ala Phe Leu Cys Leu Tyr Phe Asp Leu Pro Trp Tyr Val Arg Ile
1               5                   10                  15
Leu

<210> SEQ ID NO 63
<211> LENGTH: 17
<212> TYPE: PRT
<213> ORGANISM: Artificial Sequence
<220> FEATURE:
<223> OTHER INFORMATION: synthetic peptide

<400> SEQUENCE: 63

Thr Ile Gly Ala Thr Ile Leu Val Leu Ala Val Thr Gly Ala Phe Leu
1               5                   10                  15
Cys

<210> SEQ ID NO 64
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (11)..(11)
<223> OTHER INFORMATION: X indicates S or A
<220> FEATURE:
<221> NAME/KEY: misc_feature
<222> LOCATION: (12)..(12)
<223> OTHER INFORMATION: Xaa can be any naturally occurring amino acid

<400> SEQUENCE: 64

Met Leu Val Leu Ala Val Thr Gly Ala Phe Leu Xaa Leu Tyr Phe Asp
1               5                   10                  15
Leu

<210> SEQ ID NO 65
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: X indicates  E or A

<400> SEQUENCE: 65

Met Leu Val Leu Ala Val Thr Gly Ala Phe Leu Ala Leu Tyr Phe Xaa
1               5                   10                  15
Leu

<210> SEQ ID NO 66
<211> LENGTH: 17
<212> TYPE: PRT
<213> ORGANISM: Artificial Sequence
<220> FEATURE:
<223> OTHER INFORMATION: synthetic peptide

<400> SEQUENCE: 66

Ile Leu Val Leu Ala Val Thr Gly Ala Phe Leu Ala Leu Tyr Phe Asp
1               5                   10                  15

Leu

<210> SEQ ID NO 67
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (15)..(15)
<223> OTHER INFORMATION: X indicates  E or A

<400> SEQUENCE: 67

Leu Val Leu Ala Val Thr Gly Ala Phe Leu Cys Leu Tyr Phe Xaa Leu
1               5                   10                  15

Pro

<210> SEQ ID NO 68
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (11)..(11)
<223> OTHER INFORMATION: X indicates S or A

<400> SEQUENCE: 68

Leu Val Leu Ala Val Thr Gly Ala Phe Leu Xaa Leu Tyr Phe Asp Leu
1               5                   10                  15

Pro

<210> SEQ ID NO 69
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: X indicates S or A

<400> SEQUENCE: 69

Gly Ala Phe Leu Xaa Leu Tyr Phe Asp Leu Pro Trp Tyr Val Arg Met
1               5                   10                  15

Leu

<210> SEQ ID NO 70
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: X indicates  E or A

<400> SEQUENCE: 70

Gly Ala Phe Leu Cys Leu Tyr Phe Xaa Leu Pro Trp Tyr Val Arg Met
1               5                   10                  15

Leu

<210> SEQ ID NO 71
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (15)..(15)
<223> OTHER INFORMATION: x is K or A

<400> SEQUENCE: 71

Gly Ala Phe Leu Cys Leu Tyr Phe Asp Leu Pro Trp Tyr Val Xaa Met
1               5                   10                  15

Leu

<210> SEQ ID NO 72
<211> LENGTH: 17
<212> TYPE: PRT
<213> ORGANISM: Artificial Sequence
<220> FEATURE:
<223> OTHER INFORMATION: synthetic peptide

<400> SEQUENCE: 72

Gly Ala Phe Leu Cys Leu Tyr Phe Asp Leu Pro Trp Tyr Val Arg Ile
1               5                   10                  15

Leu

<210> SEQ ID NO 73
<211> LENGTH: 18
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: X represents F or A
<220> FEATURE:
<221> NAME/KEY: MISC_FEATURE
<222> LOCATION: (14)..(14)
<223> OTHER INFORMATION: X represents F or A

<400> SEQUENCE: 73

Val Val Ser Val Val Ala Val Leu Val Tyr Lys Xaa Tyr Xaa His Leu
1               5                   10                  15

Met Leu

<210> SEQ ID NO 74
<211> LENGTH: 18
<212> TYPE: PRT
<213> ORGANISM: Artificial Sequence
<220> FEATURE:
<223> OTHER INFORMATION: synthetic peptide

<400> SEQUENCE: 74

Thr Ile Gly Ala Thr Met Leu Val Leu Ala Val Thr Val Thr Ala Leu
1               5                   10                  15

Cys Ile

<210> SEQ ID NO 75
<211> LENGTH: 21
<212> TYPE: PRT
<213> ORGANISM: Artificial Sequence

```
<220> FEATURE:
<223> OTHER INFORMATION: synthetic peptide

<400> SEQUENCE: 75

Lys Lys Leu Leu Ile Val Thr Ile Val Ala Thr Met Leu Val Leu Ala
1               5                   10                  15

Val Thr Val Lys Lys
            20

<210> SEQ ID NO 76
<211> LENGTH: 22
<212> TYPE: PRT
<213> ORGANISM: Artificial Sequence
<220> FEATURE:
<223> OTHER INFORMATION: synthetic peptide

<400> SEQUENCE: 76

Lys Lys Ala Leu Val Ser Gly Met Cys Cys Ala Leu Phe Leu Leu Ile
1               5                   10                  15

Leu Leu Thr Gly Lys Lys
            20

<210> SEQ ID NO 77
<211> LENGTH: 22
<212> TYPE: PRT
<213> ORGANISM: Artificial Sequence
<220> FEATURE:
<223> OTHER INFORMATION: synthetic peptide

<400> SEQUENCE: 77

Lys Lys Leu Leu Thr Val Thr Ile Gly Ala Thr Met Leu Val Leu Ala
1               5                   10                  15

Val Thr Gly Ala Lys Lys
            20

<210> SEQ ID NO 78
<211> LENGTH: 22
<212> TYPE: PRT
<213> ORGANISM: Artificial Sequence
<220> FEATURE:
<223> OTHER INFORMATION: synthetic peptide

<400> SEQUENCE: 78

Lys Lys Ala Leu Val Ser Gly Val Cys Cys Ala Leu Leu Leu Leu Ile
1               5                   10                  15

Leu Leu Val Gly Lys Lys
            20

<210> SEQ ID NO 79
<211> LENGTH: 23
<212> TYPE: PRT
<213> ORGANISM: Artificial Sequence
<220> FEATURE:
<223> OTHER INFORMATION: synthetic peptide

<400> SEQUENCE: 79

Lys Lys Leu Ala Val Thr Val Thr Ser Leu Cys Ile Tyr Leu Asp Leu
1               5                   10                  15

Pro Trp Tyr Leu Arg Lys Lys
            20

<210> SEQ ID NO 80
<211> LENGTH: 20
<212> TYPE: PRT
```

```
<213> ORGANISM: Artificial Sequence
<220> FEATURE:
<223> OTHER INFORMATION: synthetic peptide

<400> SEQUENCE: 80

Lys Lys Leu Ile Leu Leu Thr Gly Val Leu Cys His Arg Phe His Gly
1               5                   10                  15

Leu Trp Lys Lys
            20

<210> SEQ ID NO 81
<211> LENGTH: 20
<212> TYPE: PRT
<213> ORGANISM: Artificial Sequence
<220> FEATURE:
<223> OTHER INFORMATION: synthetic peptide

<400> SEQUENCE: 81

Lys Lys Leu Ala Val Thr Gly Ala Phe Leu Cys Leu Tyr Phe Asp Leu
1               5                   10                  15

Pro Trp Lys Lys
            20

<210> SEQ ID NO 82
<211> LENGTH: 20
<212> TYPE: PRT
<213> ORGANISM: Artificial Sequence
<220> FEATURE:
<223> OTHER INFORMATION: synthetic peptide

<400> SEQUENCE: 82

Lys Lys Leu Ile Leu Leu Val Gly Ala Leu Cys His His Phe His Gly
1               5                   10                  15

Leu Trp Lys Lys
            20

<210> SEQ ID NO 83
<211> LENGTH: 20
<212> TYPE: PRT
<213> ORGANISM: Artificial Sequence
<220> FEATURE:
<223> OTHER INFORMATION: synthetic peptide

<400> SEQUENCE: 83

Lys Lys Leu Ala Val Thr Gly Ala Phe Leu Ala Leu Tyr Phe Asp Leu
1               5                   10                  15

Pro Trp Lys Lys
            20

<210> SEQ ID NO 84
<211> LENGTH: 20
<212> TYPE: PRT
<213> ORGANISM: Artificial Sequence
<220> FEATURE:
<223> OTHER INFORMATION: synthetic peptide

<400> SEQUENCE: 84

Lys Lys Leu Ala Val Thr Gly Ala Phe Leu Ala Leu Tyr Phe Ala Leu
1               5                   10                  15

Pro Trp Lys Lys
            20

<210> SEQ ID NO 85
<211> LENGTH: 20
```

```
<212> TYPE: PRT
<213> ORGANISM: Artificial Sequence
<220> FEATURE:
<223> OTHER INFORMATION: synthetic peptide

<400> SEQUENCE: 85

Lys Lys Leu Ala Val Thr Gly Ala Phe Leu Ala Ser Tyr Phe Asp Leu
1               5                   10                  15

Pro Trp Lys Lys
            20

<210> SEQ ID NO 86
<211> LENGTH: 20
<212> TYPE: PRT
<213> ORGANISM: Artificial Sequence
<220> FEATURE:
<223> OTHER INFORMATION: synthetic peptide

<400> SEQUENCE: 86

Lys Lys Leu Ile Leu Leu Val Gly Ala Leu Ala His His Phe His Gly
1               5                   10                  15

Leu Trp Lys Lys
            20

<210> SEQ ID NO 87
<211> LENGTH: 20
<212> TYPE: PRT
<213> ORGANISM: Artificial Sequence
<220> FEATURE:
<223> OTHER INFORMATION: synthetic peptide

<400> SEQUENCE: 87

Lys Lys Leu Ile Leu Leu Val Gly Ala Leu Ala Ala Ala Phe Ala Gly
1               5                   10                  15

Leu Trp Lys Lys
            20

<210> SEQ ID NO 88
<211> LENGTH: 22
<212> TYPE: PRT
<213> ORGANISM: Artificial Sequence
<220> FEATURE:
<223> OTHER INFORMATION: synthetic peptide

<400> SEQUENCE: 88

Lys Lys Ala Leu Val Ser Gly Val Ala Ala Leu Leu Leu Leu Leu Ile
1               5                   10                  15

Leu Leu Val Gly Lys Lys
            20

<210> SEQ ID NO 89
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (8)..(8)
<223> OTHER INFORMATION: X indicates R,K,H,A
<220> FEATURE:
<221> NAME/KEY: MISC_FEATURE
<222> LOCATION: (12)..(12)
<223> OTHER INFORMATION: X indicates R,K,H,A

<400> SEQUENCE: 89
```

```
Lys Lys Ala Phe Leu Ile Tyr Xaa Phe Tyr Phe Xaa Leu Ile
1               5                   10
```

<210> SEQ ID NO 90
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: X indicates  S or A

<400> SEQUENCE: 90

```
Tyr His Phe Tyr Phe His Leu Ile Leu Ile Ala Gly Xaa Ser Lys Lys
1               5                   10                  15
```

<210> SEQ ID NO 91
<211> LENGTH: 22
<212> TYPE: PRT
<213> ORGANISM: Artificial Sequence
<220> FEATURE:
<223> OTHER INFORMATION: synthetic peptide

<400> SEQUENCE: 91

```
Lys Lys Ser Glu Leu Ser Cys Asn Ile Thr Leu Leu Ile Val Thr Ile
1               5                   10                  15

Gly Ala Thr Met Lys Lys
            20
```

<210> SEQ ID NO 92
<211> LENGTH: 21
<212> TYPE: PRT
<213> ORGANISM: Artificial Sequence
<220> FEATURE:
<223> OTHER INFORMATION: synthetic peptide

<400> SEQUENCE: 92

```
Lys Lys Leu Leu Ala Val Ala Ile Gly Ala Ala Met Leu Val Leu Ala
1               5                   10                  15

Val Ala Gly Lys Lys
            20
```

<210> SEQ ID NO 93
<211> LENGTH: 19
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (11)..(11)
<223> OTHER INFORMATION: X indicates C, S or A

<400> SEQUENCE: 93

```
Lys Lys Leu Ala Val Thr Gly Ala Phe Leu Xaa Leu Tyr Asp Leu Pro
1               5                   10                  15

Trp Lys Lys
```

<210> SEQ ID NO 94
<211> LENGTH: 19
<212> TYPE: PRT
<213> ORGANISM: Artificial Sequence
<220> FEATURE:
<223> OTHER INFORMATION: synthetic peptide
<220> FEATURE:

```
<221> NAME/KEY: MISC_FEATURE
<222> LOCATION: (14)..(14)
<223> OTHER INFORMATION: X indicates D, E or A

<400> SEQUENCE: 94

Lys Lys Leu Ala Val Thr Gly Ala Phe Leu Cys Leu Tyr Xaa Leu Pro
1               5                   10                  15

Trp Lys Lys

<210> SEQ ID NO 95
<211> LENGTH: 14
<212> TYPE: PRT
<213> ORGANISM: Artificial Sequence
<220> FEATURE:
<223> OTHER INFORMATION: synthetic peptide

<400> SEQUENCE: 95

Lys Lys Ala Phe Leu Ile Tyr His Phe Tyr Phe His Leu Ile
1               5                   10

<210> SEQ ID NO 96
<211> LENGTH: 21
<212> TYPE: PRT
<213> ORGANISM: Artificial Sequence
<220> FEATURE:
<223> OTHER INFORMATION: synthetic peptide

<400> SEQUENCE: 96

Lys Lys Leu Leu Thr Val Thr Ile Gly Ala Thr Met Leu Val Leu Ala
1               5                   10                  15

Val Thr Gly Lys Lys
            20

<210> SEQ ID NO 97
<211> LENGTH: 20
<212> TYPE: PRT
<213> ORGANISM: Artificial Sequence
<220> FEATURE:
<223> OTHER INFORMATION: synthetic peptide

<400> SEQUENCE: 97

Lys Leu Leu Thr Val Thr Ile Gly Ala Thr Met Leu Val Leu Ala Val
1               5                   10                  15

Thr Gly Lys Lys
            20

<210> SEQ ID NO 98
<211> LENGTH: 25
<212> TYPE: PRT
<213> ORGANISM: Artificial Sequence
<220> FEATURE:
<223> OTHER INFORMATION: synthetic peptide

<400> SEQUENCE: 98

Lys Lys Thr Ile Ile Gly Val Ser Val Leu Ser Val Leu Val Val Ser
1               5                   10                  15

Val Val Ala Val Leu Val Tyr Lys Lys
            20                  25

<210> SEQ ID NO 99
<211> LENGTH: 21
<212> TYPE: PRT
<213> ORGANISM: Artificial Sequence
<220> FEATURE:
<223> OTHER INFORMATION: synthetic peptide
```

```
<400> SEQUENCE: 99

Lys Lys Val Ser Val Leu Ser Val Leu Val Ser Val Val Ala Val
1               5                   10                  15

Leu Val Tyr Lys Lys
            20

<210> SEQ ID NO 100
<211> LENGTH: 24
<212> TYPE: PRT
<213> ORGANISM: Artificial Sequence
<220> FEATURE:
<223> OTHER INFORMATION: synthetic peptide

<400> SEQUENCE: 100

Lys Lys Val Leu Val Val Ser Val Val Ala Val Leu Val Tyr Lys Phe
1               5                   10                  15

Tyr Phe His Leu Met Leu Lys Lys
            20

<210> SEQ ID NO 101
<211> LENGTH: 20
<212> TYPE: PRT
<213> ORGANISM: Artificial Sequence
<220> FEATURE:
<223> OTHER INFORMATION: synthetic peptide

<400> SEQUENCE: 101

Lys Lys Ala Val Thr Val Thr Ser Leu Cys Ile Tyr Leu Asp Leu Pro
1               5                   10                  15

Trp Tyr Lys Lys
            20

<210> SEQ ID NO 102
<211> LENGTH: 21
<212> TYPE: PRT
<213> ORGANISM: Artificial Sequence
<220> FEATURE:
<223> OTHER INFORMATION: synthetic peptide

<400> SEQUENCE: 102

Lys Lys Leu Ile Val Thr Ile Gly Ala Thr Met Leu Val Leu Ala Val
1               5                   10                  15

Thr Val Thr Lys Lys
            20

<210> SEQ ID NO 103
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: X is S or A
<220> FEATURE:
<221> NAME/KEY: misc_feature
<222> LOCATION: (7)..(7)
<223> OTHER INFORMATION: X is S or A
<220> FEATURE:
<221> NAME/KEY: misc_feature
<222> LOCATION: (12)..(12)
<223> OTHER INFORMATION: X is S or A

<400> SEQUENCE: 103
```

```
Lys Lys Val Xaa Val Leu Xaa Val Leu Val Val Xaa Val Val Ala Val
1               5                   10                  15

Leu Val Tyr Lys Lys
            20
```

<210> SEQ ID NO 104
<211> LENGTH: 21
<212> TYPE: PRT
<213> ORGANISM: Artificial Sequence
<220> FEATURE:
<223> OTHER INFORMATION: synthetic peptide

<400> SEQUENCE: 104

```
Lys Lys Val Ser Val Leu Ser Val Leu Val Val Ser Val Val Ala Val
1               5                   10                  15

Leu Val Ala Lys Lys
            20
```

<210> SEQ ID NO 105
<211> LENGTH: 22
<212> TYPE: PRT
<213> ORGANISM: Artificial Sequence
<220> FEATURE:
<223> OTHER INFORMATION: synthetic peptide

<400> SEQUENCE: 105

```
Lys Lys Val Val Ala Val Val Ala Val Leu Val Tyr Lys Phe Tyr Phe
1               5                   10                  15

His Leu Met Leu Lys Lys
            20
```

<210> SEQ ID NO 106
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (12)..(12)
<223> OTHER INFORMATION: X represents Y or A
<220> FEATURE:
<221> NAME/KEY: MISC_FEATURE
<222> LOCATION: (15)..(15)
<223> OTHER INFORMATION: X represents Y or A

<400> SEQUENCE: 106

```
Lys Lys Val Val Ser Val Val Ala Val Leu Val Xaa Lys Phe Xaa Phe
1               5                   10                  15

His Leu Met Leu Lys Lys
            20
```

<210> SEQ ID NO 107
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (13)..(13)
<223> OTHER INFORMATION: X represents H, K, R or A
<220> FEATURE:
<221> NAME/KEY: MISC_FEATURE
<222> LOCATION: (17)..(17)
<223> OTHER INFORMATION: X represents H, K, R or A

<400> SEQUENCE: 107

-continued

Lys Lys Val Val Ser Val Ala Val Leu Val Tyr Xaa Phe Tyr Phe
1               5                   10                  15

Xaa Leu Met Leu Lys Lys
            20

<210> SEQ ID NO 108
<211> LENGTH: 22
<212> TYPE: PRT
<213> ORGANISM: Artificial Sequence
<220> FEATURE:
<223> OTHER INFORMATION: synthetic peptide

<400> SEQUENCE: 108

Lys Lys Ser Glu Leu Ser Cys Asn Ile Thr Leu Leu Ile Val Thr Ile
1               5                   10                  15

Gly Ala Thr Met Lys Lys
            20

<210> SEQ ID NO 109
<211> LENGTH: 22
<212> TYPE: PRT
<213> ORGANISM: Artificial Sequence
<220> FEATURE:
<223> OTHER INFORMATION: synthetic peptide

<400> SEQUENCE: 109

Lys Lys Val Leu Ala Val Thr Val Thr Ser Leu Cys Ile Tyr Leu Asp
1               5                   10                  15

Leu Pro Trp Tyr Lys Lys
            20

<210> SEQ ID NO 110
<211> LENGTH: 22
<212> TYPE: PRT
<213> ORGANISM: Artificial Sequence
<220> FEATURE:
<223> OTHER INFORMATION: synthetic peptide

<400> SEQUENCE: 110

Lys Lys Ser Glu Leu Ser Ala Asn Ile Thr Leu Leu Ile Val Thr Ile
1               5                   10                  15

Gly Ala Thr Met Lys Lys
            20

<210> SEQ ID NO 111
<211> LENGTH: 24
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: X represents S or A
<220> FEATURE:
<221> NAME/KEY: MISC_FEATURE
<222> LOCATION: (6)..(6)
<223> OTHER INFORMATION: X represents S or A

<400> SEQUENCE: 111

Lys Lys Xaa Glu Leu Xaa Cys Asn Ile Thr Leu Leu Ile Val Thr Ile
1               5                   10                  15

Gly Ala Thr Met Leu Val Lys Lys
            20

<210> SEQ ID NO 112
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (4)..(4)
<223> OTHER INFORMATION: X represents D or E or A

<400> SEQUENCE: 112

Lys Lys Ser Xaa Leu Ser Cys Asn Ile Thr Leu Leu Ile Val Thr Ile
1               5                   10                  15

Gly Ala Thr Met Lys Lys
            20

<210> SEQ ID NO 113
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (10)..(10)
<223> OTHER INFORMATION: X represents T or A
<220> FEATURE:
<221> NAME/KEY: MISC_FEATURE
<222> LOCATION: (15)..(15)
<223> OTHER INFORMATION: X represents T or A
<220> FEATURE:
<221> NAME/KEY: MISC_FEATURE
<222> LOCATION: (19)..(19)
<223> OTHER INFORMATION: X represents T or A

<400> SEQUENCE: 113

Lys Lys Ser Glu Leu Ser Cys Asn Ile Xaa Leu Leu Ile Val Xaa Ile
1               5                   10                  15

Gly Ala Xaa Met Lys Lys
            20

<210> SEQ ID NO 114
<211> LENGTH: 22
<212> TYPE: PRT
<213> ORGANISM: Artificial Sequence
<220> FEATURE:
<223> OTHER INFORMATION: synthetic peptide

<400> SEQUENCE: 114

Lys Lys Ser Glu Leu Ser Cys Asn Ile Thr Leu Leu Ile Val Thr Ile
1               5                   10                  15

Gly Ala Thr Ala Lys Lys
            20

<210> SEQ ID NO 115
<211> LENGTH: 22
<212> TYPE: PRT
<213> ORGANISM: Artificial Sequence
<220> FEATURE:
<223> OTHER INFORMATION: synthetic peptide

<400> SEQUENCE: 115

Lys Lys Val Leu Ala Val Thr Val Thr Ser Leu Ala Ile Tyr Leu Asp
1               5                   10                  15

Leu Pro Trp Tyr Lys Lys
            20

```
<210> SEQ ID NO 116
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (16)..(16)
<223> OTHER INFORMATION: X represents A or D or E

<400> SEQUENCE: 116

Lys Lys Val Leu Ala Val Thr Val Thr Ser Leu Cys Ile Tyr Leu Xaa
1               5                   10                  15

Leu Pro Trp Tyr Lys Lys
            20

<210> SEQ ID NO 117
<211> LENGTH: 22
<212> TYPE: PRT
<213> ORGANISM: Artificial Sequence
<220> FEATURE:
<223> OTHER INFORMATION: synthetic peptide

<400> SEQUENCE: 117

Lys Lys Val Leu Ala Val Thr Val Thr Ser Leu Cys Ile Tyr Leu Asp
1               5                   10                  15

Leu Ala Trp Tyr Lys Lys
            20

<210> SEQ ID NO 118
<211> LENGTH: 22
<212> TYPE: PRT
<213> ORGANISM: Artificial Sequence
<220> FEATURE:
<223> OTHER INFORMATION: synthetic peptide

<400> SEQUENCE: 118

Lys Lys Val Leu Ala Val Thr Val Thr Ala Leu Cys Ile Tyr Leu Asp
1               5                   10                  15

Leu Pro Trp Tyr Lys Lys
            20

<210> SEQ ID NO 119
<211> LENGTH: 22
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: X represents A or T
<220> FEATURE:
<221> NAME/KEY: MISC_FEATURE
<222> LOCATION: (9)..(9)
<223> OTHER INFORMATION: X represents A or T

<400> SEQUENCE: 119

Lys Lys Val Leu Ala Val Xaa Val Xaa Ser Leu Cys Ile Tyr Leu Asp
1               5                   10                  15

Leu Pro Trp Tyr Lys Lys
            20

<210> SEQ ID NO 120
```

```
<211> LENGTH: 22
<212> TYPE: PRT
<213> ORGANISM: Artificial Sequence
<220> FEATURE:
<223> OTHER INFORMATION: synthetic peptide

<400> SEQUENCE: 120

Lys Lys Val Leu Ala Val Thr Val Thr Ser Leu Cys Ile Tyr Leu Asp
1               5                   10                  15

Leu Pro Ala Tyr Lys Lys
            20

<210> SEQ ID NO 121
<211> LENGTH: 22
<212> TYPE: PRT
<213> ORGANISM: Artificial Sequence
<220> FEATURE:
<223> OTHER INFORMATION: synthetic peptide

<400> SEQUENCE: 121

Lys Lys Val Leu Ala Val Thr Val Thr Ser Leu Cys Ile Tyr Leu Asp
1               5                   10                  15

Leu Pro Trp Ala Lys Lys
            20

<210> SEQ ID NO 122
<211> LENGTH: 14
<212> TYPE: PRT
<213> ORGANISM: Artificial Sequence
<220> FEATURE:
<223> OTHER INFORMATION: synthetic peptide

<400> SEQUENCE: 122

Lys Lys Ser Val Ile Val Val Ser Thr Val Ala Phe Leu Ile
1               5                   10

<210> SEQ ID NO 123
<211> LENGTH: 9
<212> TYPE: PRT
<213> ORGANISM: Artificial Sequence
<220> FEATURE:
<223> OTHER INFORMATION: synthetic peptide

<400> SEQUENCE: 123

Gly Leu Arg Ile Leu Leu Leu Lys Val
1               5
```

PEPTIDES BASED ON THE TRANSMEMBRANE DOMAIN OF A TOLL-LIKE RECEPTOR (TLR) FOR TREATMENT OF TLR-MEDIATED DISEASES

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 14680676_1.TXT, the date of creation of the ASCII text file is Jan. 16, 2013, and the size of the ASCII text file is approximately 39 KB.

FIELD OF THE INVENTION

The present invention is in the field of immunotherapy and particularly relates to inhibition of Toll-like receptor (TLR) activation by peptides originated from the transmembrane domain of TLRs.

BACKGROUND OF THE INVENTION

The innate immune response is a complex and highly regulated process. The goal of this system is to provide a broad spectrum and rapid host protection from invading pathogens, as well as to facilitate the activation and further development of the acquired immune response. In recent years, a large body of evidence has indicated that the family of Toll-like receptors (TLRs) plays a critical role in the activation of the innate and the inflammatory response (Foster et al., 2009; Mitchell et al., 2007; O'Neill et al., 2003).

TLRs are a family of conserved transmembrane receptors composed of an extracellular, a single transmembrane, and a cytoplasmic Toll-interleukin1 receptor-resistance (TIR) domain. These receptors recognize a wide variety of ligands, named pathogen-associated molecular patterns (PAMPs) such as lipopolysaccharide (LPS) from gram-negative bacteria, lipoteichoic acid (LTA) from gram-positive bacteria and flagellin, as well as many other compounds. TLRs also help the innate immune system to identify necrotic events, which result in the clearance of various "contaminations" from the surroundings (damage associated molecular pattern molecules, DAMPs). Many tumor cells undergo necrosis mediated by the immune system and may lead to further activation of an inflammation response via TLRs.

Upon binding to their specific PAMP these receptors can either form homodimers, such as in the case of TLR4, or heterodimers as in the case of TLR2 with TLR1 and TLR6. For example, LTA causes a hetero-dimerization of TLR2 with TLRs 1 or 6, and LPS (as a complex with the protein MD2), causes TLR4 homo-dimerization (Ozinsky et al., 2000; Hajjar et al., 2001; Lee et al., 2003; Jin et al., 2007). This triggers a down-stream signaling cascade, resulting in the activation of the NFκB and other survival pathways such as P38 and JNK. One of the main products of TLR activation is the secretion of TNFα, a major proinflammatory cytokine that has many roles in the progression of the inflammatory process. TLR over-expression or over-activation is associated with a variety of diseases e.g. systemic inflammatory response syndrome (SIRS), organ failure, exacerbation of latent or active viral infections (e.g., infection with HIV, cytomegaloviruses, herpes simplex, and influenza virus), inborn or acquired predisposition to pulmonary bacterial infection, congestive heart failure with pulmonary edema, chronic obstructive pulmonary disease, multiple myeloma, SLE, lupus, ulcerative colitis, Crohn's disease, autoimmune diseases such as multiple sclerosis, rheumatoid diseases, chronic hepatitis, malaria (P. Falciparum), neuritis, viral encephalitis (West Nile), candidiasis, atherosclerosis, degenerative diseases, neurodegenerative diseases, and various types of cancer. In extreme cases, severe unregulated activation of the inflammatory process might lead to septic shock, organ failure and death (Foster et al., 2009; Meng et al., 2004).

Attempts to regulate over expression or over activation of TLRs include mainly the use of TLR antagonists. US 2010/062026 discloses agents with poly TLR antagonistic activity (mycobacterium) useful in management of diseases wherein TLRs are over expressed. WO 2009/019260 discloses a method for reducing the biological activities of TLR2 in ischemia reperfusion injury, using TLR2 antagonists. WO 2009/047791 discloses novel synthetic TLR antagonist, potentially useful in the treatment of inflammation, autoimmunity, allergy, asthma, graft rejection, graft versus host disease, infection, sepsis, cancer and immunodeficiency. U.S. Pat. No. 7,410,975 discloses a method for modulating signaling through TLRs using small molecule TLR antagonists. US 2006/0211752 discloses a method of treating a TLR-mediated disease or disorder using methimazole (thyroid hormone antagonist) derivatives and/or cyclic thione derivatives.

Inflammation has been linked to cancer formation and progression and has been studied extensively during the past decade. In colon cancer, inflammation caused by H. pylori has been shown to lead to the formation of many mutations in colon cells including the expression of oncogenes and down regulation of tumor suppressor genes. Other cancers include: hepatocellular carcinoma (HCC) via inflammation induced by hepatitis B virus (HBV), gastric cancer, and lung cancer.

Indeed, TLRs have been demonstrated to be expressed and activated in various solid tumors but mostly not on normal cells in these organs. In addition, there are differences in the array of TLRs identified in different types of tumors (Sato et al., 2009). Overall, these findings suggest that the tumor has a selective mechanism by which it "decides" what type of TLR array will be expressed. The expression and activation of the various TLRs modulate the microenvironment of the tumor and protect it from clearance by the immune system.

To date most studies on prostate cancer were focused on TLR4 and TLR9 which are related to the two main types of infections, bacterial and viral, identified in prostate samples. TLR4 recognizes components from gram-negative bacteria and TLR9 recognizes single stranded DNA from viruses (Huang et al., 2005). Importantly, down regulation of the expression of these proteins leads to a decrease in prostate tumor growth, metastasis formation and mortality in mice (Kundu et al., 2008). However, these studies used siRNA technology which, although highly effective in-vitro, is difficult to apply in-vivo.

WO 03/045431 discloses methods for treating cancer using a combination of a tumor-derived dendritic cell inhibitory factor antagonist, namely a IL-10 or IL-10R antibody, and a TLR9 agonist.

Recent studies demonstrated a significant number of incidences of infection by gram-positive bacteria in prostate sections derived from prostatectomy patients at various stages of the disease (Saenz-Abad et al., 2008; Sfanos et al., 2008). Therefore we hypothesize that TLRs 1, 2, and 6 that are activated by lipoteichoic acid also play a role in prostate cancer.

As stated above, unregulated TLR activation may lead to neurodegenerative diseases such as Alzheimer's disease (AD), a progressive neurodegenerative disease characterized by neuronal loss, activation of microglia, reactivate astrocytes and accumulation of intracellular and extracellular aggregates. According to the "Amyloid hypothesis", extensive extracellular deposits of fibrillar β amyloid (fAβ) condensed to form senile plaques in the brain which are the leading cause of neurodegeneration in AD. It posits that imbalance in the production and clearance of Aβ leads to an increase in its steady-state levels within the brain over the course of decades, resulting in the complex molecular and cellular changes within the brain that characterize Alzheimer's disease. Aβ is produced by the cleavage of APP (amyloid precursor peptide) by either α or β secretase and subsequently the γ secretase resulting in two major forms being 40 and 42 residues in length. In a normal individual, the majority of the Aβ produced is the 40 amino acid species, whereas 5-15% of the total Aβ forms are Aβ42. However, Aβ42 is more toxic and form more stable fibrils and is thus more related to Alzheimer's disease.

Extensive research has demonstrated the involvement of inflammation in Alzheimer's disease. The principal immune effector cells of the brain are microglia cells that are known to be recruited to sites of fAβ plaques in Alzheimer's disease. These cells showed an activated phenotype and high levels of proliferation when surrounded with fAβ, suggesting the role of those cells in the inflammatory phenotype characterizing Alzheimer's disease. Removal of microglia cells from culture containing mixed brain cell and fAβ almost totally eliminates the toxic effects of fAβ on primary neurons, implying that microglia or their products mediate the neurotoxic effects of fAβ. Although microglia and macrophage cells show a role in the progression of Alzheimer's disease, some aspects of the microglial inflammatory response represent positive influences with respect to Alzheimer's disease pathogenesis, such as phagocytic clearance of Aβ from the brain. However, prolonged damage from microglia-mediated inflammatory response likely exacerbates disease pathogenesis. Moreover, the levels of proinflammatory cytokines depend on the magnitude of plaque existence in the Alzheimer's disease brain.

Some TLRs employ additional co-receptors that assist in pathogen recognition, such as CD14 for TLR4. Recently it was demonstrated that TLR4 mediates extensive neuronal cell death upon LPS treatment in microglia cell culture and more importantly in vivo (Lehnardt et al., 2003). This finding suggesting that TLR4, a receptor so far associated with defense against microorganisms may be relevant in chronic neuroinflammation in Alzheimer's disease. Only recently have TLRs been implicated in microglial activation in Alzheimer's disease and how TLRs function in the inflammatory response in AD is now under active investigation. Using a variety of techniques, CD14 was shown to bind fAβ42. It was further shown that the interaction between fAβ42 and CD14 is 20 times greater than that between CD14 and non fAβ, indicating the importance of the fibrillar structure of Aβ in binding CD 14. TLRs have been shown to have a role in neuronal apoptosis as well. Hippocampal neurons exposed to conditioned media from microglia treated with fAβ resulted in neuronal death. However, media from CD14$^{-/-}$ or TLR4$^{-/-}$ microglia cells treated with fAβ were unable to kill neurons (Fassbender et al., 2004 and Walter et al., 2007). These data suggest that CD14 and TLR4 function in the production of neurotoxic molecules. Moreover, it was recently found that neurons express several TLRs and that TLR4 expression increase in neurons when exposed to fAβ, leading to neuronal apoptosis. This finding suggests that neurons expressing TLR4 are vulnerable to degeneration in AD (Sung-Chun et al., 2008).

SUMMARY OF THE INVENTION

It has now been found in accordance with the present invention that synthetic peptides based on the sequence of the transmembrane domain of a Toll-like Receptor (TLR), optionally further comprising the sequence of the cytoplasmic region or analogs thereof, are capable of modulating the activity of a TLR protein in response to ligand activation The present invention thus relates, in one aspect, to a synthetic peptide of at least 4 and at most 30 amino acid residues selected from the group consisting of:

(a) a peptide capable of inhibiting cell activation mediated by a Toll-like receptor (TLR) selected from TLR 1, 2, 4 or 6, said peptide comprising a sequence consisting of, or found within the sequence of the transmembrane domain of a TLR selected from TLR 1, 2, 4 or 6;

(b) a peptide of (a) linked via its α-amino group or α-carboxyl group to a further oligopeptide comprising a sequence of the cytoplasmic region or extracellular region adjacent to said transmembrane domain;

(c) an analog of the peptide of (a) or (b);

(d) a salt or a chemical derivative of a peptide of (a), (b) or (c);

(e) a peptide of (a) to (d) further comprising one or more positively charged amino acid residues at each of the N- and C-termini; and (f) a cyclic derivative of a peptide of (a) to (d).

Similarly, the peptide of the present invention is capable of inhibiting hetero-dimerization or homo-dimerization of Toll-like receptor (TLR) molecules selected from TLR 1, 2, 4 or 6.

The phrase "the cytoplasmic region or extracellular region adjacent to said transmembrane domain in a TLR" refers to regions corresponding to the cytoplasmic region or extracellular region adjacent to said transmembrane domain in a native TLR molecule of the respective TLR. For example, a peptide comprising a transmembrane domain of TLR1, or a part of it, may further comprise an extracellular or intracellular peptide corresponding to a region which in a native TLR1 is adjacent to the said transmembrane region. The phrase "the sequence found within the sequence of the transmembrane domain of a TLR" refers to a partial transmembrane domain peptide having a C-terminal or N-terminal sequence of the transmembrane domain. In case the partial sequence is of the C-terminus of the transmembrane domain, it is linked via its α-carboxyl group, and is immediately adjacent, to a sequence corresponding to the intracellular region adjacent to the C-terminus of the transmembrane domain in the intact wild-type TLR. In case the partial sequence is of the N-terminus of the transmembrane domain, it is linked via its α-amino group, and is immediately adjacent, to a sequence corresponding to the extracellular region adjacent to the N-terminus of the transmembrane domain in the intact wild-type TLR.

Non-limiting examples of cells, which activation is mediated by TLR, are immune cells such as macrophages, dendritic cells and microglia cells; neurons and tumor cells.

As used herein, the term "cell activation mediated by TLR" refers to the conversion of a relatively quiescent cell to a relatively more active cell effected by the binding of a TLR ligand to a TLR and the consequent transmission of a signal via a TLR signal-transduction pathway that results in the activation of the cell as measured for example by, but not limited to, the secretion of pro-inflammatory cytokines such as, but not limited to, TNF-α, IL-1b, and IL-6 from cells.

Methods for measuring cell activation mediated by TLRs are well known in the art. One non-limiting example, which is commonly used to assess TLR-mediated cell activation, is to follow the secretion of pro-inflammatory cytokines such as, but not limited to, TNF-α, IL-1b, and IL-6 from cells. This can be done for example by ELISA as described in "Materials & Methods" herein below. Another non-limiting example of a method for measuring cell activation mediated by TLRs is to follow changes in the activation state of NF-κB in cells transfected with a NF-κB reporter vector as described for example in "Materials & Methods" herein below.

Methods for measuring hetero- and homo-dimerization are well known in the art. Some non-limiting examples, which are commonly used to assess peptide-dimerization, is Fluorescence Resonance Energy Transfer (FRET) for Fluorescein and Rhodamine (TAMRA) labeled peptides (other commercially available fluorophores can be used), membrane binding assays using 4-fluoro-7-nitro-[2,1,3]-benzoxadiazole (NBD; Apollo)-labeled peptide, or co-immunoprecipitation assays as described for example in "Materials & Methods" herein below In another aspect, the present invention is related to a nucleic acid sequence comprising a nucleotide sequence encoding for the synthetic peptide of the invention.

In yet another aspect, the present invention relates to a pharmaceutical composition comprising at least one synthetic peptide according to the invention, and a pharmaceutically acceptable carrier. According to certain embodiments, the pharmaceutical composition is for the treatment of a TLR-mediated disease.

In another aspect, the present invention is related to the use of the synthetic peptide of the invention, for the treatment of a TLR-mediated disease.

In yet another aspect, the present invention relates to a method for the treatment of a TLR-mediated disease, comprising administering to a patient suffering from said TLR-mediated disease an effective amount of the synthetic peptide of the invention, optionally with a pharmaceutically acceptable carrier.

In some embodiments, the TLR-mediated disease is acute inflammation such as septic shock or cancer such as prostate cancer.

TM C'-CtoA (SEQ ID NO:86) are capable to self assemble in solution, to a very slight extent (7A). mTLR2 TM N'-CtoA (SEQ ID NO:88) highly oligomerise in solution (black line, 7B) and is partially dissociated in the presence of LUVs (gray line, 7B). (7C-7D) In the presence of LUVs, both mTLR1 TM N' and mTLR1 TM C' are capable to self assemble, whereas mTLR2 TM N' and mTLR2 TM C' do not change before and after the addition of LUVs to the system (7C). LL37 is shown as an example for a peptide that is highly oligomerised in liposomes (7D).

Figure 8:
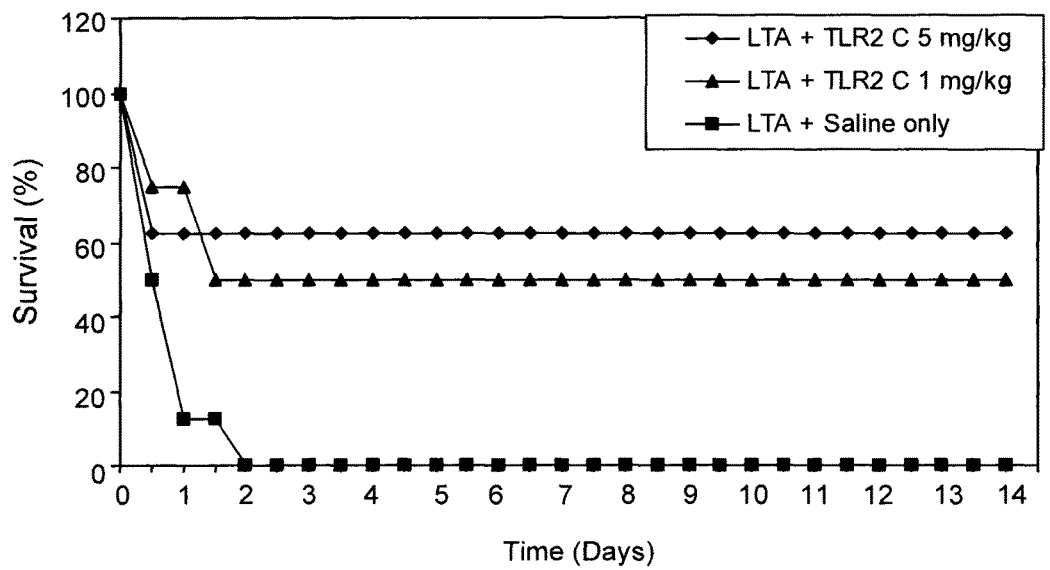

FIG. 8 shows that mTLR2 TM C'-CtoA (SEQ ID NO:86) is able to inhibit TLR2 activation in-vivo. Mice were treated with a single i.p. injection of LTA, then injected with mTLR2 TM C'-CtoA (SEQ ID NO:86) at the indicated concentrations or left untreated (saline only, black squares). A second injection was given 2 hours (1 mg/kg, black rectangles) or 12 hours later (5 mg/kg, black diamonds). Survival was monitored for the next 14 days. Survival of the untreated mice dropped to 0 after 48 hours, while 5 mg/kg of mTLR2 TM C'-CtoA (SEQ ID NO:86) was able to rescue up to 62.5% of the mice with no noticeable adverse effects. n=8 for all groups.

Figure 9:
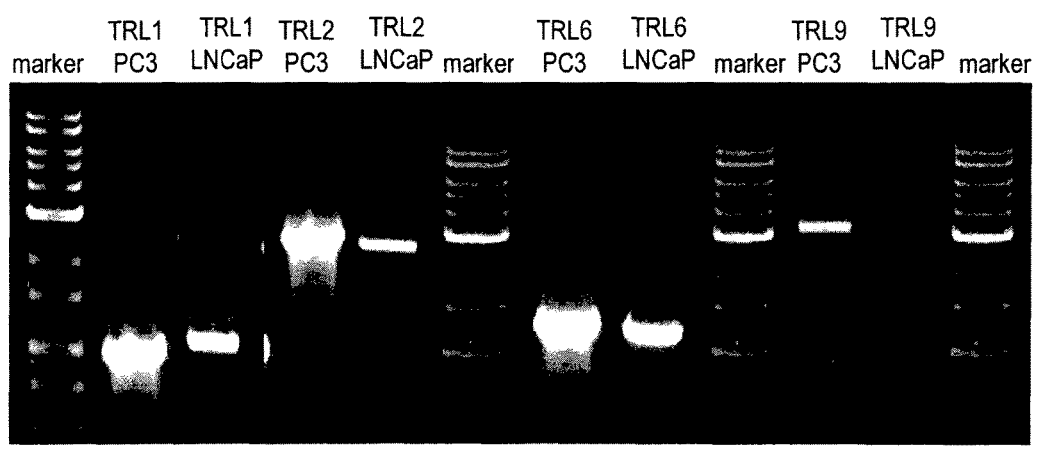

FIG. 9 shows mRNA expression of the various TLR transcripts (TLR 1, 2 and 6) in two different prostate cancer cell lines PC3 and LNCaP. It is clear that a difference in the expression of the transcripts exists between the cell lines. PC3 is the only cell line expressing all tested TLR transcripts.

Figure 10:
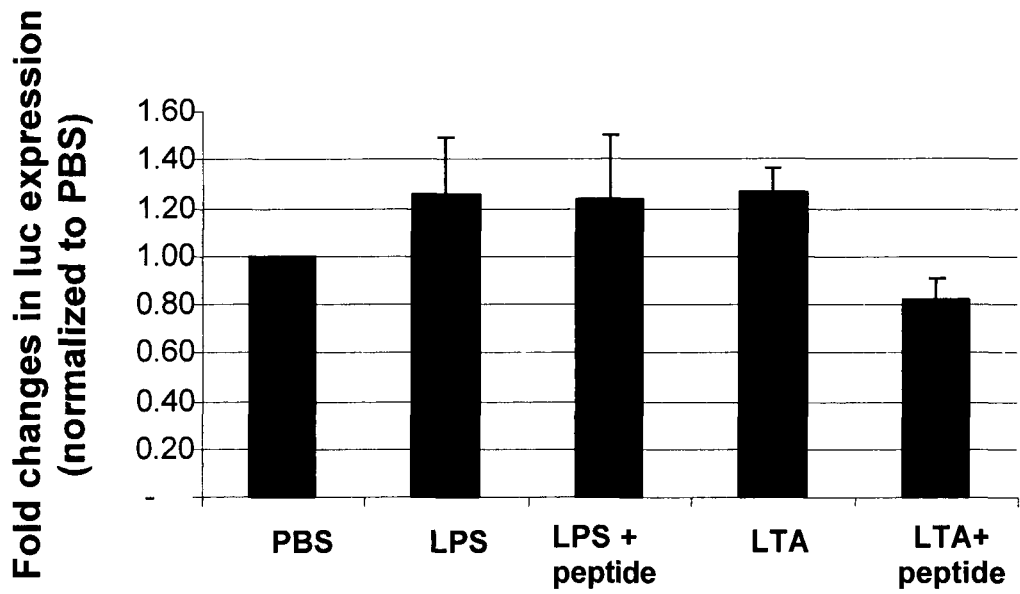

FIG. 10 shows NFkB activation in PC3 cells and its specific inhibition with the peptide hTLR2 TM C' (SEQ ID NO:83). Cells were transfected with a luciferase plasmid under the transcriptional control of NFkB. Upon activation, NFkB trans-locates to the nucleus and induces the expression of luciferase. Cells were activated in the presence of LTA (50 μg/ml) or LPS (1 μg/ml) for 24 hours and were incubated for 2 hours with the hTLR2 TM C' peptide (SEQ ID NO:83) (20 μm) prior to the addition of the activator and washed twice with PBS. Detection of Luc expression was performed by the Steady-Glo assay kit.

Figure 11:
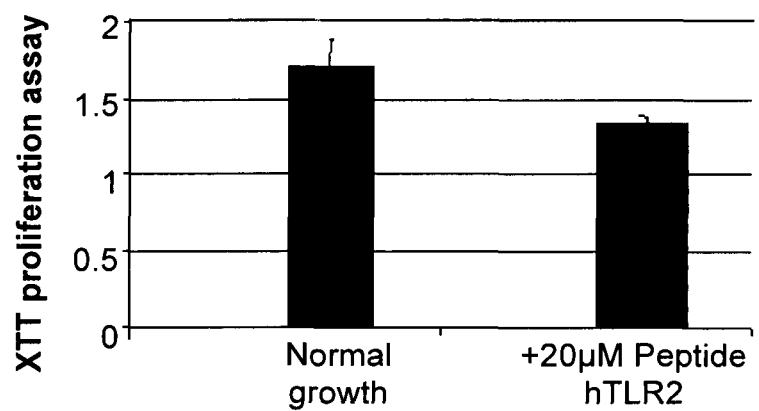

FIG. 11 shows an evaluation of the influence of the peptide on the growth rate of PC3 cells. Cells were grown for 72 hours in the presence of the peptide hTLR2 TM C' (SEQ ID NO:83) while every 24 hours medium was changed and a fresh peptide was added. For the control cells, PBS was added.

Figure 12A:
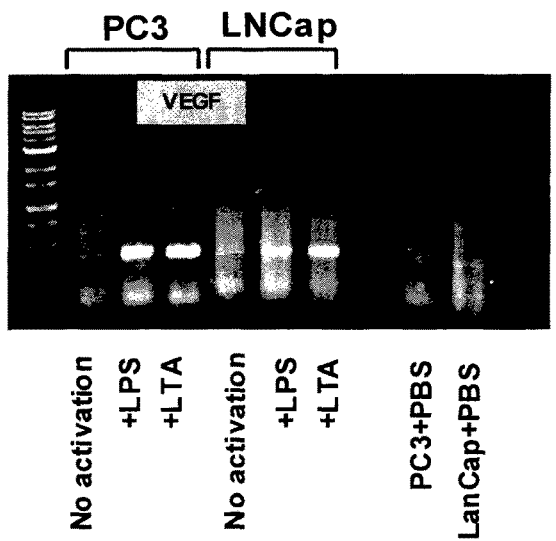
Figure 12B:
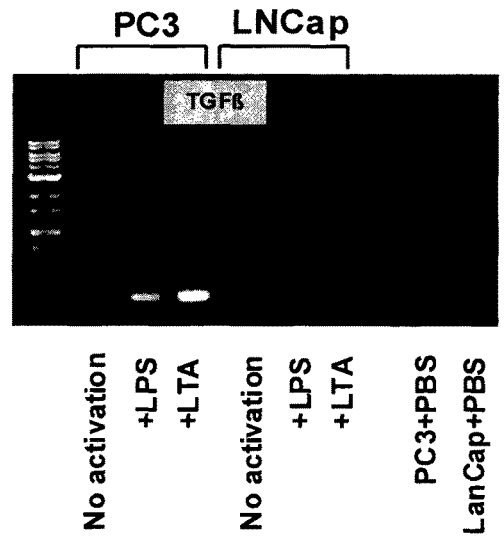

FIGS. 12A-B show mRNA expression of TGFβ (B) and VEGF (A) in LNCaP and PC3 cells in the absence or presence of LPS/LTA.

Figure 13A:
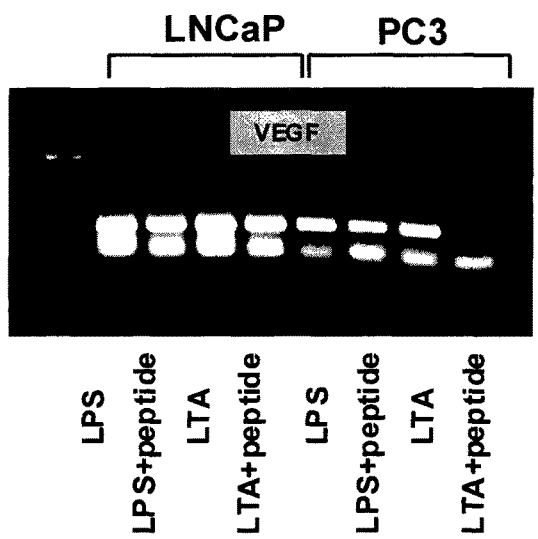
Figure 13B:
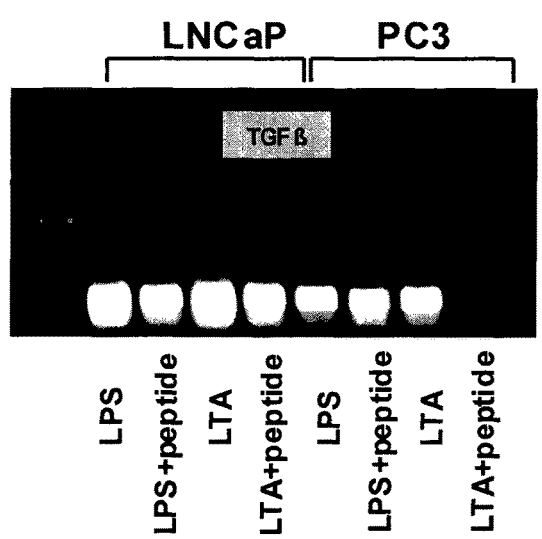

FIGS. 13A-B show mRNA expression of TGFβ (B) and VEGF (A) in LNCaP and PC3 cells in the absence or presence of LPS/LTA and the peptide hTLR2 TM C' (SEQ ID NO:83) at a concentration of 20 μM.

Figure 14:
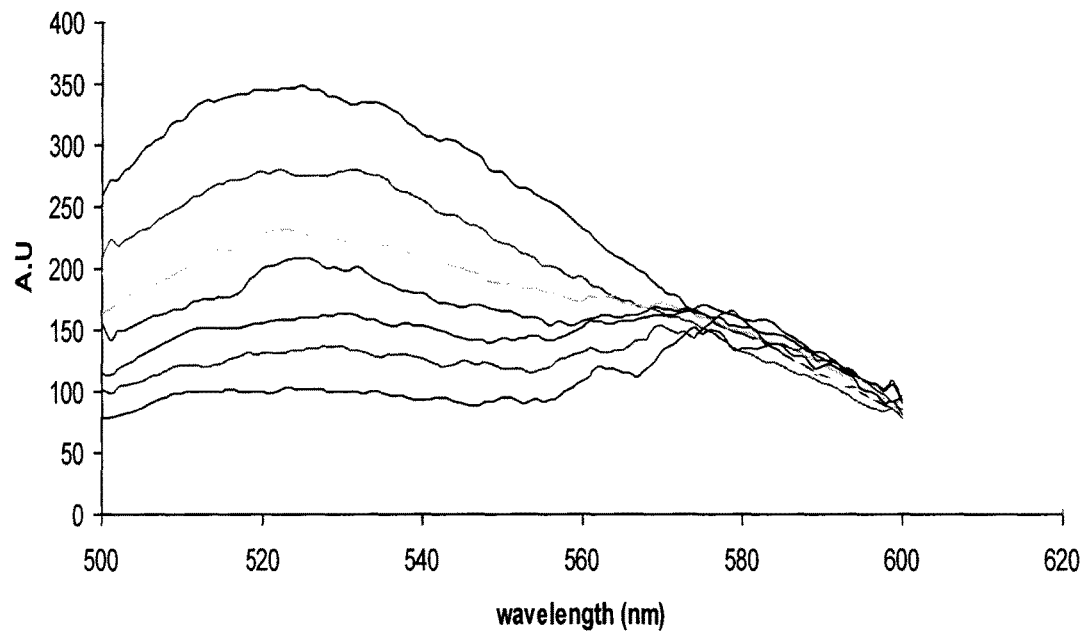

FIG. 14 depicts FRET between TLR6 C9 TMD (SEQ ID NO: 85) and TLR4 C11 TMD (SEQ ID NO: 95). The TLR4 peptide was labeled with NBD (donor) and loaded on PC:Cholesterol LUVs. Changes in the intensity of the emission signal were monitored between 500 to 600 nm, upon the addition of successive amounts of rhodamine-labeled TLR6 C TM. Peptides concentrations used are (from top to bottom) 0 μM. 0.0125 μM, 0.025 μM, 0.05 μM, 0.1 μM, 0.2 μM, 0.4 μM and 0.8 μM. Donor peptide concentrations used are 0.4 μM.

Figure 15:
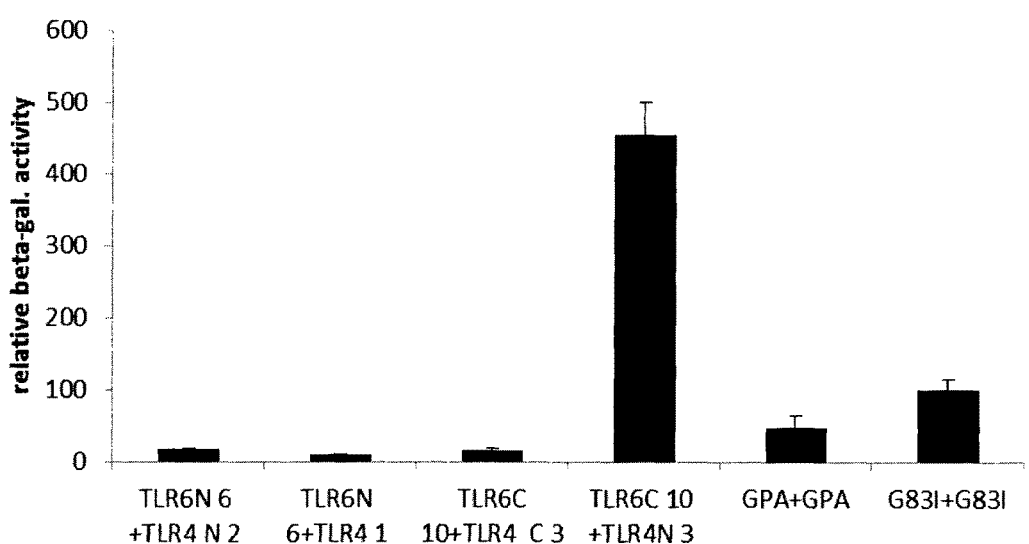

FIG. 15 shows hetero-dimerization of TLR4 and TLR6 TMD peptides in the membrane of living cells as measured using the GALLEX assay. The activities are shown relative to the strain expressing the G83I chimera from both plasmids TLR6 N6 (SEQ ID NO: 96); TLR6 C10 (SEQ ID NO: 94); TLR4 C3 (SEQ ID NO:122).

Figure 16:
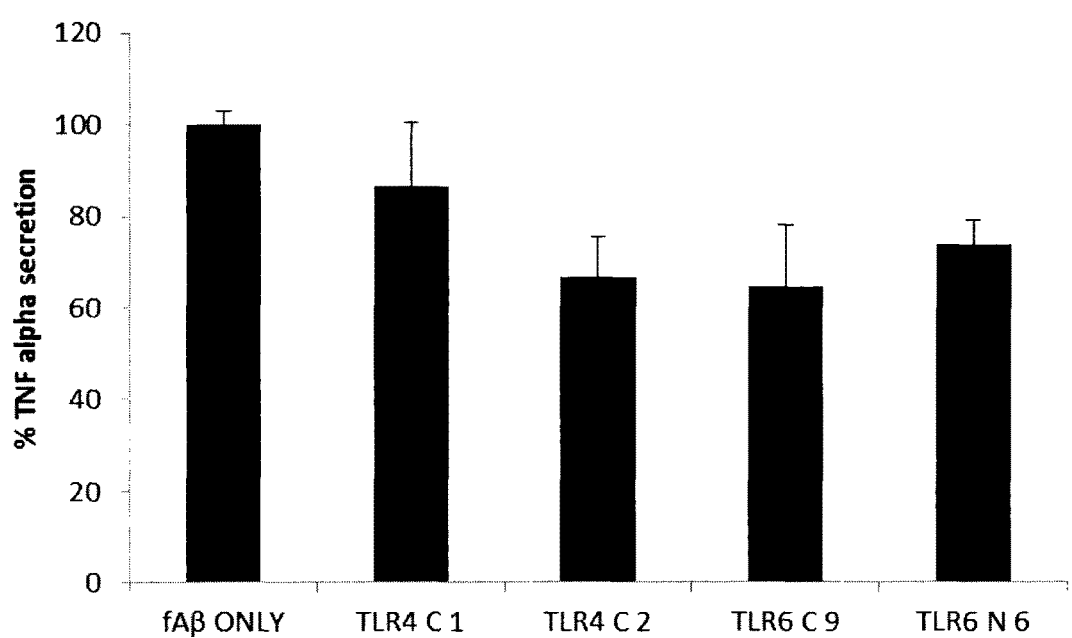

FIG. 16 depicts the effect of TLR4 and TLR6 TMD peptides on TNFα secretion by macrophage RAW264.7 cells. Cells were incubated for 2 hours with 20 μM of the indicated peptides then washed and stimulated with fibrillar β amyloid (fAβ) for 24 h (final concentration 10 μM). TNFα levels in supernatant were assessed by ELISA. TLR TLR4 C1 (SEQ ID NO: 95); TLR 4 C2 (SEQ ID NO:90); TLR6 C9 (SEQ ID NO:83); TLR6 N6 (SEQ ID NO:96).

DETAILED DESCRIPTION OF THE INVENTION

Since their discovery in humans in the late 1990's, Toll-like receptors (TLRs) were shown in numerous studies to be essential for the initiation and progression of the innate immune response. These receptors were also shown to be of major importance in many other physiological processes such as lipid metabolism, cancer progression and neurogenesis (Huang et al., 2007; Rolls et al., 2007; Shi et al., 2006). As a consequence of their essential role in so many different processes, their mode of action and regulation was extensively studied, concentrating on both the cytoplasmic tails as well as the extracellular stalks.

Despite the extensive work done on both the extracellular and cytoplasmic domains of the different TLRs, to date, almost no work has been done on the transmembrane regions of these proteins. However, during the last two decades, there has been extensive evidence indicating that the transmembrane domains of membrane proteins play a major role in their activation and regulation. Recent studies have shown that the TM domains of several TLRs and their flanking hydrophobic regions might be involved in their trafficking and activation (Kajita et al., 2006; Nishiya et al., 2006).

Figure 1A:
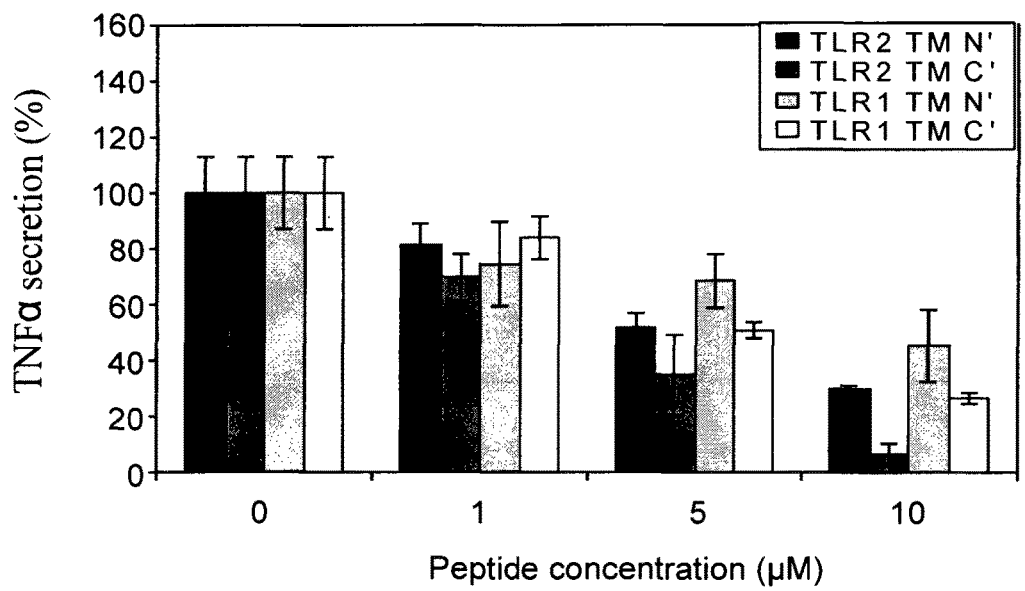
FIGS. 1A-1D show that the effect of peptides based on the transmembrane domain of TLR1 and TLR2 on TNFα secretion by RAW264.7 cells, is pathogen-associated molecular pattern (PAMP) dependent. (1A-1B) Cells were incubated for 2 hours with different concentrations of the indicated transmembrane (TM) peptides mTLR2 TM N'-CtoA (SEQ ID NO:88), mTLR2 TM C'-CtoA (SEQ ID NO:86), mTLR1 TM N' (SEQ ID NO:77) and mTLR1 TM C'-CtoA (SEQ ID NO:83) then washed and stimulated with low lipoteichoic acid (LTA) concentrations (100 ng/ml, 1A) or lipopolysaccharide (LPS, 10 ng/ml, 1B). (1C-1D) cells were incubated with 20 µM of the indicated peptides then stimulated with high LTA concentration (500 ng/ml, 1C) or LPS (10 ng/ml, 1D). TNFα levels in the supernatant after 5 hours of stimulation were assessed by ELISA.
Figure 1B:
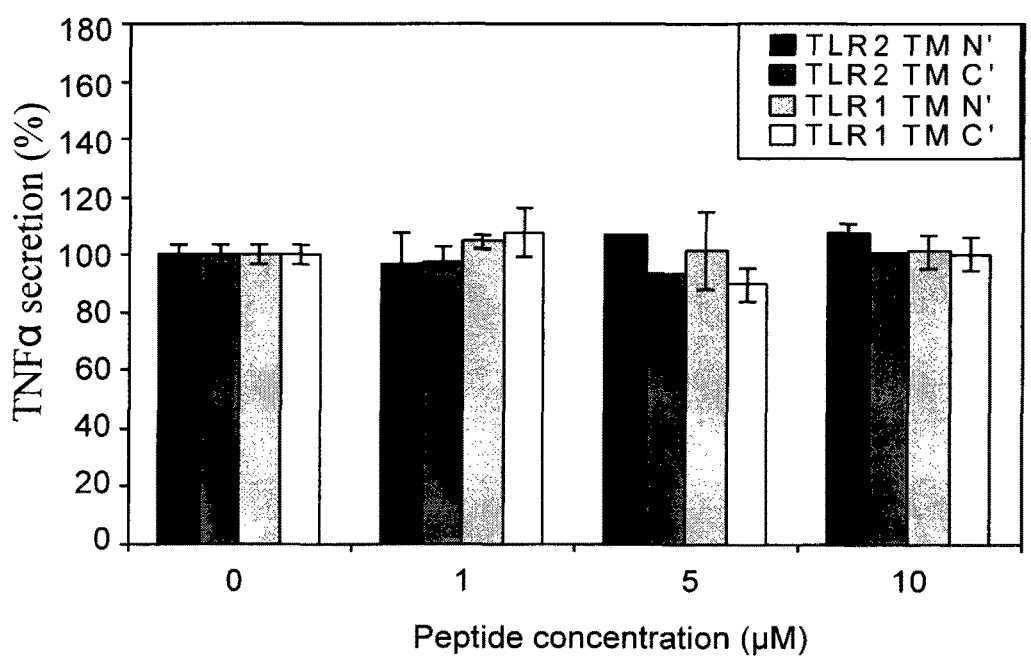
Figure 1C:
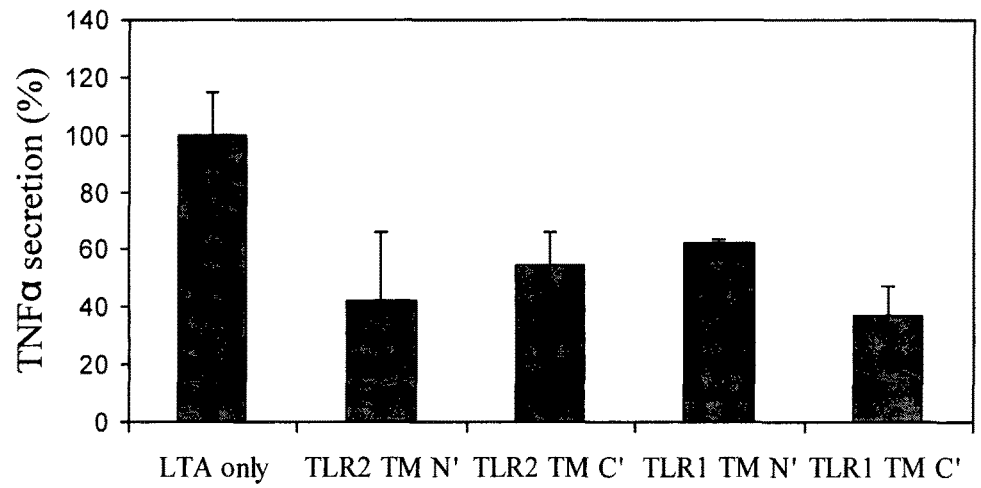
Figure 1D:
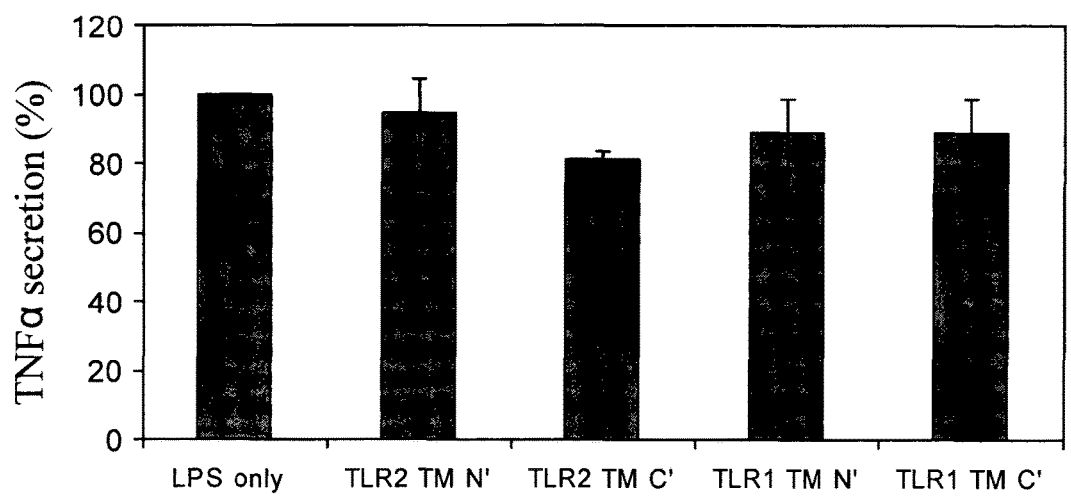

In accordance with the present invention we provide evidence showing that the transmembrane (TM) domains of TLR1/6 and TLR2 are involved in the activation and regulation of these receptors. Exogenous peptides corresponding to the N-terminus or the extended C-terminus of these regions were able to inhibit the secretion of TNFα by RAW264.7 macrophages in response to LTA stimulation (FIGS. 1A and 1C). This inhibition was specific to TLR2, as these peptides did not affect the secretion of TNFα in response to LPS, a TLR4 activator (FIGS. 1B and 1D). These peptides were shown to be relatively non-toxic to RAW264.7 macrophages under our experimental conditions, exhibiting LC50's of over 50 μM for all peptides (Table 1).

Interactions between the peptides were also seen in PC:Cholesterol large unilamellar vesicles (LUVs), which constitute a lipid environment commonly used to mimic the eukaryotic membrane. TLR1 TM peptides were shown to be able to form heterodimers as well as homodimers with TLR2 TM, with higher propensity towards heterodimers (FIGS. 2A-2C and 3A-3C). In both cases fluorescence resonance energy transfer (FRET) intensity was higher than that observed for Cp, an unrelated TM peptide (the core TM peptide of TCRα).

Figure 5A:
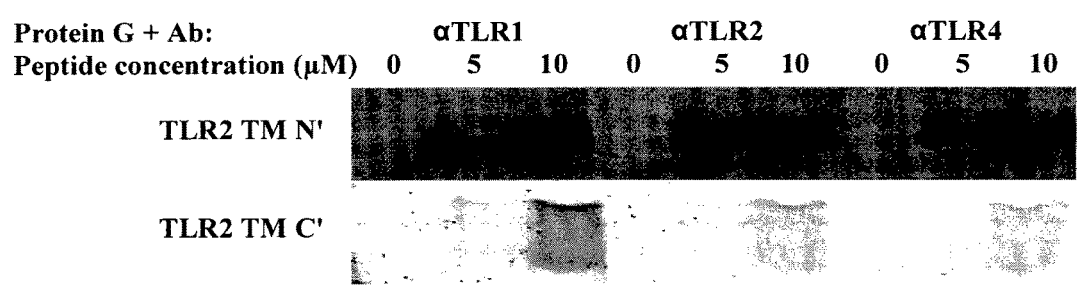
FIGS. 5A-5B show that peptides based on the transmembrane domain of TLR2 are able to physically interact with TLR1 protein rather than with other TLRs. (5A) RAW264.7 macrophage cells were incubated with rhodamine labeled peptides mTLR2 TM N'-CtoA (SEQ ID NO:88) and mTLR2 TM C'-CtoA (SEQ ID NO:86) at the indicated concentrations. The cells with the peptide were washed and lysed, the soluble fraction was used for co-immunoprecipitation (co-IP) with different TLR antibodies. Protein samples were run on SDS-PAGE and the presence of the labeled peptide was detected with a fluorescent scanner (Excitation-532 nm, emission-585 nm). (5B) Protein samples were analyzed by western blot for the detection of specific TLR proteins and complexes, with specific antibodies, as indicated (αTLR1, 2 and 4).
Figure 5B:
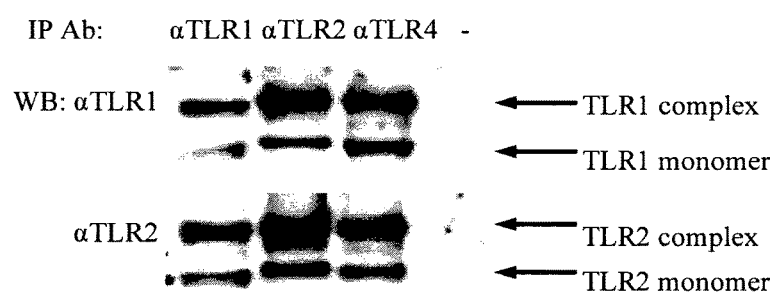

To support these findings, co-immunoprecipitation (co-IP) was used to show that peptides based on the TM domain of TLR2 can physically interact with TLR1 protein, and that TLR1, 2 and 4 are able to interact with each other (FIGS. 5A and 5B, respectively).

Examining the ability of these peptides to form oligomers supported our FRET observations and indicated that TLR1

Figure 7A:
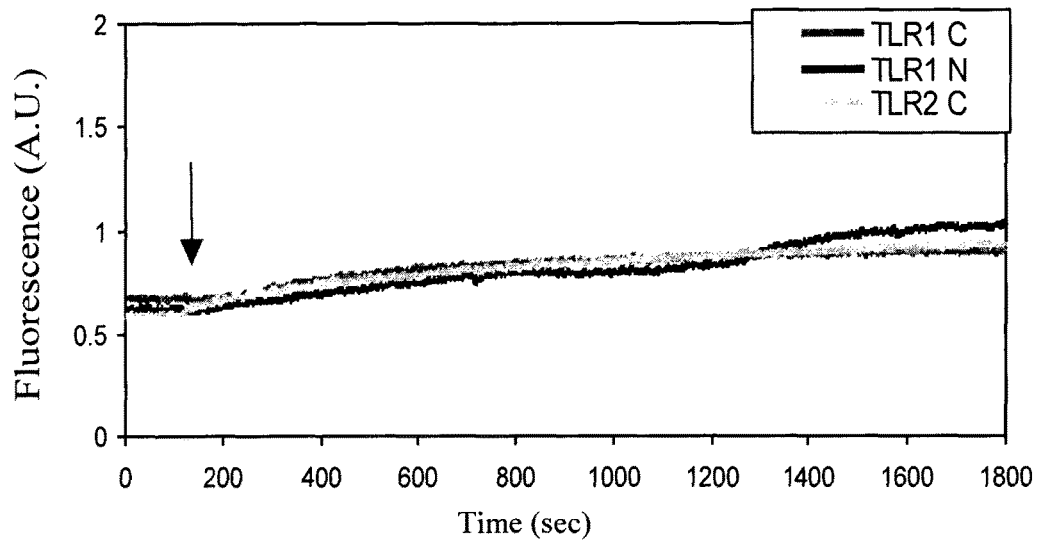
FIGS. 7A-7D show that peptides based on the transmembrane domain of TLR1 and TLR2 differ in their ability to self assemble both in buffer and in PC:Cholesterol LUVs. (7A-7B) Rhodamine conjugated TLR peptides mTLR2 TM N'-CtoA (SEQ ID NO:88), mTLR2 TM C'-CtoA (SEQ ID NO:86), mTLR1 TM N' (SEQ ID NO:77) and mTLR1 TM C'-CtoA (SEQ ID NO:83), were added to HEPES solution and their emission at 585 nm was recorded before and after the addition of proteinase K. The addition of the proteinase K is indicated by a black arrow. mTLR1 TM C'-CtoA (SEQ ID NO:83), mTLR1 TM N' (SEQ ID NO:77) and mTLR2
Figure 7B:
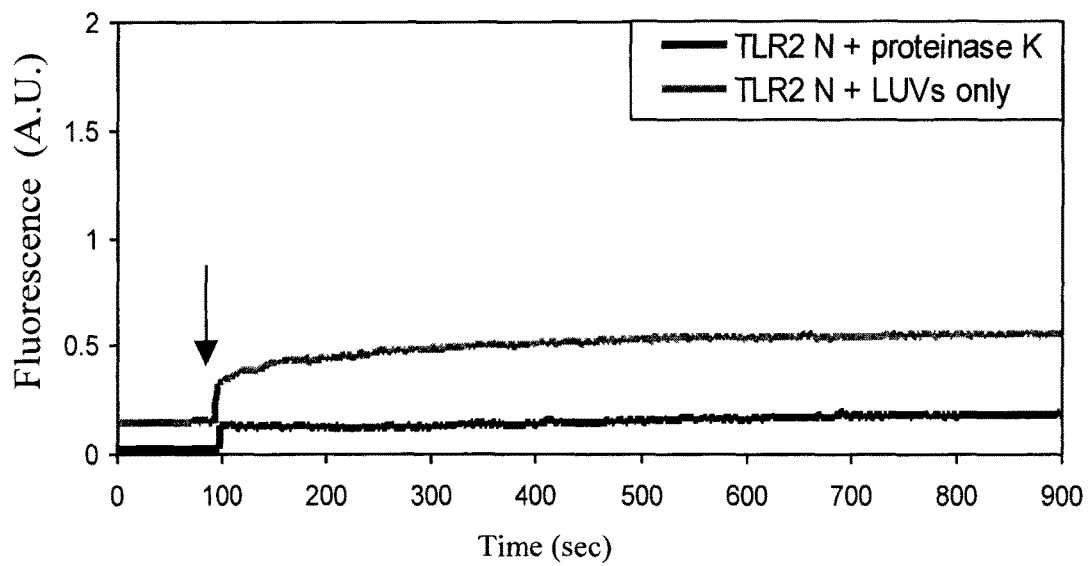

TM peptides were able to form homodimers in LUVs, to a certain extent. Of note, these experiments show that although the TLR2 TM peptide is highly aggregated in solution due to its high hydrophobicity, it is able to dissociate into a monomeric state upon the addition of LUVs to the system (FIGS. 7A-7B).

Additionally, mTLR2 TM C'-CtoA peptide (SEQ ID NO:86) was also shown to inhibit TLR2 activation in-vivo. Using a murine model for acute septic shock caused by LTA, we showed that administration of this peptide was able to rescue more than 60% of the mice in comparison to no survival of untreated mice (FIG. 8). Due to the fact that death was caused by excessive, imbalanced TLR2 activation, mTLR2 TM C'-CtoA peptide is most probably directly involved in inhibiting TLR2 activation in these animals. The finding that death rates were stable from 48 hours after LTA injection and on, suggests that the surviving animals were completely and irreversibly cured with no noticeable adverse effects.

In accordance with the present invention we further provide evidence showing that peptides comprising sequence of the transmembrane (TM) domains of TLR4/6 are capable of forming hetero-dimers and exogenous peptides corresponding to the N-terminus or the C-terminus of TLR6 TM region or peptides corresponding to the C-terminus of TLR4 TM region were able to inhibit the secretion of TNFα by RAW264.7 macrophages in response to fibrillar β-amyloid stimulation (FIG. 16).

When examining mRNA levels of expression of various TLRs in several types of prostate cancer cell lines it was found that both PC3 and DU145 cells (highly metastatic) express almost all tested TLRs, whereas in LNCaP and 22RV1 (low metastatic), only mRNA transcripts of TLR1, 2 and 6 were detected (FIG. 9, data shown only for PC3 and LNCaP cells).

A luciferase (Luc) expression assay in PC3 cells showed that activation with LPS (a TLR4 activator) or LTA (TLR2 activator) resulted in a significant increase in the Luc expression. Addition of human TLR2 TM C' peptide (SEQ ID NO:83) caused a decrease in Luc expression for LTA activation but not for LPS activation (FIG. 10). In addition, incubation of the cells with hTLR2 TM C' peptide (SEQ ID NO:83), caused inhibition in proliferation of PC3 cells (FIG. 11).

The mRNA level of expression of the cytokines TGFβ and VEGF in PC3 cells (highly metastatic) and LNCaP cells (low metastatic) was examined upon activation with LPS and LTA. Interestingly, only PC3 cells showed a marked increase in the mRNA expression of the cytokines upon stimulation (FIG. 12). In addition, a drop in the levels of expression in the presence of the hTLR2 TM C' peptide (SEQ ID NO:83) was observed (FIG. 13).

Taken together, our results demonstrate the ability of peptides based on the TM domains of TLR2, 1 and 6 to inhibit TLR2 activation both in-vitro and in-vivo, to form heterodimers, and to interact with the native receptors. Thus, they constitute strong candidates for therapy in a variety of pathologies where TLR2 inhibition is needed. Our results further demonstrate the ability of peptides based on the TM domains of TLR4 and 6 to inhibit TLR4/6 activation, to form heterodimers, and to interact with the native receptors. These peptides constitute strong candidates for therapy of neurodegeneration caused by fibrillar β-amyloid in Alzheimer's disease.

In addition, our results show a correlation between the level of expression of specific TLR arrays on prostate cancer cell lines, their ability to secrete anti-inflammatory cytokines, and their ability to generate metastases. Thus, the level of expression of specific TLR arrays in certain tumor cells may be used in diagnosis as markers for the aggressiveness of the cancer (i.e. the ability to generate metastases).

In some embodiments, the TLR is a mammalian TLR 1, 2, 4 or 6. In other embodiments the mammalian TLR is human (hTLR) or mouse (*Mus musculus*; mTLR) TLR1, TLR2, TLR4 or TLR6.

In certain embodiments, the synthetic peptide of the invention comprises a sequence consisting of, or found within the sequence of, the transmembrane (TM) domain of a TLR selected from TLR 1, 2, 4 and 6, optionally flanked by an intracellular or an extracellular region, or both, of the corresponding TLR, wherein:

(i) said human TLR1 has a predicted transmembrane domain of the sequence set forth in SEQ ID NO:1 or a sequence comprising said predicted transmembrane domain and its extracellular and cytoplasmic flanking regions set forth in SEQ ID NO:2;

(ii) said human TLR2 has a predicted transmembrane domain of the sequence set forth in SEQ ID NO:3 or a sequence comprising said predicted transmembrane domain and its extracellular and cytoplasmic flanking regions set forth in SEQ ID NO:4;

(iv) said human TLR6 has a predicted transmembrane domain of the sequence set forth in SEQ ID NO:5 or a sequence comprising said predicted transmembrane domain and its extracellular and cytoplasmic flanking regions set forth in SEQ ID NO:6;

(v) said mouse TLR1 has a predicted transmembrane domain of the sequence set forth in SEQ ID NO:7 or a sequence comprising said predicted transmembrane domain and its extracellular and cytoplasmic flanking regions set forth in SEQ ID NO:8;

(vi) said mouse TLR2 has a predicted transmembrane domain of the sequence set forth in SEQ ID NO:9 or a sequence comprising said predicted transmembrane domain and its extracellular and cytoplasmic flanking regions set forth in SEQ ID NO:10;

(viii) said mouse TLR6 has a predicted transmembrane domain of the sequence set forth in SEQ ID NO:11 or a sequence comprising said predicted transmembrane domain and its extracellular and cytoplasmic flanking regions set forth in SEQ ID NO:12;

(ix) said mouse TLR 4 has a predicted transmembrane domain of the sequence set forth in SEQ ID NO:13 or a sequence comprising said predicted transmembrane domain and its extracellular and cytoplasmic flanking regions set forth in SEQ ID NO:14; and (x) said human TLR 4 has a predicted transmembrane domain of the sequence set forth in SEQ ID NO:15 or a sequence comprising said predicted transmembrane domain and its extracellular and cytoplasmic flanking regions set forth in SEQ ID NO:16.

Predicted TM domains were obtained from the UniProt/swissport database, but other (identical or similar) predicted TM domains could have been calculated using any other known algorithm readily available to a person skilled in the art, such as the neural network of Pasquier and Hamodrakas, 1999 (An hierarchical artificial neural network system for the classification of transmembrane proteins. Protein Eng 1999 August; 12(8):631-4). Thus, the disclosed predicted TM domain sequences are possible examples, and should not be construed as limiting the peptides of the present invention to the sequences disclosed. For example, the TM domain predicted using a different algorithm could be displaced by a few amino acids along the amino acid sequence of the TLR polypeptide and could be of a different length.

In certain embodiments the synthetic peptide consists of 16 to 23 amino acid residues found within the predicted transmembrane domain of 21-30 amino acid residues of said human or mouse TLR. In other embodiments the synthetic peptide is selected from the peptides of the sequences set forth in SEQ ID NO:17 to SEQ ID NO:23.

In some embodiments the synthetic peptide consists of 14 to 19 amino acid residues, 4 to 17 of which are found within the predicted transmembrane domain of said human or mouse TLR and 1 to 14, preferably 3 to 9, are found within the cytoplasmic region flanking said transmembrane domain. In other embodiments the synthetic peptide is selected from the peptides of the sequences set forth in SEQ ID NO:24 to SEQ ID NO:43.

As used herein the term "analog" refers to deletion, addition or substitution of one or more amino acid residues. When preparing analogs obtained by substitution of amino acid residues, it is important that the substitutions be selected from those which cumulatively do not substantially change the volume, hydrophobic-hydrophilic pattern and charge of the corresponding portion of the unsubstituted parent peptide. Thus, a hydrophobic residue may be substituted with a hydrophilic residue, or vice-versa, as long as the total effect does not substantially change the volume, hydrophobic-hydrophilic pattern and charge of the corresponding unsubstituted parent peptide, i.e. as long as the TLR binding motif is kept.

Thus, in certain embodiments, the synthetic peptide analog is obtained from the synthetic peptide by deletion, addition or substitution of one or more amino acid residues, preferably by substitution of one to four amino acid residues by alanine. In other embodiments, the synthetic peptide analog consists of 14 to 35, preferably 16, amino acid residues, 6 to 21, preferably 8, of which are found within the predicted transmembrane domain of a human or mouse TLR, and 1 to 14, preferably 8, are found within the flanking cytoplasmic or extracellular region of said transmembrane domain, and one to four amino acid residues of the cytoplasmic region are substituted with alanine, arginine, lysine, histidine or serine; or the peptide analog consists of amino acid residues, preferably 18, within said predicted transmembrane domain, in which one or two amino acid residues are substituted with alanine. Thus, according to certain embodiments, the synthetic peptide has a sequence selected from the sequences of SEQ ID NO:44 to SEQ ID NO:74. In all of these synthetic peptides cysteine residues were mutated to alanines for synthetic ease. This approach is commonly used and is based on the fact the cysteine residues within TM domains usually do not affect the activity of a membrane protein (Frillingos et al., 1998; He et al., 1996).

Also included in the scope of the present invention are D,L-amino acid analogs. These analogs may possess advanced pharmacological properties such as better solubility in water and controlled degradation by proteolytic enzymes.

It should be understood that other modifications of the peptides and analogs thereof are also contemplated by the present invention. Thus, the peptide or analog of the present invention is intended to include a "chemical derivative" thereof which retains at least a portion of the function of the peptide which permits its utility in modulating the activity of a TLR protein in response to ligand activation.

A "chemical derivative" of a peptide or analog of the present invention contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues. Many such chemical derivatives and methods for making them are well known in the art.

In certain embodiments the chemical derivative, is an ester, amide or N-acyl derivative of the synthetic peptide. The N-acyl derivative is optionally an acyl group of a $C_6$-$C_{18}$ carboxylic acid, preferably an acyl group of a saturated or unsaturated $C_6$-$C_{18}$ fatty acid. Examples of fatty acids include but are not limited to hexanoic acid, heptanoic acid, octanoic acid, decanoic acid, undecanoic acid, dodecanoic acid, myristic acid, palmitic acid, palmitoleic acid, trans-hexadecanoic acid, stearic acid, oleic acid, linoleic acid, linolenic acid and elaidic acid. In certain embodiments, the peptide is covalently linked to a nonproteinaceous polymer, such as polyethyleneglycol (PEG) to increase the stability of the peptide and change the rate at which it is eliminated from a subject after administration thereto. The PEG is a substituted or unsubstituted polymer having a molecular weight of from about 1000 to about 5000 Da or more. Other non-limiting examples of such polymers are poly (propyleneglycol), or poly (oxyalkylene).

Also included in the scope of the invention are salts of the peptides and analogs of the invention. As used herein, the term "salts" refers to both salts of carboxyl groups and to acid addition salts of amino groups of the peptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. Such chemical derivatives and salts are preferably used to modify the pharmaceutical properties of the peptide insofar as stability, solubility, etc., are concerned.

In certain embodiments, the positively charged amino acid residues added at each of the N- and C-termini, are selected from lysine, arginine, histidine or ornithine. In other embodiments, one or two, preferably two, lysine residues are added at one or both of the peptide termini, preferably at both termini. The addition of lysine residues at the peptide's termini serves to improve their solubility in physiological fluids. Thus, in preferred embodiments, the synthetic peptide has a sequence selected from: SEQ ID NO:75 to SEQ ID NO:122.

Cyclic peptides can be synthesized by a solid-phase method, with or without cysteine residues at both the N- and C-termini of the peptides. The cyclization without cysteine is carried out by protecting the N-terminal, activating the C-terminal, then deprotecting the N-terminal and reacting the C- and N-terminal groups while still bound to the resin. When the peptide contains cystein residues at both the N- and C-termini, after HF cleavage and RP-HPLC purification, the peptides are solubilized at low concentration in PBS (pH 7.3), and cyclization is completed after 12 h. The cyclic peptides are further purified on RP-HPLC and subjected to amino acid analysis to confirm their composition, and SDS-PAGE to confirm their monomeric state.

In certain embodiments the synthetic peptide of the present invention is capable of inhibiting the activity of a TLR protein in response to ligand activation.

In another aspect, the present invention is related to a nucleic acid sequence comprising a nucleotide sequence encoding for the synthetic peptides of the invention.

In yet another aspect, the present invention relates to a pharmaceutical composition comprising at least one synthetic peptide according to the invention, and a pharmaceutically acceptable carrier. According to certain embodiments, the pharmaceutical composition is for the treatment of a TLR-mediated disease.

In another aspect, the present invention is related to the use of the synthetic peptide of the invention, for the treatment of a TLR-mediated disease.

In yet another aspect, the present invention relates to a method for the treatment of a TLR-mediated disease, comprising administering to a patient suffering from said TLR-mediated disease an effective amount of the synthetic peptide of the invention, optionally with a pharmaceutically acceptable carrier.

In some embodiments, the TLR-mediated disease is acute inflammation such as septic shock or cancer such as prostate cancer. In other embodiments, the TLR-mediated disease is selected from: systemic inflammatory response syndrome (SIRS); acute inflammation (e.g. septic shock, sepsis, endotoxic shock, hemodynamic shock, optic neuritis and sepsis syndrome); post ischemic reperfusion injury, inflammatory bowel diseases (e.g. Crohn's disease and ulcerative colitis); exacerbation of latent or active infections (e.g., infection with HIV, cytomegaloviruses, herpes simplex, influenza virus, malaria, chronic hepatitis, candidiasis, mycobacterial infection, and meningitis); congestive heart failure; autoimmune diseases (e.g. multiple sclerosis, psoriasis, systemic lupus erythematosus); chronic obstructive pulmonary disease; predisposition to pulmonary bacterial infection; congestive heart failure with pulmonary edema; rheumatoid diseases (e.g. rheumatoid arthritis, rheumatoid spondylitis, osteoarthritis, and other arthritic conditions); degenerative diseases (e.g. atherosclerosis), neurodegenerative diseases (e.g. Alzheimer's disease and Parkinson's disease); fibrotic disease; cachexia; graft rejection; radiation damage; asthma and cancer such as gastric carcinoma, colon cancer, hepatocellular carcinoma, epithelial ovarian cancer, cervical squamous cell carcinomas, breast cancer, prostate cancer, lung cancer, melanoma and neuroblastoma.

Any suitable route of administration is encompassed by the invention, including oral, intravenous, subcutaneous, intraarticular, intramuscular, inhalation, intranasal, intrathecal, intraperitoneal, intradermal, transdermal or other known routes, including the enteral route. In preferred embodiments, the peptides or analogs of the invention are administered by oral, intranasal or subcutaneous routes.

The dose ranges for the administration of the compositions of the present invention should be large enough to produce the desired effect, whereby, for example, over expression or over activation of a TLR is regulated, and further, where the disease is significantly treated. The doses should not be so large as to cause adverse side effects, such as unwanted cross reactions, generalized immunosuppression, anaphylactic reactions and the like.

The present invention will now be described in more detail in the following non-limiting Examples and the accompanying figures.

EXAMPLES

In the Examples herein below, the peptides of the invention will be presented by their SEQ ID NOs. Predicted TM domains were obtained from the UniProt/swissport database.

List of Peptides:

```
                                         SEQ ID NO: 1
LLIVTIVATMLVLAVTVTSLC
(predicted-TM human TLR1);

SEQ ID NO: 2
DFHMSELSCNITLLIVTIVATMLVLAVTVTSLCIYLDLPW
(predicted-TM+ flanking regions- human TLR1);

SEQ ID NO: 3
ALVSGMCCALFLLILLTGVLCH
(predicted-TM human TLR2);

SEQ ID NO: 4
DVRLSVSECHRTALVSGMCCALFLLILLTGVLCHRFHGLW
(predicted-TM+ flanking regions- human TLR2);

SEQ ID NO: 5
LLIVTIGATMLVLAVTVTSLC
(predicted-TM human TLR6);

SEQ ID NO: 6
DFHMSELSCNITLLIVTIGATMLVLAVTVTSLCIYLDLPW
(predicted-TM+ flanking regions- human TLR6);

SEQ ID NO: 7
VLLTVTIGATMLVLAVTGAFL
(predicted-TM mouse TLR1);

SEQ ID NO: 8
DFHMSPLSCDTVLLTVTIGATMLVLAVTGAFLCLYFDLPWYVR
(predicted-TM+ flanking regions- mouse TLR1);

SEQ ID NO: 9
AALVSGVCCALLLLILLVGAL
(predicted-TM mouse TLR2);

SEQ ID NO: 10
RLQDARPSVLECHQAALVSGVCCALLLLILLVGALCHHFHGLWYLR
(predicted-TM+ flanking regions- mouse TLR2);

SEQ ID NO: 11
VLLTITIGATMLVLAVTGAFL
(predicted-TM mouse TLR6);

SEQ ID NO: 12
DFHMSPLSCDTVLLTITIGATMLVLAVTGAFLCLYFDLPWYVR
(predicted-TM+ flanking regions- mouse TLR6).

SEQ ID NO: 13
TIISVSVVSVIVVSTVAFLIYHFYFHLILI
(predicted-TM mTLR4)

SEQ ID NO: 14
TIISVSVVSVIVVSTVAFLIYHFYFHLILIAGCKKYSRGESIY
(predicted-TM+ flanking regions- mouse TLR4)

SEQ ID NO: 15
TIIGVSVLSVLVVSVVAVLVY
(predicted-TM hTLR4)

SEQ ID NO: 16
SLNITCQMNKTIIGVSVLSVLVVSVVAVLVYKFYFHLMLL
(predicted-TM+ flanking regions- human TLR4)

SEQ ID NO: 17
LLIVTIVATMLVLAVTV
(predicted N-term-TM hTLR1);

SEQ ID NO: 18
ALVSGMCCALFLLILLTG
(predicted N-term-TM hTLR2);

SEQ ID NO: 19
LLTVTIGATMLVLAVTGA
(predicted N-term-TM mTLR1);
```

-continued

ALVSGVCCALLLLILLVG
(predicted N-term-TM mTLR2);

TIIGVSVLSVLVVSVVAVLVY
(predicted C-term-TM hTLR4);

SEQ ID NO: 21

VSVLSVLVVSVVAVLVY
(predicted C-term-TM hTLR4);

SEQ ID NO: 22

LIVTIGATMLVLAVTVT
(predicted N-term-TM hTLR6);

SEQ ID NO: 23

LAVTVTSLCIYLDLPWYLR
(predicted C-term-TM+Cyto hTLR1);

SEQ ID NO: 24

LILLTGVLCHRFHGLW
(predicted C-term-TM+Cyto hTLR2);

SEQ ID NO: 25

LAVTGAFLCLYFDLPW
(predicted C-term-TM+Cyto mTLR1);

SEQ ID NO: 26

LILLVGALCHHFHGLW
(predicted C-term-TM+Cyto mTLR2);

SEQ ID NO: 27

VVSVVAVLVYKFYFHLML
(predicted C-term-TM and flanking
cytoplasmatic hTLR4);

SEQ ID NO: 28

AFLIYHFYFHLILIAGC
(predicted C-term-TM mTLR4+cyto);

SEQ ID NO: 29

VAFLIYHFYFHLILIAG
(predicted C-term-TM mTLR4+cyto);

SEQ ID NO: 30

HFYFHLILIAGCKKY
(predicted C-term-TM mTLR4+cyto);

SEQ ID NO: 31

SCDTVLLTVTIGATMLV
(predicted N-term-TM mTLR6+extra);

SEQ ID NO: 32

SPLSCDTVLLTVTIGAT
(predicted N-term-TM mTLR6+extra);

SEQ ID NO: 33

TVLLTVTIGATMLVLAV
(predicted N-term-TM mTLR6+extra);

SEQ ID NO: 34

LVLAVTGAFLCLYFDLP
(predicted C-term-TM mTLR6+cyto);

SEQ ID NO: 35

GAFLCLYFDLPWYVRML
(predicted C-term-TM mTLR6+cyto);

SEQ ID NO: 36

TIGATMLVLAVTGAFLC
(predicted C-term-TM mTLR6+cyto);

SEQ ID NO: 37

MLVLAVTGAFLCLYFDL
(predicted C-term-TM mTLR6+cyto);

SEQ ID NO: 38

MLVLAVTGAFLALYFDL
(predicted C-term-TM mTLR6+cyto);

SEQ ID NO: 39

-continued

LVLAVTGAFLCLYFDLP
(predicted C-term-TM mTLR6+cyto);

SEQ ID NO: 40

GAFLCLYFDLPWYVRML
(predicted C-term-TM mTLR6+cyto);

SEQ ID NO: 41

AVTVTSLCIYLDLPWY
(predicted N-term-TM hTLR6 with flannking
cytoplasmatic);

SEQ ID NO: 42

SELSCNITLLIVTIGATM
(predicted N-term-TM hTLR6 with flanking
extracellular);

SEQ ID NO: 43

LAVTGAFLALYFDLPW
(predicted C-term-TM+Cyto mTLR1 with C to
A substitution);

SEQ ID NO: 44

LAVTGAFLALYFALPW
(predicted C-term-TM+Cyto mTLR1 with C to A
and D to A substitutions);

SEQ ID NO: 45

LAVTGAFLASYFDLPW
(predicted C-term-TM+Cyto mTLR1 with C to A
and L605S substitutions);

SEQ ID NO: 46

LILLVGALAHHFHGLW
(predicted C-term-TM+Cyto mTLR2 with C to A
substitution);

SEQ ID NO: 47

LILLVGALAAAFAGLW
(predicted C-term-TM+Cyto mTLR2 with C to A
and 3H to A substitutions)

SEQ ID NO: 48

ALVSGVAAALLLLILLVG
(predicted N-term-TM mTLR2 with C to A
substitution).

SEQ ID NO: 49

AFLIYHFYFHLILIAGAAFLIYHFYFHLILIAGXA
(predicted C-term-TM mTLR4 with X indicates A
or S+cyto);

SEQ ID NO: 50

FLIYXFYFXLILIAGC
(predicted C-term-TM mTLR4 with X indicates R,
K, H or A+cyto);

SEQ ID NO: 51

VAFLIY XFYFXLILIAG
(predicted C-term-TM mTLR4 with X indicates R,
K, H or A+cyto);

SEQ ID NO: 52

XFYFXLILIAGCKKY
(predicted C-term-TM mTLR4 with X indicates R,
K, H or A+cyto);

SEQ ID NO: 53

SADTVLLTVTACDTVLLTVT IGATMLV
(predicted N-term-TM mTLR6 where S is substituted
to A+extra);

SEQ ID NO: 54

SXDTVLLTVT IGATMLV
(predicted N-term-TM mTLR6 with X indicates A or
S+extra);

SEQ ID NO: 55

-continued

SCDAVLLAVA IGAAMLV
(predicted N-term-TM mTLR6 with T to A
substitution+extra);
SEQ ID NO: 56

APLACDTVLLTVTIGAT
(predicted N-term-TM mTLR6 with S to A
substitution+extra);
SEQ ID NO: 57

TVLLTVTIGATILVLAV
(predicted N-term-TM mTLR6 with M to I
substitution+extra);
SEQ ID NO: 58

LVLAVTGAFLXLYFDLP
(predicted C-term-TM mTLR6 with X indicates S
or A+cyto);
SEQ ID NO: 59

LVLAVTGAFLCLYFXLP
(predicted C-term-TM mTLR6 with X indicates E
or A+cyto);
SEQ ID NO: 60

GAFLXLYFDLPWYVRML
(predicted C-term-TM mTLR6 with X indicates S
or A+cyto);
SEQ ID NO: 61

GAFLCLYFDLPWYVRIL
(predicted C-term-TM mTLR6 with M to I
substitution+cyto);
SEQ ID NO: 62

TIGATILVLAVTGAFLC
(predicted C-term-TM mTLR6 with M to I
substitution+cyto);
SEQ ID NO: 63

MLVLAVTGAFLXLYFDL
(predicted C-term-TM mTLR6 with X indicates S
or A+cyto);
SEQ ID NO: 64

MLVLAVTGAFLALYFXL
(predicted C-term-TM mTLR6 with X indicates E
or A+cyto);
SEQ ID NO: 65

ILVLAVTGAFLALYFDL
(predicted C-term-TM mTLR6 with M to I
substitution+cyto);
SEQ ID NO: 66

LVLAVTGAFLCLYFXLP
(predicted C-term-TM mTLR6 with X indicates E
or A+cyto);
SEQ ID NO: 67

LVLAVTGAFLXLYFDLP
(predicted C-term-TM mTLR6 with X indicates S
or A+cyto);
SEQ ID NO: 68

GAFLXLYFDLPWYVRML
(predicted C-term-TM mTLR6 with X indicates S
or A+cyto);
SEQ ID NO: 69

GAFLCLYFXLPWYVRML
(predicted C-term-TM mTLR6 with X indicates E
or A+cyto);
SEQ ID NO: 70

GAFLCLYFDLPWYVXML
(predicted C-term-TM mTLR6 with X indicates K
or A+cyto);
SEQ ID NO: 71

GAFLCLYFDLPWYVRIL
(predicted C-term-TM mTLR6 with M to 1
substitution+cyto);
SEQ ID NO: 72

VVSVVAVLVYKXYXHLML
(predicted C-term-TM hTLR4 and flanking
cytoplasmatic where X represents F or A);
SEQ ID NO: 73

TIGATMLVLAVTVTALCI
(predicted C-term-TM hTLR6 with S substituted
to A);
SEQ ID NO: 74

KKLLIVTIVATMLVLAVTVKK
kk(predicted N-term-TM hTLR1)kk;
SEQ ID NO: 75

KKALVSGMCCALFLLILLTGKK
kk(predicted N-term-TM hTLR2)kk;
SEQ ID NO: 76

KKLLTVTIGATMLVLAVTGAKK
kk(predicted N-term-TM mTLR1)klc;
SEQ ID NO: 77

KKALVSGVCCALLLLILLVGKK
kk(predicted N-term-TM mTLR2)kk;
SEQ ID NO: 78

KKLAVTVTSLCIYLDLPWYLRKK
kk(predicted C-term-TM+C yto hTLR1)kk;
SEQ ID NO: 79

KKLILLTGVLCHRFHGLWKK
kk(predicted C-term-TM+Cyto hTLR2)kk;
SEQ ID NO: 80

KKLAVTGAFLCLYFDLPWKK
kk(predicted C-term-TM+Cyto mouse TLR1)kk;
SEQ ID NO: 81

KKLILLVGALCHEIFHGLWKK
kk(predicted C-term-TM+Cyto mTLR2)kk;
SEQ ID NO: 82

KKLAVTGAFLALYFDLPWKK
kk(predicted C-term-TM+Cyto mTLR1 with C to A
substitution)kk;
SEQ ID NO: 83

KKLAVTGAFLALYFALPWKK
kk(predicted C-term-TM+Cyto mTLR1 with C to
A and D to A substitutions)kk;
SEQ ID NO: 84

KKLAVTGAFLASYFDLPWKK
kk(predicted C-term-TM+Cyto mTLR1 with C to A
and L605S substitutions kk
SEQ ID NO: 85

KKLILLVGALAHHFHGLWKK
kk(predicted C-term-TM+Cyto mTLR2 with C to A
substitution)kk;
SEQ ID NO: 86

KKLILLVGALAAAFAGLWKK
kk(predicted C-term-TM+Cyto mTLR2 with C to A
and 3H to A substitutions)kk;
SEQ ID NO: 87

KKALVSGVAAALLLLILLVGKK
kk(predicted N-term-TM mTLR2 with C to A
substitution)kk;
SEQ ID NO: 88

YHFYFHLILIAGSKK KKAFLI Y XFYFXLI
kk(predicted C-term-TM mTLR4, with X indicates
R, K, H, A);
SEQ ID NO: 89

SEQ ID NO: 90
YHFYFHLILIAGXSKK
(predicted C-term-TM mTLR4 with X indicates S
or A+cyto)kk;

SEQ ID NO: 91
KKAFLIYXFYFXLI
kk(predicted C-term-TM mTLR4, with X indicates
R, K, H, A; C1);

SEQ ID NO: 92
KKLLAVAIGAAMLVLAVAGKK
kk(predicted N-term-TM mTLR6 with T to A
substitution)kk;

SEQ ID NO: 93
KKLAVTGAFLXLYDLPWKK
kk(predicted C-term-TM mTLR6 with X indicates
C, S or A+cyto)kk;

SEQ ID NO: 94
KKLAVTGAFLCLYXLPWKK
kk(predicted C-term-TM mTLR6 with X indicates
D, E or A+cyto)kk;

SEQ ID NO: 95
KKAFLIYHFYFHLI
kk(predicted C-term-TM mTLR4);

SEQ ID NO: 96
KKLLTVTIGATMLVLAVTGKK
kk(predicted N-term-TM mTLR6)kk;

SEQ ID NO: 97
KLLTVT IGATMLVLAV TGKK
k(predicted N-term-TM mTLR6)kk;

SEQ ID NO: 98
KKTIIGVSVLSVLVVSVVAVLVYKK
kk(predicted-TM hTLR4)kk

SEQ ID NO: 99
KKVSVLSVLVVSVVAVLVYKK
kk(predicted C-term-TM hTLR4)kk;

SEQ ID NO: 100
KKVLVVSVVAVLVYKFYFHLMLKK
kk(predicted C-term-TM and flanking cytoplasmatic
hTLR4)kk;

SEQ ID NO: 101
KKAVTVTSLCIYLDLPWYKK
(predicted C-term-TM hTLR6 with flanking
cytoplasmatic)kk SEQ ID NO: 102
KKLIVTIGATMLVLAVTVTKK
kkxxxxxx (predicted N-term-TM hTLR6)kk;

SEQ ID NO: 103
KKVXVLXVLVVXVVAVLVYKK
kk(predicted C-term-TM hTLR4 where X represents
either S or A)kk;

SEQ ID NO: 104
KKVSVLSVLVVSVVAVLVAKK
kk(predicted C-term-TM hTLR4 with Y substituted
to A; C5)kk);

SEQ ID NO: 105
KKVVAVVAVLVYKFYFHLMLKK
kk(predicted C-term-TM hTLR4 and flanking
cytoplasmatic where S is substituted to A)kk;

SEQ ID NO: 106
KKVVSVVAVLVXKFXFHLMLKK
(predicted C-term-TM hTLR4 and flanking
cytoplasmatic where X represents Y or A);

SEQ ID NO: 107
KKVVSVVAVLVYXFYFXLMLKK
(predicted C-term-TM hTLR4 and flanking
cytoplasmatic where X represents H or
K or R or A);

SEQ ID NO: 108
KKSELSCNITLLIVTIGATMKK
kk(predicted N-term-TM hTLR6 with flanking
extracellular)kk;

SEQ ID NO: 109
KKVLAVTVTSLCIYLDLPWYKK
kk(predicted C-term-TM hTLR6)kk;

SEQ ID NO: 110
KKSELSANITLLIVTIGATMKK
kk(predicted N-term-TM hTLR6 with flanking
extracellular where C is substituted to A)kk;

SEQ ID NO: 111
KKXELXCNITLLIVTIGATMLVKK
kk(predicted N-term-TM hTLR6 with flanking
extracellular where X represents S or A)kk;

SEQ ID NO: 112
KKSXLSCNITLLIVTIGATMKK
kk(predicted N-term-TM hTLR6 with flanking
extracellular were X represents D or E or A)kk;

SEQ ID NO: 113
KKSELSCNIXLLIVXIGAXIVIKK
kk(predicted N-term-TM hTLR6 with flanking
extracellular here X represents T or A)kk;

SEQ ID NO: 114
KKSELSCNITLLIVTIGATAKK
kk(predicted N-term-TM hTLR6 with flanking
extracellular where M is substituted to A)kk;

SEQ ID NO: 115
KKVLAVTVTSLAIYLDLPWYKK
kk(predicted C-term-TM hTLR6 with flanking
cytoplasmatic where C is substituteed to A)kk;

SEQ ID NO: 116
KKVLAVTVTSLCIYLXLPWYKK
kk(predicted C-term-TM hTLR6 with flanking
cytoplasmatic where X represents A or D or E)kk;

SEQ ID NO: 117
KKVLAVTVTSLCIYLDLAWYKK
kk(predicted C-term-TM hTLR6 with flanking
cytoplasmatic where P is substituteed to A)kk;

SEQ ID NO: 118
KKVLAVTVTALCIYLDLPWYKK
kk(predicted C-term-TM hTLR6 with flanking
cytoplasmatic where S is substituteed to A)kk;

SEQ ID NO: 119
KKVLAVXVXSLCIYLDLPWYKK
kk(predicted C-term-TM hTLR6 with flanking
cytoplasmatic where X represents A or T)kk;

SEQ ID NO: 120
KKVLAVTVTSLCIYLDLPAYKK
kk(predicted C-term-TM hTLR6 where W is
substituted to A)kk;

SEQ ID NO: 121
KKVLAVTVTSLCIYLDLPWAKK
kk(predicted C-term-TM hTLR6 where Y is
substituted to A)kk;

SEQ ID NO: 122
KKSVIVVSTVAFLI
(predicted C-term TM mTLR4)

-continued

SEQ ID NO: 123
GLRILLLKV
(the core TM peptide of TCRα)

Materials & Methods (i) Peptide Synthesis and Purification.

Peptides were synthesized by a 9-fluorenylmethoxylcarbonyl (Fmoc) solid-phase method on Rink amide MBHA resin (Calbiochem-novabiochem, San Diego, Calif.) by using an ABI 433A automatic peptide synthesizer (Applied Biosystems, Foster City, Calif.). Peptide synthesis was followed by peptide cleavage from the resin by incubation for 3 h with 95% TFA, 2.5% H2O, and 2.5% triethylsilane. Purification of the crude peptide was preformed by RP-HPLC (>98%) on a Vydac C4 column (Grace Discovery Sciences, Deerfield, Ill.). The peptides' composition was confirmed by electrospray mass spectroscopy.

(ii) Cell Culture—Macrophages.

In-vitro assays were preformed on RAW264.7 murine macrophages (ATCC® Number-TIB-71). Cells were grown in DMEM supplemented with 10% FBS, L-Glutamine, Sodium pyruvate, non essential amino acids and antibiotics (Biological Industries, Beit Haemek, Israel). Incubator was set on 37° C. with a humidified atmosphere containing 5% CO2.

(iii) XTT Cytotoxicity Assays.

$1 \times 10^4$ cells (RAW264.7 murine macrophages, ATCC® Number-TIB-71) per well were grown over night on a 96-well plate. The following day, the media were replaced with 90 μl fresh culture medium and 10 μl solution buffer containing different concentrations of the different peptides mTLR2 TM N'-CtoA (SEQ ID NO:88), mTLR2 TM C'-CtoA (SEQ ID NO:86), mTLR1 TM N' (SEQ ID NO:77) and mTLR1 TM C'-CtoA (SEQ ID NO:83). Peptide concentrations range from 0.78-100 μM. The cells were then incubated for 2 hours before adding to each well 50 μl of 2,3-bis[2-methoxy-4-nitro-5-sulfophenyl]-2H-tetrazolium-5-carboxanilide inner salt (XTT) reaction solution (Biological Industries). Viability was determined as described previously (Papo et al., 2004 and Papo et al., 2006). The $LC_{50}$ (the concentration at which 50% of the cells die) for each peptide was obtained from the dose-dependent cell viability curves.

(iv) TNFα Secretion by RAW264.7 in Response to TLR Activation.

$2 \times 10^5$ cells per well were cultured overnight in 96-wells plate. The following day, the media were replaced by fresh DMEM, including all supplements. TLR peptides mTLR2 TM N'-CtoA (SEQ ID NO:88), mTLR2 TM C'-CtoA (SEQ ID NO:86), mTLR1 TM N' (SEQ ID NO:77) and mTLR1 TM C'-CtoA (SEQ ID NO:83) were dissolved in DMSO and added to the cells in different concentrations. Final concentration of DMSO was 1% for all groups. Cells were incubated with the peptide for 2 hours, then washed twice and incubated with fresh media containing LTA (lipoteichoic acid, a TLR2 activator) (Sigma-Aldrich) or LPS (lipopolysaccharide, a TLR4 activator) (Sigma-Aldrich). LTA concentrations varied between the different experiments. The cells were incubated for 5 hrs at 37° C., after which samples of the media from each treatment were collected and stored at −20° C. TNFα concentration in each sample was evaluated using a mouse TNFα enzyme-linked immunosorbent assay kit (Bender MedSystems, Almog), according to the manufacturers' protocol. All experiments were performed in triplicates.

(v) Fluorescent Labeling of Peptides.

For fluorescent labeling, we have used the following fluorophores: 4-Fluoro-7-nitrobenzofurazan (NBD-F, Bio-Chemika), 4-Fluoro-7-nitro-[2,1,3]-benzoxadiazole (NBD Apollo), 5(6)-carboxyfluorescein N-hydroxysuccinimide ester (Fluorescein, BioChemika) and 5(6)-carboxytetramethylrhodamine N-succinimidyl ester (TAMRA, BioChemika). Resin-bound peptides were treated with either of the listed fluorophore dissolved in dimethyl formamide (DMF), leading to the formation of resin-bound N-terminal fluorophore peptides. 2% DIEA (Sigma-Aldrich) was added to the TAMRA and fluorescein solutions. Incubation was done for 1 hr (NBD) or overnight (TAMRA and fluorescein). Following the incubation, the resin was washed thoroughly with DMF and then with methylene chloride, dried under nitrogen flow, and then cleaved and purified as described in (i) above.

(vi) Fluorescence Resonance Energy Transfer (FRET) for Fluoresceni/NBD and Rhodamaine (TAMRA) Labeled Peptides.

Large unilamellar vesicles (LUVs) composed of phosphatidylcholine (PC) and cholesterol (10:1, w/w), were prepared using the extrusion method as described previously (Cohen et al, 2008). The fluorescence experiments were performed with pairs of peptides using fluorescein labeled peptides as donors and rhodamine labeled peptides as acceptors. Fluorescence spectra were obtained at room temperature, with excitation set at 494 nm (10 nm slit) and emission scan at 500-600 nm (10 nm slits), by a Cary eclipse fluorescence spectrophotometer (Varian Inc., Palo Alto, Calif.). In a typical experiment, a fluorescein labeled peptide was first added from a stock solution in DMSO (final concentration of 0.1 μM peptide and 0.25% (v/v) DMSO) to a solution containing PC:Cholesterol LUVs (100 μM) in HEPES buffer. This was followed by the successive addition of rhodamine labeled peptides to a final concentration ranging from 0.025 to 0.4 μM. Fluorescence spectra were obtained before and after the addition of the rhodamine labeled peptides. Fluorescence values were corrected by subtracting the changes in emission obtained by adding HEPES only. Maximum FRET values were obtained by calculating the changes in the emission of the donor peptide at 521 nm.

(vii) Membrane Binding Assays.

PC:Cholesterol LUVs were successively added to a 0.1 μM NBD-labeled peptide dissolved in double distilled water. The changes in NBD emission (530 nm; ΔF) were monitored as a function of the lipid/peptide molar ratio with excitation set at 467 nm (10-nm slit) until the system reached equilibrium. To account for the background, the emission of LUVS alone at the same wavelength was subtracted. The changes in the probe emission represents the amount of peptide bound to the hydrophobic interface, because NBD is known to change its emission in a hydrophobic environment (Rapaport et al. 1991) thereby enabling us to evaluate the peptide binding to LUVs. Our system reached binding equilibrium (Fmax) at a certain lipid/peptide ratio, and therefore the affinity constant could be calculated from the relationship between the equilibrium level of NBD labeled peptide emission and the lipid concentration, using a steady state affinity model. The affinity constants were thus determined by nonlinear least-squares (NLLSQ) analysis. The NLLSQ fitting was done using the following equation—

$$Y(x)=K_a*X*F_{max}/(1+K_a*X) \quad \text{(Eq. 1)}$$

wherein X is the lipid concentration, Fmax is the maximal difference in the emission of NBD-labeled peptide before and after the addition of the lipids (it represents the maximum lipid peptide bound or the equilibrium-binding response), and Ka is the affinity constant, in $M^{-1}$.

(viii) Co-Immunoprecipitation Assays.

$2.5*10^6$ RAW264.7 (murine macrophages, ATCC® Number-TIB-71) cells were incubated with 0, 5 or 10 μM rhodamine labeled peptides, for 2 hours at 37° C. The cells with peptide were washed and lysed with ice cold RIPA buffer (Tris pH 7.4 20 mM, NaCl 137 mM, Glycerol 10%, Triton-X 1%, Sodium deoxycholate 0.5%, SDS 0.1% and protease inhibitor cocktail 1:100 dilution). After 15 minutes centrifugation at 14,000 RPM, 4° C., the soluble fraction was separated and incubated for 2 hours with different TLR antibodies. Protein G beads (Santa Cruz) were added for further overnight incubation. The beads were washed with cold PBS 5 times, diluted 1:2 with SDS tricine buffer (Novex®, invitrogen) and boiled for 10 minutes at 95° C. Samples were run on a 10% SDS-PAGE. The presence of the labeled peptide was detected with a Typoohn fluorescent scanner (GE Healthcare, Waukesha, Wis.). Excitation was set at 532 nm and emission at 585 nm. The detection of the TLR proteins was preformed by western blot analysis with standard ECL solution (Pierce). Primary antibodies used were anti-TLR1 (Santa Cruz), anti-TLR2 (eBioscience), and anti-TLR4 (BioLegend), secondary antibodies used were anti-rat (Santa Cruz).

(ix) Circular Dichroism (CD) Spectroscopy.

CD measurements were performed on an Aviv 202 spectropolarimeter (Aviv Instruments, Lakewood, N.J.). The spectra were scanned using a thermostatic quartz cuvette with a path length of 1 mm. All measurements were done at 25° C. The average time recording of each spectrum was 20 sec in 1 nm steps in the wavelength range of 190-260 nm. The peptides were scanned at a concentration of 10 μM (50 μM for TLR1 TM C' only) in a 1% lyso-phosphatidilcholine solution (Sigma Aldrich).

(x) Self Assembly Assays.

Rhodamine-labeled peptides were dissolved in DMSO, added to 400 μl of HEPES or to 0.1 mM PC:Cholesterol solution and brought to equilibrium (peptides' final concentration was 0.1 μM, DMSO 0.025% v/v). Using an SLM-Aminco® luminescence spectrometer (SLM-Aminco, Rochester, N.Y.) changes in the intensity of the fluorescence emission were followed before and after the addition of proteinase-K (Sigma Aldrich). Excitation wavelength was set at 530 nm, emission at 580 nm, final concentration of proteinase-K was 62.5 μg/ml. An increase in fluorescence indicates that the peptide exists as an oligomer (Papo et al., 2002). All fluorescence measurements were performed at 25° C.

(xi) In-Vivo Studies.

To examine the effect of TLR TM peptides on acute septic shock driven by TLR2 hyperactivation we have used a murine model as previously described (Meng et al., 2004). Briefly, 12 weeks old C57 Black female mice (supplied by Harlan) were treated with 100 μg of LTA injected IP in a saline solution (pH 6.5) containing 200 μg/ml of D-galactoseamine (Calbiochem). Treated mice received two injections of peptide at doses of 1, 5 and 10 mg/kg. First injection was given at the time of LTA injection, second injection was given 2 hrs (1 mg/kg) or 12 hrs (5 and 10 mg/kg) later. Animals were monitored for survival for 96 hours after LTA injection. Peptides used for in-vivo experiments were treated twice with 20% acetic acid in order to replace the trifluoroacetate anion added during HPLC purification. For all groups n=8.

(xii) Cell i Prostate Cancer.

Several types of prostate cancer cell lines (kindly provided by Prof. Zelig Eshhar at the Weizmann Institute of Science) were used, with known characteristics of androgen dependency and ability to induce metastesis. PC3 (ATCC® Number CRL-1435D) and DU145 (ATCC® Number HTB-81D) are known as highly metastatic and androgen independent and are widely considered as cell line model for advanced prostate cancer. 22RV1 (ATCC® Number CRL-2505D, androgen independent) and LNCaP (ATCC® Number CRL-1740D, androgen dependent) are known as low metastatic.

(xiii) TLR Expression in Prostate Cancer Cell Lines.

PCR reactions were performed to examine the presence of cDNA of TLR 1, 2 and 6 in the four prostate cancer cell lines described in (xii) above, namely: PC3 and LNCaP (highly metastatic) and LNCaP and 22RV1 (low metastatic). Total RNA was collected from cell lysates using TRI Reagent® (a complete, ready-to-use reagent for the isolation of total RNA, Applied Biosystems) and according to the manufactures instructions. By annealing oligo dTs only the mRNA from this pool of RNA was kept and then specific primers were used for each TLR gene. Primers were generated using the PubMed tools and database.

(xiv) NFkB Transcription Activity in Response to TLR Activation in Prostate Cancer Cell Lines.

The NFkB responsive element has been widely researched and is known to serve as a specific indication for the presence of the NFkB molecule inside the nucleus. Such a translocation occurs upon activation of the signaling cascade of TLRs, which leads to targeted transcription. This DNA element was introduced into a Luciferase expressing plasmid upstream to the gene thus generating a reporter plasmid for the presence of NFkB in the nucleus. Cells were transfected with the plasmid and 24 hours later were treated with LPS/LTA to induce the signaling cascade through TLR4 and TLR2, respectively. To validate activation, the levels of Luc expression were evaluated using the Steady-Glo kit (Promega) according to manufactures instructions.

Example 1. Peptides Corresponding to the N and C Terminus of the TM Domain of TLR2/1/6 are Able to Inhibit TNFα Secretion by RAW264.7 Macrophages Upon LTA Activation In order to examine the role of the transmembrane (TM) domain in TLR2 and TLR1/6 we first identified the putative TM domains of these proteins. The peptides having the sequences designated herein as SEQ ID NO:1 to SEQ ID NO:16, comprise the sequences of the predicted TM domain and the predicted TM with flanking cytoplasmic and extracellular regions, respectively, for TLR1, 2 and 6 from human and mouse. The predicted TM domains are 21 to 22 amino acid long. A short hydrophobic region is adjacent to the TM domain, from the intracellular side. The amino acid sequence of TLR1 and TLR6 TM domain is virtually identical.

To investigate their role in activation of TLR2, we have used the approach of adding synthetic peptides that correspond to either TLR2 or TLR1 TM domain and tested their ability to affect macrophage activation by lipoteichoic acid (LTA), a TLR2 activator. This system is based on a large body of evidence showing that exogenously added TM peptides can affect the activity of a certain protein through interactions with its TM domain (Bennasroune et al., 2004). Initially, we have designed for each TM domain of TLR2 and TLR1, two overlapping peptides containing ~20 amino acids each: one corresponding to the N-terminus TM and the other corresponding to an extended C-terminus TM domain (Table 1). We have chosen to extend the C-terminus TM domain as this region corresponds to a similar region in TLR4 that was shown to regulate the oligomerization of this protein. In addition we have synthesized analogs of these peptides with various substitutions. In several peptides, cysteine residues were mutated to alanines for synthetic ease, since cysteine residues within TM domains usually do not affect the activity of a membrane protein (Table 1). Additionally, lysines were added to the ends of these peptides to improve solubility.

Our results show that the synthetic peptides derived from the TM domains of TLR2 and TLR1, namely, mTLR2 TM N'-CtoA (SEQ ID NO:88), mTLR2 TM C'-CtoA (SEQ ID NO:86), mTLR1 TM N' (SEQ ID NO:77) and mTLR1 TM C'-CtoA (SEQ ID NO:83), were able to significantly inhibit TNFα secretion from macrophages after LTA activation (FIGS. 1A-1D). The inhibition was dose-dependent, highest at peptide concentration of 10 µM, and was performed under low TLR2 activation. Activation was achieved by 100 ng/ml LTA resulting in ~50 pg/ml TNFα secretion (FIG. 1A). However, in all peptide concentrations, no effect was seen on TNFα secretion induced by lipopolysaccharide (LPS), a TLR4 agonist (FIG. 1B).

In order to test whether this inhibition can take place under high levels of TLR2 activation, macrophage cells were stimulated with 500 ng/ml LTA, which resulted in TNFα levels of ~500 pg/ml. Under these conditions, TLR TM peptides at 20 µM reduced TNFα secretion by 40-60% (FIG. 1C). The peptides were used at concentrations well below their toxic concentrations (Table 1). Taken together, these findings suggest that the effect of the TLR2 and TLR1 TM peptides is specific for TM peptides within large unilameler vesicles (LUVs). Phosphatidilcholine (PC) and cholesterol (10:1) LUVs were used to mimic the outer leaflet of mammalian cells. TLR1 TM peptides mTLR1 TM N' (SEQ ID NO:77) and mTLR1 TM C'-CtoA (SEQ ID NO:83) labeled with fluorescein were used as donors, and their counterparts TLR2 TM peptides mTLR2 TM N'-CtoA (SEQ ID NO:88), mTLR2 TM C'-CtoA (SEQ ID NO:86) labeled with rhodamine as acceptors. Measuring the decrease in the emission of fluorescein conjugated peptides, after the addition of successive amounts of rhodamine labeled peptides, served as an indication for the interaction between a pair of peptides.

Figure 2A:
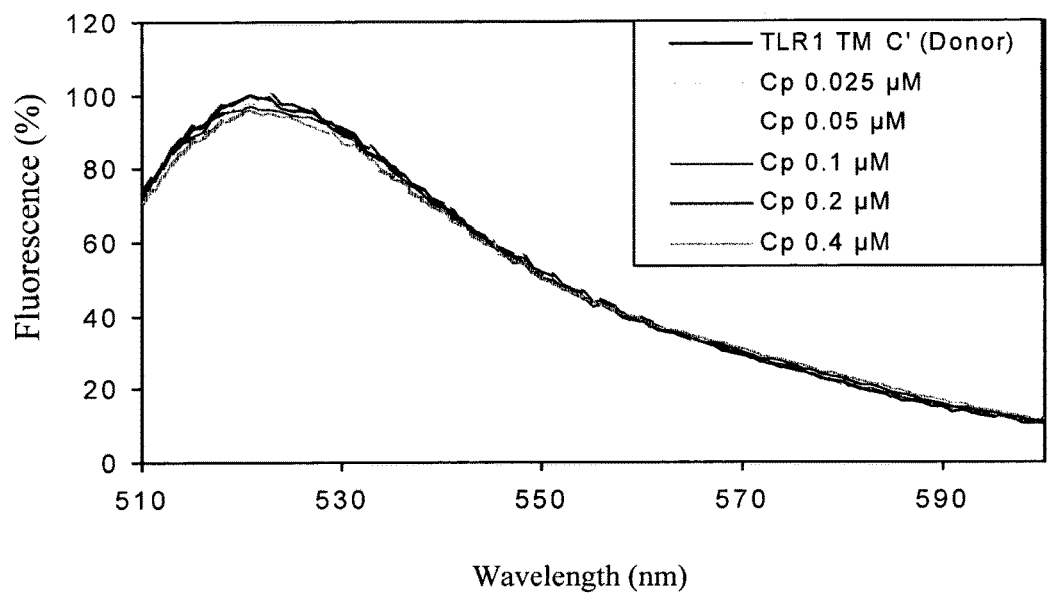
FIGS. 2A-2C show fluorescence resonance energy transfer (FRET) between mTLR1 TM C'-CtoA (SEQ ID NO:83) and other TM peptides. mTLR1 TM C' peptide was labeled with fluorescein (Donor) and loaded on PC:Cholesterol large unilamellar vesicles (LUVs). Changes in the intensity of the emission signal were monitored between 500 to 600 nm, upon the addition of successive amounts of rhodamine labeled mTLR1 TM C'-CtoA (SEQ ID NO:83; homodimers, 2B) and mTLR2 TM C'-CtoA (SEQ ID NO:86; heterodimers, 2C). Rhodamine labeled TCRα TM domain peptide (Cp; GLRILLLKV-NH2, SEQ ID NO:123) was used as a negative control (2A).
Figure 2B:
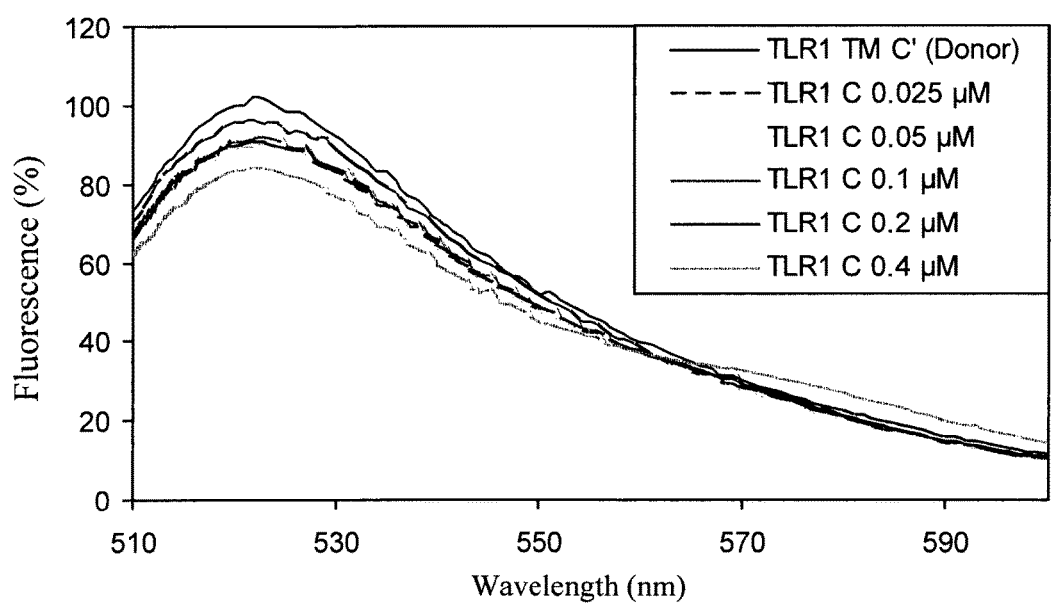
Figure 2C:
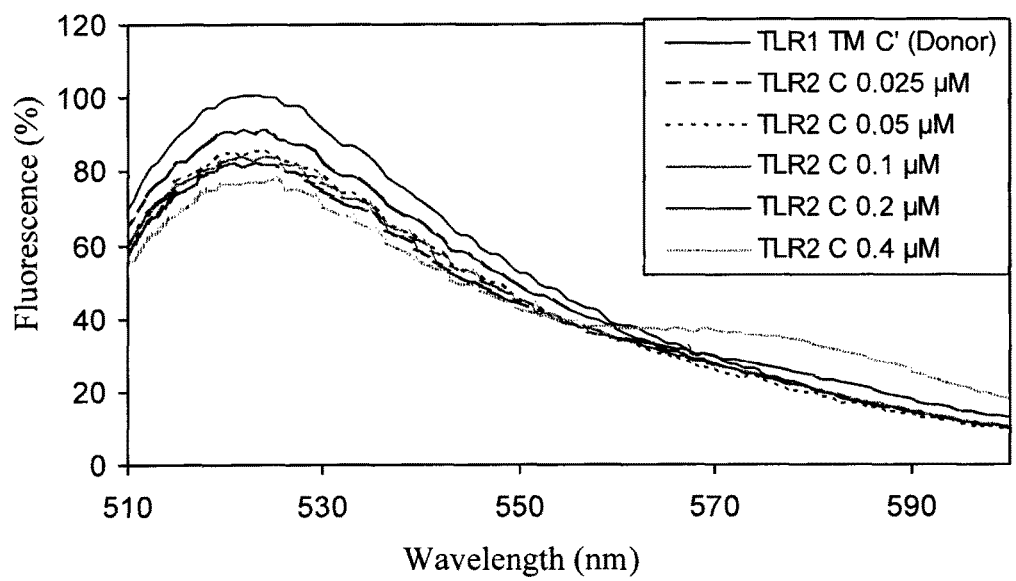
Figure 3A:
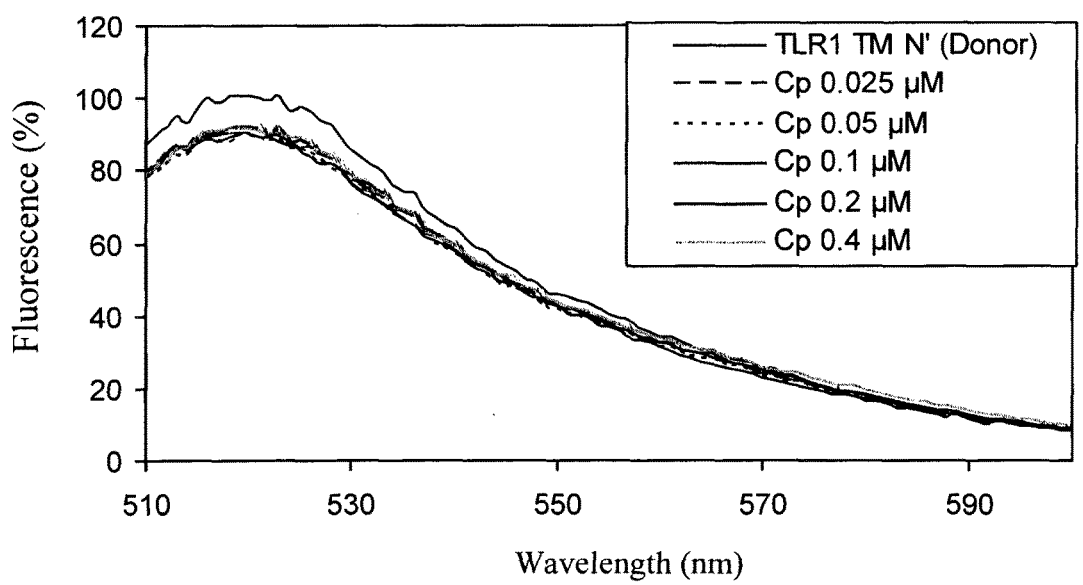
FIGS. 3A-3C show FRET between mTLR1 TM N' (SEQ ID NO:77) and other TM peptides. mTLR1 TM N' peptide labeled with fluorescein (donor) and loaded on PC:Cholesterol LUVs. Changes in the intensity of the emission signal were monitored between 500 to 600 nm, upon the addition of successive amounts of rhodamine labeled mTLR1 TM N' (SEQ ID NO:77; homodimers, 3B) and mTLR2 TM N'-CtoA (SEQ ID NO:88; heterodimers, 3C). Rhodamine labeled TCRα TM domain peptide (Cp; GLRILLLKV-NH2, SEQ ID NO:123) was used as a negative control (3A).
Figure 3B:
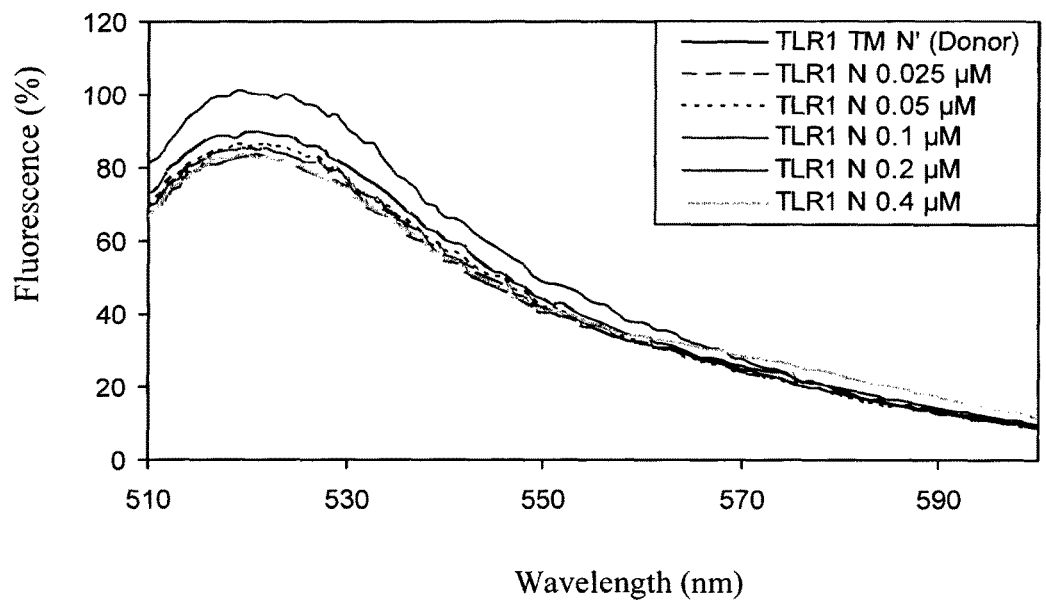
Figure 3C:
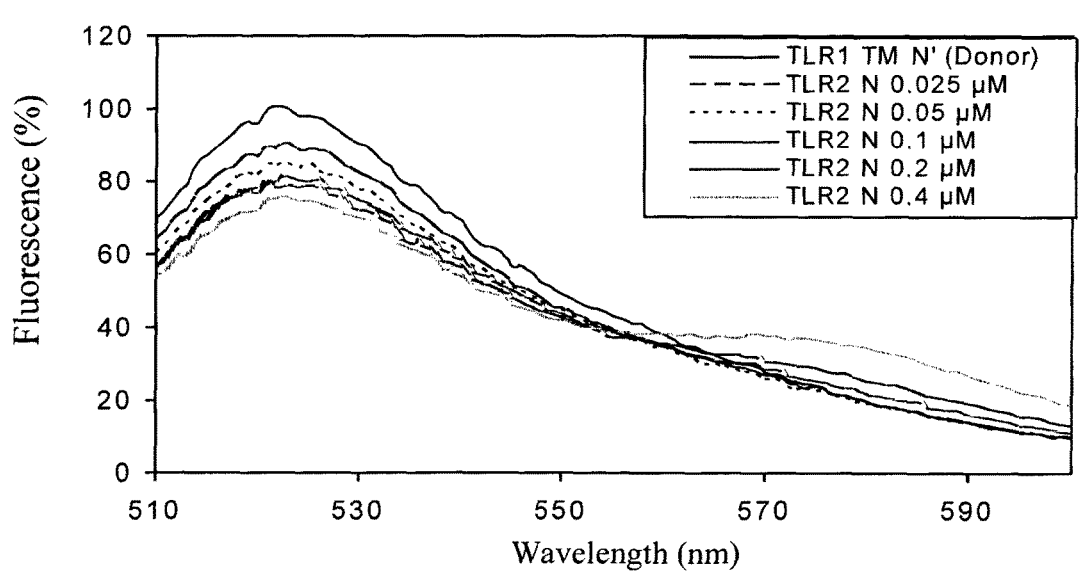

TLR1 TM derived TM peptides were capable of forming both homodimers as well as heterodimers with TLR2 TM peptides (FIGS. 2A-2C and 3A-3C). TLR1 TM C-terminus and N-terminus peptides showed much higher propensity towards forming heterodimers than homodimers. Maximum calculated FRET for mTLR1 TM C' homodimers was 16.1±1.9% (FIG. 2B). mTLR1 TM N' homodimers showed 14.2±2.3% FRET (FIG. 3B) while mTLR1/2 C' and mTLR1/2 TM N' heterodimers gave a maximum signal decrease of 20.6±1.7% and 25.3±2.0%, respectively (FIGS. 2C and 3C). Rhodamine conjugated Cp, the core TM peptide of TCRα (SEQ ID NO:123) was used as a negative control and showed no significant fluorescence signal decrease (FIGS. 2A and 3A). Taken together, these finding demonstrate the ability of the different TMs to interact with each other and is consistent with the fact that these proteins require a shift towards heterodimerization for their activation. Our FRET results suggest that the TM domains of these proteins are also a factor involved in this transition.

TABLE 1

Peptide designations and characteristics

| SEQ ID | Peptide | Sequence | LC50[1] (µM) |
|---|---|---|---|
| 79 | mTLR1 C' TM | kkLAVTGAFLCLYFDLPWkk | >100 |
| 77 | mTLR1 N' TM | kkLLTVTIGATMLVLAVTGAkk | >100 |
| 80 | mTLR2 C' TM | kkLILLVGALCHHFHGLWkk | 50 |
| 76 | mTLR2 N' TM | kkALVSGVCCALLLLILLVGkk | N.A |
| 83 | mTLR1 C' TM (C to A) | kkLAVTGAFLALYFDLPWkk | 50 |
| 82 | mTLR1 C' TM (C + D to A) | kkLAVTGAFLALYFALPWkk | N.A |
| 83 | mTLR1 C' TM (C to A + L605S) | kkLAVTGAFLASYFDLPWkk | >100 |
| 86 | mTLR2 C' TM (C to A) | kkLILLVGALAHLIFHGLWkk | 50 |
| 85 | mTLR2 C' TM (C + 3H to A) | kkLILLVGALAAAFAGLWkk | N.A |
| 88 | mTLR2 N' TM (C to A) | kkALVSGVAAALLLLILLVGkk | >100 |

[1]LC50 (Lethal Concentration at which 50% of cells die) is presented for RAW264.7 cells TLR2, since they did not affect the activation of a closely related protein TLR4 (FIG. 1D). Two additional controls were added to verify the results for these experiments. First, the addition of the peptides alone did not alter the basal level of TNFα secretion (results not shown). Second, the peptides were non toxic to mouse macrophages under our experimental conditions as revealed in an XTT toxicity assay (Table 1).

Example 2. FRET Experiments Reveal that TLR TM Peptides have a Higher Tendency to Form Heterodimers than Homodimers Fluorescence Resonance Energy Transfer (FRET) analysis was used for exploring the interactions of the synthetic Example 3. TLR1 TM Peptides Bind to Model Membranes with High Affinity We determined the ability of TLR1 TM peptides to bind to model membranes, as this property is important for our calculated FRET results. As the fraction of the peptides bound to the LUVs correlates to the strength of the observed FRET signal, it is important to define this parameter. Therefore, measuring the increase in the emission of 4-Fluoro-7-nitrobenzofurazan (NBD) conjugated peptides, after the addition of successive amounts of LUVs, serves as an indication for their affinity towards eukaryotic membranes. NBD emission increases upon insertion into a hydrophobic surrounding.

Figure 4A:
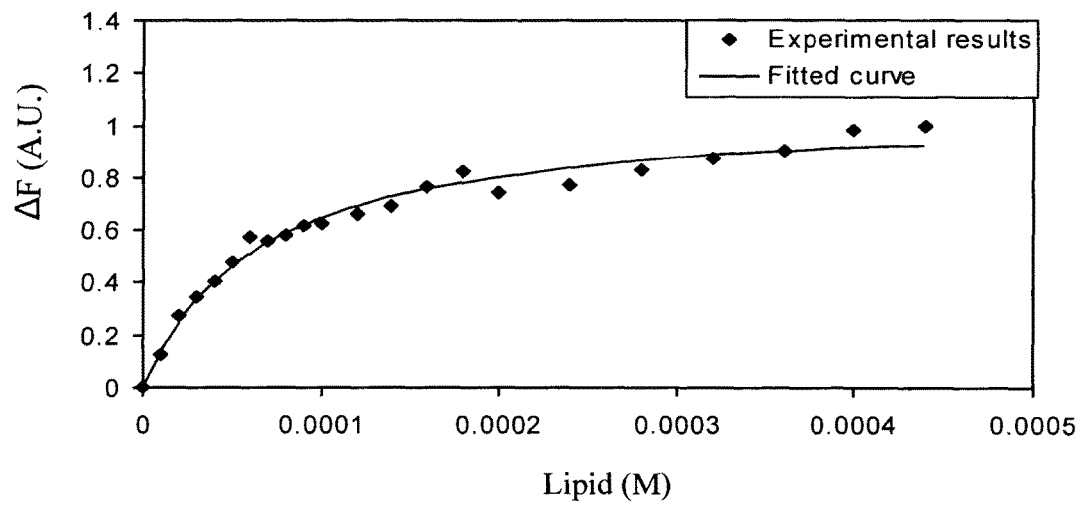
FIGS. 4A-4B show that peptides based on the transmembrane domain of TLR1 have high affinities towards mimic membranes. The emission of 4-Fluoro-7-nitrobenzofurazan (NBD)-labeled mTLR1 TM N' (SEQ ID NO:77; 4A) and mTLR1 TM C'-CtoA (SEQ ID NO:83; 4B) was followed upon titration with LUVs. An increase in the signal at 530 nm indicates the association of the NBD-peptide with the PC:Cholesterol hydrophobic vesicles.
Figure 4B:
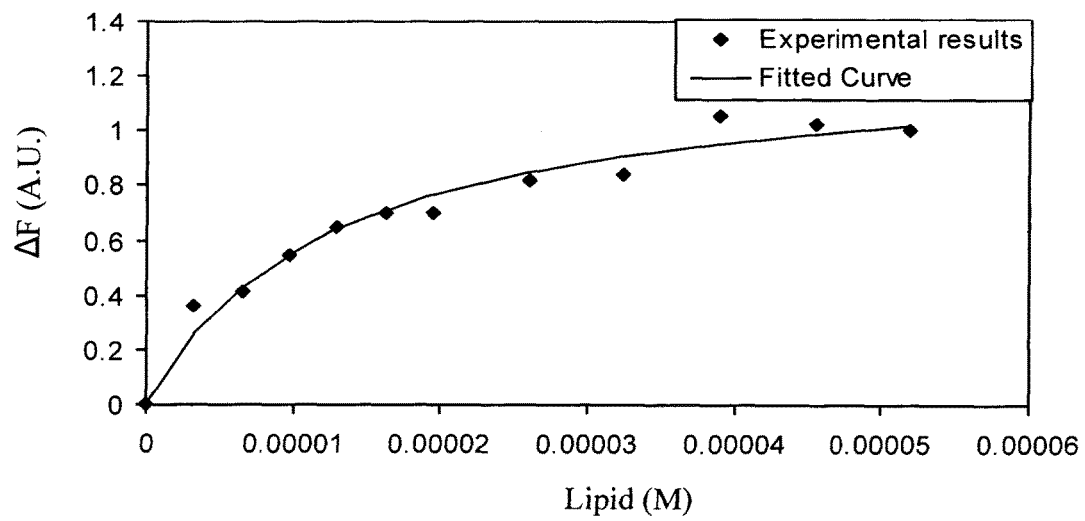

Both mTLR1 TM C'-CtoA and mTLR1 TM N' labeled peptides (SEQ ID NO:83 and SEQ ID NO:77, respectively) show high affinity towards PC:Cholesterol liposomes with $K_a$ values of $7.8 \times 10^4$ $M^{-1}$ and $1.5 \times 10^4$ $M^{-1}$, respectively (FIGS. 4A and 4B). These relatively high $K_a$ values indicate that the peptides were fully bound to the liposomes in the FRET experiments.

Example 4. TLR2 TM Peptides are Able to Physically Interact with TLR1 Protein Rather than with TLR2 or TLR4

To support our hypothesis, we have performed co-immunoprecipitation (co-IF') experiments to detect TLR protein interactions with TLR TM peptides. This experimental approach uses a fluorescent probe (rhodamine) conjugated to TLR TM peptide and specific antibodies against TLR proteins. Cell lysates with the peptide were incubated with specific TLR antibodies bound to protein G beads. These complexes were then subjected to SDS-PAGE. The presence of the fluorescent peptide was verified by a fluorescent scanner and the presence of precipitated TLRs was verified using western blot analysis.

At 10 µM, both mTLR2 TM N'-CtoA and mTLR2 TM C'-CtoA peptides (SEQ ID NO:88 and SEQ ID NO:86, respectively) precipitate significantly more with TLR1-antibodies compared with TLR2 and TLR4 antibodies (FIGS. 5A-5B). These results are in agreement with the FRET results and support our model suggesting that TLR1 protein preferentially associates with TLR2 TM peptides. Western blot analysis revealed that TLR2/1 and 4 co-precipitates together, regardless of the addition of the peptides (FIG. 5B). These results further strengthen the idea that these proteins form large complexes on the plasma membrane and are capable, at least in-vitro, to interact with each other.

Figure 6A:
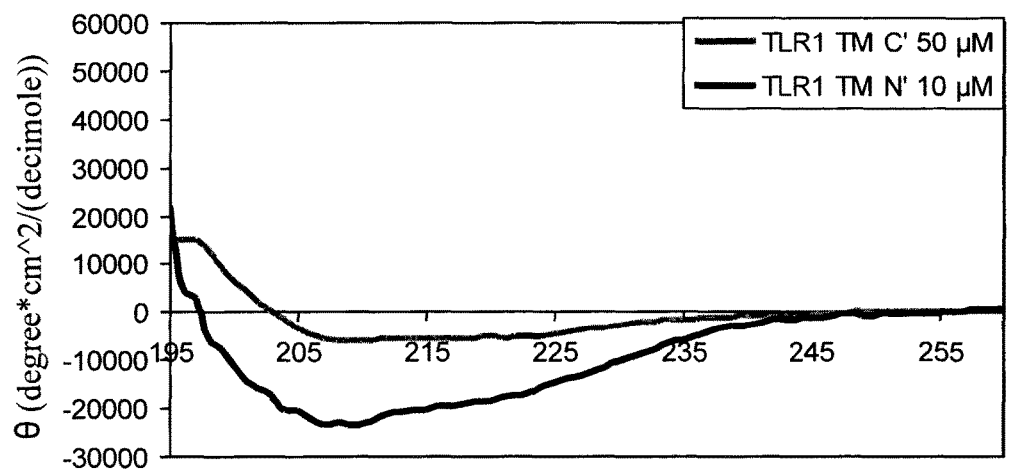
FIGS. 6A-6B show circular dichroism (CD) spectroscopy revealing structural differences between the different peptides in lysophosphatidylcholine (LPC) micelles. (6A) CD performed for peptides based on the transmembrane domain of TLR1, namely, mTLR1 TM N' (SEQ ID NO:77) and mTLR1 TM C'-CtoA (SEQ ID NO:83) show a characteristic a helix for both C-terminus and N-terminus peptides. The signal for mTLR1 TM C'-CtoA (SEQ ID NO:83) is very weak suggesting a relatively low a helix content. Note that this signal was obtained only at a high concentration of 50 µM peptide. (6B) peptides based on the transmembrane domain of TLR2, namely, mTLR2 TM N'-CtoA (SEQ ID NO:88) and mTLR2 TM C'-CtoA (SEQ ID NO:86) show a characteristic a helix for both C-terminus and N-terminus peptides.
Figure 6B:
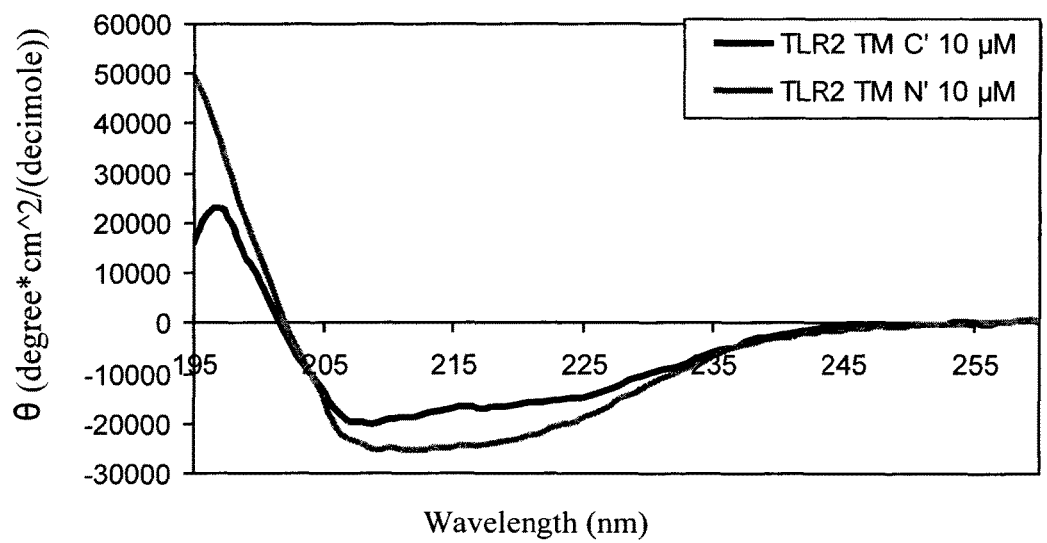

Example 5. TLR2/1 TM Peptides are α-Helical and Differ in their Ability to Form Complexes in Buffer and Lipid Environment In order to gain a better understanding of the structure-function relationship of the TLR TM peptides, we have determined their structures in a lipid interface, as well as their ability to self assemble. Using circular dichroism (CD) spectroscopy we determined their structures in lysophosphatidylcholine (LPC) micelles. As can be seen in FIGS. 6A-6B, mTLR1 TM N' (SEQ ID NO:77) as well as mTLR2 TM N'-CtoA and mTLR2 TM C'-CtoA (SEQ ID NO:88 and SEQ ID NO:86, respectively) adopt an α helical structure in LPC micelles. The signal obtained for these peptides was relatively strong ($\theta = \sim 15$–$20 \times 10^{-3}$ Degree×cm²/Decimole at 208 and 222 nm) at a peptide concentration of 10 µM.

mTLR1 TM C'-CtoA (SEQ ID NO:83) showed no signal at 10 µM and gave only a weak α helical signal at 50 µM (FIG. 6A). This suggests that this peptide has a lower a helix content than the other peptides examined. However, we can not rule out the possibility that the low signal was due to additional β-sheet structures or low insertion rates.

In addition, we have examined the ability of these peptides to self assemble in homo-oligomers, as this property of membrane active peptides has been shown to affect their activity (Rosenfeld et al., 2006b; Rosenfeld et al., 2006c). We have tested this characteristic, both in solution and on a membrane interface. We measured the initial emission of rhodamine labeled peptides at 580 nm in solution only, or in a solution containing PC:Cholesterol LUVs, and then followed the increase of the emission over time after the addition of protease-K to the medium. A high and fast increase in the fluorescence over time indicated that the fluorophore conjugated peptide was in an oligomeric quenched state. The known oligomeric antimicrobial peptide LL37 (Rosenfeld et al., 2006a) was used as a positive control.

In HEPES solution mTLR1 TM N' and mTLR1 TM C'-CtoA (SEQ ID NO:77) and SEQ ID NO:83 respectively), as well as mTLR2 TM C'-CtoA (SEQ ID NO:86) gave very slow increase in fluorescence over time, suggesting that these peptides form oligomers in solution to some extent (FIG. 7A). These self oligomers can be dissociated by protease treatment as can be seen by their relatively slow increase in emission. In contrast, mTLR2 TM N'-CtoA (SEQ ID NO:88) revealed a very strong propensity to form aggregations in solution, as can be revealed by the low initial emission rate for this peptide. These aggregations were not dissociated upon the addition of protease K to the solution (FIG. 7B, black line), but were shown to partially dissolve upon the addition of LUVs to the system (FIG. 7B, gray line), suggesting that in a lipid environment, mTLR2 TM N'-CtoA peptides favor a monomeric form.

Figure 7C:
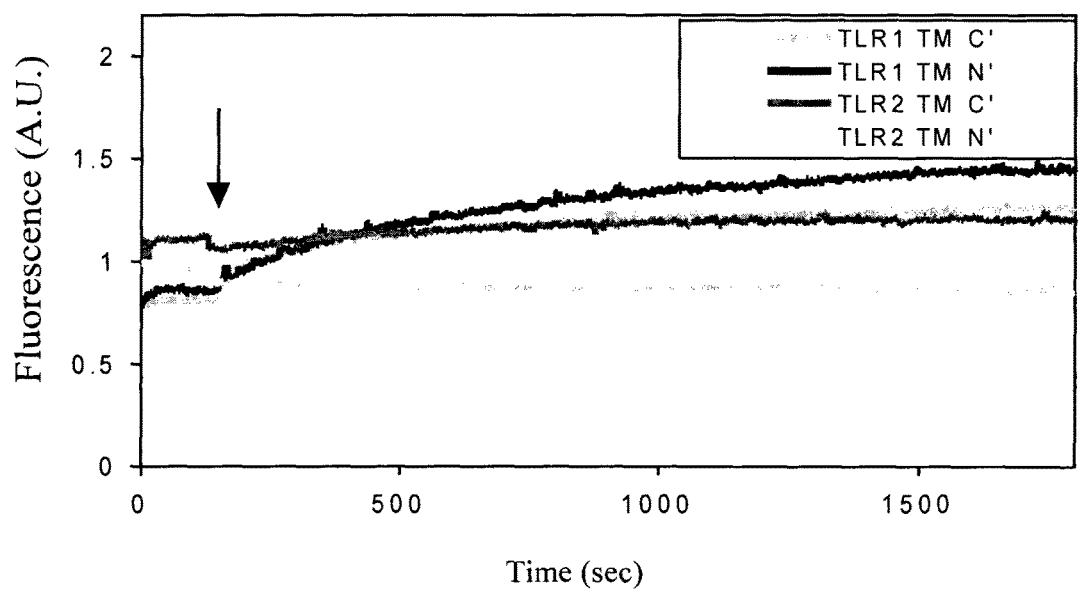
Figure 7D:
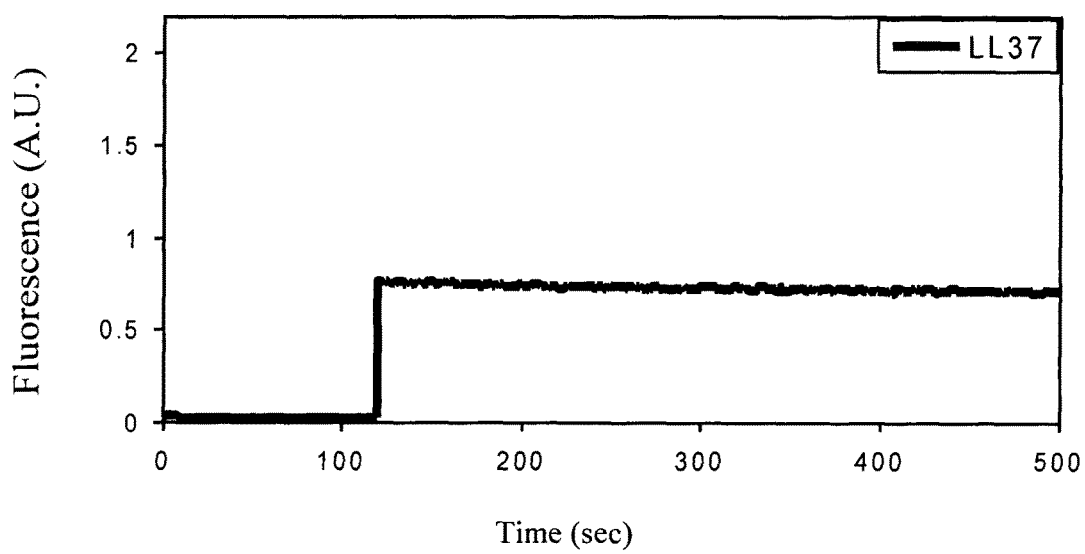

A different picture was seen in a solution containing LUVs. While TLR2 TM peptides did not show any changes before and after the protease treatment, TLR1 TM peptides were shown to dissociate to some extent suggesting that these peptides do form homooligomers in membranes, to some extent (FIG. 7C). These results are clearly in line with our FRET results, suggesting that both mTLR1 TM N' and mTLR1 TM C'-CtoA can self assemble to form homodimers. As expected, the positive control of LL37 showed a very high and fast recovery of fluorescence in a lipid environment (FIG. 7D), characteristic of highly oligomeric peptides.

Example 6. Peptides Based on TLR2 TM Domain are Able to Inhibit TLR2 Hyperactivation In-Vivo In order to test the activity of our peptides in-vivo, we have used a murine model for acute septic shock caused by hyperactivation of TLR2. Mice were injected i.p. with 100 µg of LTA and then treated with mTLR2 TM C'-CtoA peptide (SEQ ID NO:86) in different regimes (see materials and methods section (xi)) or with saline only. As can be seen in FIG. 8, survival of mice treated with saline only dropped to 0% within 48 hours after LTA injection. In contrast, mice treated with 1 or 5 mg/kg peptide showed survival rates of 50% and 62.5%, respectively, up to 14 days after LTA injection. During the whole experiment, mice treated with the peptide showed no noticeable adverse effects.

Example 7. Specific Expression of TLRs on Metastatic and Non-Metastatic Prostate Cancer Cell Lines We determined the mRNA levels of expression of TLRs in several types of prostate cancer cell lines: PC3 and DU145 which are known as highly metastatic and 22RV1 and LNCaP which are known as low metastatic (data presented only for PC3 and LNCaP). Interestingly, PC3 cells express all tested TLRs (1, 2 and 6), whereas in LNCaP, only mRNA transcripts of TLR1, 2 and 6 were detected (FIG. 9). We then tested whether these transcripts are actually functional on these cells. To this end we used a luciferase (Luc) expression assay which is based on the presence of NFkB in the nucleus, thus reporting the end product of the signaling cascade of TLR activation. Incubating PC3 cells in the presence of LPS (TLR4 activator) or LTA (TLR2 activator) resulted in a significant increase in the Luc expression (FIG. 10).

Example 8. A Synthetic Peptide Derived from TMD of TLR2 Influences the Activation of Prostate Cancer Cell Lines We synthesized peptides corresponding to either the N-terminus or C-terminus domains of the TM domains of human TLR1, 2 and 5. Each TM domain was divided into two overlapping sequences (Table 2). Activity and toxicity experiments were performed on a peptide corresponding to the C-terminus domain of the TM domain of human TLR2, including the adjacent 5 amino acids from the putative intracellular domain (SEQ ID NO:83, hTLR2-C in Table 2 below, extended with two lysine residues at each of its termini to increase solubility). The peptide was not toxic to either PC3 or LNCaP cell lines at a concentration of up to 100 µM (the maximal concentration tested, data not shown).

TABLE 2

Peptide designations and sequences

| SEQ ID NO | Peptide designation | Peptide sequence[1] |
|---|---|---|
| 24 | hTLR1-C | LAVTVTSLCIYLDLPWYLR |
| 17 | hTLR1-N | LLIVTIVATMLVLAVTV |
| 25 | hTLR2-C | LILLTGVLCHRFHGLW |
| 18 | hTLR2-N | ALVSGMCCALFLLILLTG |

[1]Shadowed sequence—intracellular domain

The hTLR2 TM C' peptide (SEQ ID NO:83) was then tested for its ability to inhibit the signaling cascade of the TLRs upon their activation with LTA and LPS. When activated with LTA in the presence of the peptide (20 µM), Luc expression was inhibited by 40% in the PC3 cells (FIG. 10). Importantly, when cells were activated with LPS, the peptide could not inhibit the activation, pointing out to the specificity of the inhibition (FIG. 10). A possible explanation for the fact that there is a reduction of the base line may be due to the activation of the TLRs through the secretion of DAMPs by the culture cells at normal growth conditions.

An important question is whether the reduction in cell activation induced by the peptide shown in FIG. 10 will result also in a reduced rate of cell growth. Indeed, incubation of the cells with 20 µM peptide for 72 hours (a freshly dissolved peptide was added every 24 hours), caused 20% inhibition in proliferation (FIG. 11).

Example 9. Inhibition of the Expression of Cytokines mRNA by the Peptide

One of the main features of metastatic cells is their ability to influence their environment due to the secretion of various cytokines. Two of the most influential cytokines are VEGF which induces the formation of blood vessels, and TGFβ which e.g. induces tolerance of immune cells and inhibits apoptosis. We therefore determined the expression of the mRNA of these cytokines in the cells upon their activation with LPS and LTA and the effect of the peptide on the activation. Interestingly, only PC3 cells showed a marked increase in the expression of the cytokine's mRNA upon stimulation (FIG. 12). In addition, a drop in the levels of expression in the presence of the hTLR2 TM C' peptide (SEQ ID NO:83) was observed (FIG. 13). These findings lead us to the hypothesis that the presence of the TLRs on PC3 cells contribute to the severity (aggressiveness) of the cancer and its ability to form metastases. Thus, the TLR TM peptides of the invention can be used as new diagnostic biomarkers, which can indicate the rate of growth and the ability of the cells to form metastases.

Example 10. Correlation Between the Level of TLR Expression on Prostate Cancer Cells, their Functionality and their Ability to Generate Metastasis The repertoire of TLRs expressed in both metastatic and non-metastatic cell lines, at the protein level, is examined by western blot.

The functionality of the various TLRs i.e. their ability to secrete anti inflammatory cytokines, is tested via their activation by the corresponding ligands (LTA for TLR1/2/6) and determined by ELISA assays.

Example 11. Activation of the TLRs Require their or Hetero-Assembly (TLR1, 2 and TLR6/2)

The contribution of the transmembrane domains (TMDs) of TLRs 1, 2 and 6 to the assembly process is examined by searching for TMD-TMD homo-dimer and hetero-dimer assembly in living cells. The ToxR-TM-MalE system is used to detect homodimerization in living bacteria (Langosch et al., 1996; Gerber et al., 2001), and the LexA-TM-MalE system to detect heterodimer formation (Lindner et al., 2006; experimental details in Korazim et al., 2006; Gerber et al., 2004 and Papo et al., 2002).

The synthetic peptides (as described in Example 8, Table 2 above) are engrafted into the ToxR-TM-MalE and LexA-TM-MalE systems to identify the minimal dimerization motifs, as well as to identify sequences that compete with the wild-type assembly. In this way the shortest active peptides are obtained.

Various TLR TMD peptides and their analogs (mutants, truncated version and fatty acid conjugated) are synthesized based on the results of the ToxR and LexA systems. Homo- and hetero-assembly are determined by using various biophysical methods (experimental details are given in Korazim et al., 2006; Gerber et al., 2004 and Papo et al., 2002). Peptides are tested for their ability to interfere with the dimerization of the wild type TMD that is inserted within the ToxR and LexA systems.

Example 12. The Ability of the Synthetic Peptides to Inhibit TLRs Activation Induced by their Natural Ligands (LPS, LTA)

The peptides that showed significant effects on the assembly of the wild-type TMDs in the ToxR-TM-MalE and LexA-TM-MalE constructs (Example 11, above) are used. The ability of the synthetic peptides to inhibit TLRs activation induced by their natural ligands (LPS, LTA) is examined by: (i) measuring changes in the activation state of NF-κB (NF-κ inducible reporting system); (ii) measuring changes in the expression of pro/anti-inflammatory related molecules by real-time PCR (RT-PCR) or microarray analysis (only in a few specific cases); and (iii) following the secretion of pro-inflammatory cytokines TGF-β, IL-10, IL-8 and VEGF by ELISA. Results are normalized to the activity of TLRs natural ligand (LPS, LTA) or to non-stimulated cells.

Prostate cancer cells examined include human androgen-dependent (AD) and independent (AI) cell lines: (i) CL1 human PC cell (an AI subclone of LNCaP, which was generated by culturing AD LNCaP); (ii) 22RV1 human PC cells (AI sub-clones of the AD CWR22): PSA+, metastatic, ATCC strain; (iii) PC-3: AI, PSA+, metastatic, ATCC strain; (iv) DU-145: AI, PSA−, metastatic, ATCC strain; (v) CWR22: AD, PSA−, primary prostate cancer cells; (vi) WISH-2: AI, PSA−, small cell carcinoma of the prostate.

Normal human prostate and other non-cancer cells include: (i) CRL-11609: epithelial cells from histologically normal adult human prostate cells: AD, PSA+; metastatic, ATCC strain; (ii) 3T3 normal fibroblasts; (iii) OL foreskin fibroblasts; (iv) human lymphocytes; (v) human RBCs.

Example 13. The Anticancer Activity of the Synthetic Peptides In-Vivo

Nude mice prostate xenografts are generated in order to test the anticancer activity of the synthetic peptides (Table 2) by applying them intratumor, IP or IV. The effect on the microenvironment is tested by detecting the major cytokines and chemokines secreted at this area as well as characterizing the cell population entering the vicinity of the tumor e.g. T-regs, MDSC etc.

Example 14. Transmembrane Peptides Derived from TLR4 and TLR6 are Capable of Hetero-Dimerization Since in the case of Alzheimer's disease, the working hypothesis is that TLR4 and TLR6 heterodimerize, we investigated the role of the TMDs in their activation. The peptides derived from the TMDs of these receptors were synthesized and purified in our lab by standard procedures.

For the purpose of investigating hetero-dimerization in the membrane of living cells, two different reporter systems are used. For detecting homo-dimerization of TM domains, ToxR system that is routinely used in our lab is employed (see above). We have also constructed a new modified system to detect hetero-dimerization within TM domains by the GALLEX reporter system, a 2-hybrid system in E. coli to detect hetero-dimerizing TM segments (Schneider, D., and Engelman, D. M. (2003). GALLEX, a measurement of heterologous association of transmembrane helices in a biological membrane. J Biol Chem 278, 3105-3111; hereby incorporated by reference in its entirety). This system and the guidance for using it are kindly provided to us by Professor Dirk Schneider from University Mainz, Germany. These systems allow us to screen a variety of TM regions and mutants of TLRs 4 and 6, in order to identify the regions within the TMD that are important for the hetero-dimerization. Using these reporter system we are able to identify the amino acid residues that mostly contribute to the hetrodimerization and ultimately the most efficient peptides for inhibit the dimerization leading to the activation of the innate immune system cells and secretion of pro inflammatory mediators.

The peptides were investigated for their ability to co-assemble in membranes. For that purpose, we labeled TLR TM peptides with 4-chloro-7-nitrobenz-2-oxa-1,3-diazole fluoride [nitro benzoxadiazole (NBD)-F from Apollo] and Rhodamine. To mimic the membrane environment we used Large Unilamellar Vesicles (LUVs) composed of phosphatidylcholine (PC) and cholesterol (Chol) (10:1, w/w). We performed FRET experiments by using NBD-labeled TLR4 peptide as an energy donor and rhodamine-labeled TLR6 peptide as an energy acceptor. FIG. 14 demonstrates a strong FRET which supports our working hypothesis.

FIG. 15 shows the dimerization activity of the different TLR4 and TLR6 transmembrane (TM) segments using a GALLEX assembly system, a two-hybrid system to follow the heterodimerization of membrane proteins in the Escherichia coli inner membrane. The method is based on the repression of a reporter gene activity by two LexA DNA binding domains with different DNA binding specificities. When coupled to transmembrane domains, heterodimeric association is reported by repression of β-galactosidase synthesis.

Dimerization was demonstrated in comparison to a mutant glycophorin A, GPA, G83I, that is deficient in its ability to form dimers and the positive control, GPA. In this assay, a low signal indicates dimerization (as in the first three bars from the left and the positive control, GPA) and a relatively high signal indicates inability to form dimers.

Example 16. Transmembrane Peptides Derived from TLR4 and TLR6 are Capable of Inhibiting Activation of Macrophage TLRs TLRs have been shown to be activated in heterodimeric state. Thus, we studied the ability of the peptides of TLR4 C1 (SEQ ID NO: 95); TLR 4 C2 (SEQ ID NO:90); TLR6 C9 (SEQ ID NO:83); TLR6 N6 (SEQ ID NO:96) to regulate the hetero-assembly of TLR4 and TLR6, resulting in the activation of mouse macrophages cells line. The activation of the macrophage was engaged by secretion levels of the pro-inflammatory cytokine, TNF-α. This experiment was done on macrophages since their involvement in secretion of proinflammatory mediators in Alzheimer's disease was previously disclosed.

As shown in FIG. 16, addition of soluble TLR6 and TLR4 TM peptides inhibited macrophage activation after stimulation with fAβ.

Example 17. Functional Studies with the Synthetic Peptides

The TLR4 and TLR6 peptides are further analyzed for their ability to impair the activity of the full-length receptor and to serve as novel inhibitors of macrophage and/or microglia cell activation by fibrillar β-amyloid. This is examined by several experimental methods in the presence and absence of peptides. The methods include:

(1) Following changes in the activation state of NF-κB after stimulation with fAβ. HEK293 cells are co-transfected with TLR4, TLR6 and NF-κB luciferase reporter gene. After stimulation with ligand, cells are lysed and reporter gene activity is measure using the Dual luciferase assay reporter system. This system allows us to determine the level of activation of the different peptides resulting in decrease of luciferase compared with untreated cells. Moreover, the use of cells with different genotype allows us to estimate the specificity of the system;

(2) Following changes in the expression of pro-inflammatory related molecules by RT-PCR;

(3) Following the secretion of pro-inflammatory cytokines TNF-α, IL-1b, and IL-6 by ELISA.

In all the experiments the effect of the peptides is normalized to non-stimulated cells. We first use RAW264.7 mouse macrophages and then repeat this assay using murine BV-2 microglia cells. Finally, we utilize neurotoxicity assay to assess microglia-induced neurotoxicity using mouse neuronal cells, wild type and knock-out microglia (TLR4$^{-/-}$, TLR6$^{-/-}$). Neuronal survival is calculated using confocal microscope after 72 h of incubation with fAB. Measurement of ROS and NO will be done by nitroblue tetrazolium (NBT) reduction assay, and nitric oxide will be measure by Griess reaction.

In order to examine the ability of the TMDs derived peptides to inhibit NO-secretion, 1×10$^5$ cells per well are cultured overnight in 96-wells plate. The following day, the media is replaced by fresh DMEM, including all supplements and TLR peptides dissolved in DMSO are added to the cells in different concentrations. Final concentration of DMSO is 1% for all groups. Cells are incubated with the peptide for 2 hours, then washed twice and incubated with fresh media containing 10 μM fibrillar beta amyloide for 5 to 24 hours at 37° C., after which samples of the media from each treatment are collected and immediately used in the kit.

The Griess Reagent System (Promega) detects NO$_2$ and is based on the chemical reaction which uses sulfanilamide and N-1-napthylethylenediamine dihydrochloride.

Example 18. Assessing Therapeutic Efficacy of Peptides of TLR4 and TLR6 Tm Domains in the TgCRND8 Mice Model for Alzheimer's Disease TgCRND8 amyloid precursor protein transgenic mice are treated with peptides derived from TLR4 and TLR6 TM domains for up to 24 treatments IP, IV and intra-cranial and the development rate of Alzheimer's disease is monitored; by the formation of amyloid core plaques and behavioral studies, additionally, immuno-histological staining for IL-1β, TNFα and IL-6 is performed to evaluate the levels of microglia activation in-vivo.

REFERENCES

Bennasroune, A., Fickova, M., Gardin, A., Dirrig-Grosch, S., Aunis, D., Cremel, G. & Hubert, P. (2004) Mol Biol Cell 15, 3464-74.
Cohen, T., Pevsner-Fischer, M., Cohen, N., Cohen, I. R. & Shai, Y. (2008) Biochemistry 47, 4826-4833.
Fassbender K, Walter S, Kuhl S, Landmann R, Ishii K, Bertsch T, Stalder A, Muehlhauser F, Liu Y, Ulmer A, Rivest S, Lentschat A, Gulbins E, Jucker M, Stafenbiel M, Brechtel K, Walter J, Multhaup G, Penke B, Adachi Y, Hartmann T, Beyreuther K (2004) The LPS receptor (CD14) links innate immunity with Alzheimer's disease. FASEB J 18:203-205.
Foster, S. L. & Medzhitov, R. (2009) Clin Immunol 130, 7-15.
Frillingos, S., Sahin-Toth, M., Wu, J., and Kaback, H. R. (1998). Cys-scanning mutagenesis: a novel approach to structure function relationships in polytopic membrane proteins. Faseb J 12, 1281-1299.
Gerber, D. & Shai, Y. (2001) In vivo detection of heteroassociation of glycophorin-A and its mutants within the membrane. J. Biol. Chem. 276, 31229-31232.
Gerber D, Pritsker M, Gunther-Ausborn S, Johnson B, Blumenthal R, Shai Y. (2004) Inhibition of HIV-1 envelope glycoprotein-mediated cell fusion by a DL-amino acid-containing fusion peptide: possible recognition of the fusion complex. J Biol Chem, 279(46), 48224-30.
Hajjar, A. M., O'Mahony, D. S., Ozinsky, A., Underhill, D. M., Aderem, A., Klebanoff, S. J. & Wilson, C. B. (2001). Cutting edge: functional interactions between toll-like receptor (TLR) 2 and TLR1 or TLR6 in response to phenol-soluble modulin. J Immunol 166, 15-9.
He, M. M., Sun, J., and Kaback, H. R. (1996). Cysteine-scanning mutagenesis of transmembrane domain XII and the flanking periplasmic loop in the lactose permease of EScherichia coli. Biochemistry 35, 12909-12914.
Huang, B., Zhao, J., Shen, S., Li, H., He, K. L., Shen, G. X., Mayer, L., Unkeless, J., Li, D., Yuan, Y., Zhang, G. M., Xiong, H. & Feng, Z. H. (2007) Cancer Res 67, 4346-52.
Huang, B., Zhao, J., Li, H., He, K. L., Chen, Y., Chen, S. H., Mayer, L., Unkeless, J. C. & Xiong, H. (2005). Toll-like receptors on tumor cells facilitate evasion of immune surveillance. Cancer Res 65, 5009-14.
Jin, M. S., Kim, S. E., Heo, J. Y., Lee, M. E., Kim, H. M., Paik, S. G., Lee, H. & Lee, J. O. (2007). Crystal structure of the TLR1-TLR2 heterodimer induced by binding of a tri-acylated lipopeptide. Cell 130, 1071-1082.
Kajita, E., Nishiya, T. & Miwa, S. (2006) Biochem Biophys Res Commun 343, 578-84.
Korazim, O., K. Sackett, and Y. Shai, (2006) Functional and structural characterization of HIV-1 gp41 ectodomain regions in phospholipid membranes suggests that the fusion-active conformation is extended. J Mol Biol. 364 (5), 1103-17.
Kundu, S. D., Lee, C., Billips, B. K., Habermacher, G. M., Zhang, Q., Liu, V., Wong, L. Y., Klumpp, D. J. & Thumbikat, P. (2008). The toll-like receptor pathway: a novel mechanism of infection-induced carcinogenesis of prostate epithelial cells. Prostate 68, 223-9.
Langosch, D., Brosig, B., Kolmar, H. & Fritz, H. J. (1996). Dimerisation of the glycophorin A transmembrane segment in membranes probed with the ToxR transcription activator. J. Mol. Biol. 263, 525-530.
Lee, H. K., Dunzendorfer, S. & Tobias, P. S. (2004). Cytoplasmic domain-mediated dimerizations of toll-like receptor 4 observed by beta-lactamase enzyme fragment complementation. J Biol Chem 279, 10564-74.
Lehnardt S, Massillon L, Follett P, Jensen F E, Ratan R, Rosenberg P A, Volpe J J, Vartanian T (2003) Activation of innate immunity in the CNS triggers neurodegeneration through a Toll-like receptor 4-dependent pathway. Proc Natl Acad Sci USA 100:8514-8519
Lindner, E. & Langosch, D. (2006). A ToxR-based dominant-negative system to investigate heterotypic transmembrane domain interactions. Proteins 65, 803-807.
Mendrola, J. M., Berger, M. B., King, M. C. & Lemmon, M. A. (2002) J Biol Chem 277, 4704-12.
Meng, G., Rutz, M., Schiemann, M., Metzger, J., Grabiec, A., Schwandner, R., Luppa, P. B., Ebel, F., Busch, D. H., Bauer, S., Wagner, H. & Kirschning, C. J. (2004) J Clin Invest 113, 1473-81.
Mitchell, J. A., Paul-Clark, M. J., Clarke, G. W., McMaster, S. K. & Cartwright, N. (2007) J Endocrinol 193, 323-30.
Nishiya, T., Kajita, E. & Miwa, S. (2006) Biochem Biophys Res Commun 341, 1128-34.

O'Neill, L. A. & Bowie, A. G. (2007) Nat Rev Immunol 7, 353-64.

Ozinsky, A., Underhill, D. M., Fontenot, J. D., Hajjar, A. M., Smith, K. D., Wilson, C. B., Schroeder, L. & Aderem, A. (2000). The repertoire for pattern recognition of pathogens by the innate immune system is defined by cooperation between toll-like receptors. Proc Natl Acad Sci USA 97, 13766-71

Papo, N., Seger, D., Makovitzki, A., Kalchenko, V., Eshhar, Z., Degani, H. & Shai, Y. (2006) Cancer Research 66, 5371-5378.

Papo, N., Braunstein, A., Eshhar, Z. & Shai, Y. (2004) Cancer Research 64, 5779-5786.

Papo, N., Oren, Z., Pag, U., Sahl, H. G. & Shai, Y. (2002) Journal of Biological Chemistry 277, 33913-33921.

Quintana, F. J., Gerber, D., Bloch, I., Cohen, I. R. & Shai, Y. (2007) Biochemistry 46, 2317-25.

Rapaport, D. & Shai, Y. (1991) Journal of Biological Chemistry 266, 23769-23775.

Rolls, A., Shechter, R., London, A., Ziv, Y., Ronen, A., Levy, R. & Schwartz, M. (2007) Nat Cell Biol 9, 1081-8.

Rosenfeld, Y., Papo, N. & Shai, Y. (2006a) J Biol Chem 281, 1636-43.

Rosenfeld, Y., Barra, D., Simmaco, M., Shai, Y. & Mangoni, M. L. (2006b) J Biol Chem 281, 28565-74.

Rosenfeld, Y. & Shai, Y. (2006c) Biochim Biophys Acta 1758, 1513-22.

Russ, W. P. & Engelman, D. M. (1999) Proc Natl Acad Sci USA 96, 863-8.

Saenz-Abad, D., Letona-Carbajo, S., Benito-Arevalo, J. L., Sanioaquin-Conde, I. & Ruiz-Ruiz, F. J. (2008). Prostatic tuberculosis: case report. Sao Paulo Med J 126, 227-8.

Sal-Man, N., Gerber, D. & Shai, Y. (2005) J Biol Chem 280, 27449-57.

Sal-Man, N., Gerber, D. & Shai, Y. (2004) Biochemistry 43, 2309-13.

Sato, Y., Goto, Y., Narita, N. & Hoon, D. S. (2009). Cancer Cells Expressing Toll-like Receptors and the Tumor Microenvironment. Cancer Microenviron 2 Suppl 1, 205-14

Sfanos, K. S. & Isaacs, W. B. (2008). An evaluation of PCR primer sets used for detection of *Propionibacterium acnes* in prostate tissue samples. Prostate 68, 1492-5.

Shi, H., Kokoeva, M. V., Inouye, K., Tzameli, I., Yin, H. & Flier, J. S. (2006) J Clin Invest 116, 3015-25.

Sung-Chun Tanga,b,c, Justin D. Lathiaa, Pradeep K. Selvarajf, Dong-Gyu Joa,d, Mohamed R. Mughala, Aiwu Chenga, Dominic A. Silera, William R. Markesberye, Thiruma V. Arumugamf, and Mark. P. Mattsona,g, (2008) Toll-Like Receptor-4 Mediates Neuronal Apoptosis Induced by Amyloid δ-Peptide and the Membrane Lipid Peroxidation Product 4-Hydroxynonenal. Exp Neurol. 213(1): 114-121

Stewart C R, Stuart L M, Wilkinson K, van Gils J M, Deng J, Halle A, Rayner K J, Boyer L, Zhong R, Frazier W A, Lacy-Hulbert A, El Khoury J, Golenbock D T, Moore K J. (2010) 3.CD36 ligands promote sterile inflammation through assembly of a Toll-like receptor 4 and 6 heterodimer. Nat Immunol. 11(2):155-61.

Walter S, Letiembre M, Liu Y, Heine H, Penke B, Hao W, Bode B, Manietta N, Walter J, Schulz-Schaeffer W, Fassbender K (2007) Role of the Toll-like receptor 4 in neuro-inflammation in Alzheimer's disease. Cell Physiol Biochem 20:947-956

The invention claimed is:

1. A synthetic peptide comprising the amino acid sequence selected from the group consisting of SEQ ID NOs: 75-90, 92-94, 96-120 and 121, wherein said synthetic peptide inhibits cell activation mediated by a Toll-like receptor (TLR).

2. A pharmaceutical composition comprising the synthetic peptide according to claim 1, and a pharmaceutically acceptable carrier.

3. A synthetic peptide comprising the amino acid sequence selected from the group consisting of SEQ ID NO: 1-5, 7, 9, 11, 16-20 and 23, said amino acid sequence being linked at its N- and/or C-termini to an additional one to four positively charged amino acid residues, wherein said synthetic peptide inhibits cell activation mediated by a TLR.

4. The synthetic peptide according to claim 3, wherein said positively charged amino acid is selected from the group consisting of lysine, arginine, histidine and ornithine.

5. The synthetic peptide according to claim 4, wherein one or two lysine residues are added to one or both of the N or C termini.

6. A pharmaceutical composition comprising the synthetic peptide according to claim 3, and a pharmaceutically acceptable carrier.

7. A synthetic peptide of at most 30 amino acid residues comprising an amino acid sequence selected from the group consisting of SEQ ID NO: 1, 3, 5, 7, 9, 11, 17-20, 23, 25-28 and 30-39, said amino acid sequence being linked at its N- and/or C-termini to an additional one to four positively charged amino acid residues, wherein said synthetic peptide inhibits cell activation mediated by said TLR.

8. The synthetic peptide according to claim 7, wherein said positively charged amino acid is selected from the group consisting of lysine, arginine, histidine and ornithine.

9. The synthetic peptide according to claim 8, wherein one or two lysine residues are added to one or both of the N or C termini.

10. A pharmaceutical composition comprising the synthetic peptide according to claim 7, and a pharmaceutically acceptable carrier.

11. The synthetic peptide according to claim 1, wherein said amino acid sequence comprises at least one D amino acid.

12. The synthetic peptide according to claim 3, wherein said amino acid sequence comprises at least one D amino acid.

13. The synthetic peptide according to claim 7, wherein said amino acid sequence comprises at least one D amino acid.

\* \* \* \* \*